(12) United States Patent
Ackermann et al.

(10) Patent No.: US 6,683,201 B2
(45) Date of Patent: Jan. 27, 2004

(54) ANALINE DERIVATIVES AS OSC INHIBITORS

(75) Inventors: Jean Ackermann, Riehen (CH); Johannes Aebi, Basel (CH); Alexander Chucholowski, San Diego, CA (US); Henrietta Dehmlow, Grenzach-Wyhlen (DE); Olivier Morand, Hegenheim (FR); Sabine Wallbaum, Ostfildern (DE); Thomas Weller, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 260 days.

(21) Appl. No.: 09/906,214

(22) Filed: Jul. 16, 2001

(65) Prior Publication Data

US 2002/0038025 A1 Mar. 28, 2002

(30) Foreign Application Priority Data

Jul. 18, 2000 (EP) .............................. 00115451

(51) Int. Cl.$^7$ ............................................ C07C 229/00
(52) U.S. Cl. ................. 560/43; 560/24; 564/74; 564/79; 564/80; 564/84; 564/86; 564/92; 564/123; 564/161; 564/168; 564/176; 558/232
(58) Field of Search ................. 560/24, 43; 564/74, 564/79, 80, 84, 86, 92, 123, 161, 168, 176; 558/232

(56) References Cited

U.S. PATENT DOCUMENTS 5,637,771 A    6/1997    Aebi et al.

FOREIGN PATENT DOCUMENTS

| EP | 0 636 367 | 2/1995 |
| EP | 636367 | 2/1995 |
| EP | 0 778 264 | 6/1997 |
| GB | 1 055 548 | 1/1967 |
| WO | WO 91 01299 | 2/1991 |
| WO | WO 93 20807 | 10/1993 |

OTHER PUBLICATIONS

Bromme, *Drug News Perspect*, 12(2), pp. 73–82 (1999).
Chapman, et al, *Annu. Rev. Phys.*, 59, pp. 63–88, (1997).
Tezuka, et al, *Biol. Chem.*, 269, pp. 1106–1109 (1994).
Lerner, et al, *Bone Min. Res.*, 7, pp.433 (1992).
Everts, et al, *Cell. Physiol.*, 150, pp. 221 (1992).
Hummel, et al, *J. Rheumatol*, 25(10), pp. 1887–1894 (1998).
Libbey, et al, *J. Clin. Invest.*, 102(3), pp. 576–583, (1998).
Littlewood–Evans, et al, *Cancer Res*, 57, pp. 5386–5390 (1997).
Schirmeister, et al, *Chem. Rev.*, 97 pp. 133–171 (1997).
Verber, et al, *Proc. Natl. Acad. Sci.*USA, 94, pp. 14249–14254 (1997).
Wiederanders, et al, *Eur. J. Biochem*, 250, 745–750 (1997).

*Primary Examiner*—Paul J. Killos
(74) *Attorney, Agent, or Firm*—George W. Johnston; Patricia S. Rocha-Tramaloni; Bernard Lau

(57) ABSTRACT

The present invention relates to compounds of formula (I)

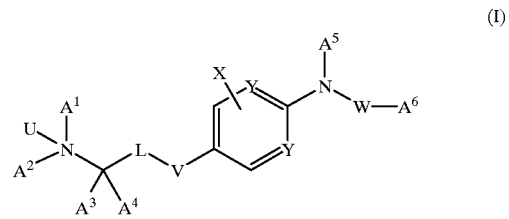

(I)

wherein U, Y, V, W, L, X, $A^1$, $A^2$, $A^3$, $A^4$, $A^5$ and $A^6$ are as defined in the description and claims and pharmaceutically acceptable salts and/or pharmaceutically acceptable esters thereof. The compounds are useful for the treatment and/or prophylaxis of diseases which are associated with 2,3-oxidosqualene-lanosterol cyclase such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes.

32 Claims, No Drawings

ANALINE DERIVATIVES AS OSC INHIBITORS

FIELD OF THE INVENTION

The present invention is concerned with novel aniline derivatives, their manufacture and their use as medicaments. The compounds of the present invention inhibit 2,3-oxidosqualene-lanosterol cyclase (EC5.4.99.) which is required for the biosynthesis of cholesterol, ergosterol and other sterols.

BACKGROUND

Causal risk factors that directly promote the development of coronary and peripheral atherosclerosis include elevated low-density lipoprotein cholesterol (LDL-C), low high-density lipoprotein cholesterol (HDL-C), hypertension, cigarette smoking and diabetes mellitus. Other synergistic risk factors include elevated concentrations of triglyceride (TG)-rich lipoproteins, small, dense low-density lipoprotein particles, lipoprotein (a) (Lp(a)), and homocysteine. Predisposing risk factors modify the causal or conditional risk factors and thus affect atherogenesis indirectly. The predisposing risk factors are obesity, physical inactivity, family history of premature CVD, and male sex. The strong connection between coronary heart disease (CHD) and high LDL-C levels in plasma, and the therapeutic advantage of lowering elevated LDL-C levels are now well established (Gotto et al., Circulation 81, 1990, 1721–1733; Stein et al., Nutr. Metab. Cardiovasc. Dis. 2, 1992, 113–156; Illingworth, Med. Clin. North. Am. 84, 2000, 23–42). Cholesterol-rich, sometimes unstable, atherosclerotic plaques lead to the occlusion of blood vessels resulting in an ischemia or an infarct. Studies with respect to primary prophylaxis have shown that a lowering of plasma LDL-C levels in plasma reduces the frequency of non-fatal incidences of CHD, while the overall morbidity remains unchanged. The lowering of plasma LDL-C levels in patients with pre-established CHD (secondary intervention) reduces CHD mortality and morbidity; meta-analysis of different studies shows that this decrease is proportional to the reduction of the LDL-C (Ross et al., Arch. Intern. Med. 159, 1999, 1793–1802).

The clinical advantage of cholesterol lowering is greater for patients with pre-established CHD than for asymptomatic persons with hypercholesterolemia. According to current guidelines, cholesterol lowering treatment is recommended for patients who had survived a myocardial infarct or patients suffering from angina pectoris or another atherosclerotic disease, with a target LDL-C level of 100 mg/dl.

Preparations such as bile acid sequestrants, fibrates, nicotinic acid, probucol as well as statins, i.e. HMG-Co-A reductase inhibitors such as simvastatin and atorvastatin, are used for usual standard therapies. The best statins reduce plasma LDL-C effectively by at least 40%, and also plasma triglycerides, a synergistic risk factor, but less effectively. In contrast, fibrates reduce plasma triglycerides effectively, but not LDL-C. Combination of a statin and a fibrate proved to be very efficacious in lowering LDL-C and triglycerides (Ellen and McPherson, J. Cardiol. 81, 1998, 60B–65B), but safety of such a combination remains an issue (Shepherd, Eur. Heart J. 16, 1995, 5–13). A single drug with a mixed profile combining effective lowering of both LDL-C and triglycerides would provide additional clinical benefit to asymptomatic and symptomatic patients.

In humans, statins are well tolerated at standard dosage, but reductions in non-sterol intermediates in the cholesterol synthesis pathway, such as isoprenoids and coenzyme Q, may be associated with adverse clinical events at high doses (Davignon et al., Can. J. Cardiol. 8, 1992, 843–864; Pederson and Tobert, Drug Safety 14, 1996, 11–24).

This has stimulated the search for, and development of compounds that inhibit cholesterol biosynthesis, yet act distal to the synthesis of these important, non-sterol intermediates. 2,3-oxidosqualene:lanosterol cyclase (OSC), a microsomal enzyme, represents a unique target for a cholesterol-lowering drug (Morand et al., J. Lipid Res., 38, 1997, 373–390; Mark et al., J. Lipid Res. 37, 1996, 148–158). OSC is downstream of farnesyl-pyrophosphate, beyond the synthesis of isoprenoids and coenzyme Q. In hamsters, pharmacologically active doses of an OSC inhibitor showed no adverse side-effects, in contrast to a statin which reduced food-intake and body weight, and increased plasma bilirubin, liver weight and liver triglyceride content (Morand et al., J. Lipid Res., 38, 1997, 373–390). The compounds described in European Patent Application No. 636 367, which inhibit OSC and which lower the total cholesterol in plasma, belong to these substances.

OSC inhibition does not trigger the overexpression of HMGR because of an indirect, negative feed-back regulatory mechanism involving the production of 24(S),25-epoxycholesterol (Peffley et al., Biochem. Pharmacol. 56, 1998, 439–449; Nelson et al., J. Biol. Chem. 256, 1981, 1067–1068; Spencer et al., J. Biol. Chem. 260, 1985, 13391–13394; Panini et al., J. Lipid Res. 27, 1986, 1190–1204; Ness et al., Arch. Biochem. Biophys. 308, 1994, 420–425). This negative feed-back regulatory mechanism is fundamental to the concept of OSC inhibition because (i) it potentiates synergistically the primary inhibitory effect with an indirect down-regulation of HMGR, and (ii) it prevents the massive accumulation of the precursor monooxidosqualene in the liver. In addition, 24(S),25-epoxycholesterol was found to be one of the most potent agonists of the nuclear receptor LXR (Janowski et al., Proc. Natl. Acad. Sci. USA, 96, 1999, 266–271). Considering that 24(S),25-epoxycholesterol is a by-product of inhibition of OSC it is hypothesized that the OSC inhibitors of the present invention could also indirectly activate LXR-dependent pathways such as (i) cholesterol-7alpha-hydroxylase to increase the consumption of cholesterol via the bile acid route, (ii) expression of ABC proteins with the potential to stimulate reverse cholesterol transport and increase plasma HDL-C levels (Venkateswaran et al., J. Biol. Chem. 275, 2000, 14700–14707; Costet et al., J. Biol. Chem. June 2000, in press; Ordovas, Nutr Rev 58, 2000, 76–79, Schmitz and Kaminsky, Front Biosci 6, 2001, D505–D514), and/or inhibit intestinal cholesterol absorption (Mangelsdorf, XIIth International Symposium on Atherosclerosis, Stockholm, June 2000). In addition, possible cross talks between fatty acid and cholesterol metabolism mediated by liver LXR have been hypothesized (Tobin et al., Mol. Endocrinol. 14, 2000, 741–752).

BRIEF DESCRIPTION OF THE INVENTION

The invention relates to a compound of the formula (I)

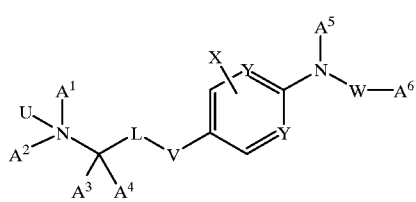

(I)

wherein
U is O or a lone pair,
Y is C or N,
V is O, S, NR⁶, —CH₂—, —CH=CH—, or —C≡C—, if Y is C, or —CH₂—, —CH=CH—, —C≡C—, if Y is N,
W is CO, COO, CONR¹, CSO, CSNR¹, SO₂, or SO₂NR¹,
L is lower-alkylene, lower-alkenylene, or a single bond,
A¹ is H, lower-alkyl, or lower-alkenyl,
A² is lower-alkyl, cycloalkyl, cycloalkyl-lower-alkyl, lower-alkenyl, or lower-alkinyl, each unsubstituted or substituted by R²,
A³, A⁴ are hydrogen or lower-alkyl, or
A¹ and A² or A¹ and A³ are bonded to each other to form a ring and —A¹—A²— or —A¹—A³— are lower-alkylene or lower-alkenylene, each unsubstituted or substituted by R², or are lower-alkylene or lower-alkenylene, each unsubstitued or substituted by R², in which one —CH₂— group of —A¹—A²— or —A¹—A³— is replaced by NR³, S, or O,
A⁵ is lower-alkyl,
X is hydrogen or one or more halogen substituents,
A⁶ is lower-alkyl, cycloalkyl, cycloalkyl-lower-alkyl, heterocycloalkyl-lower-alkyl, lower alkenyl, lower-alkadienyl, aryl, aryl-lower-alkyl, heteroaryl, or heteroaryl-lower-alkyl,
R² is hydroxy, hydroxy-lower-alkyl, lower-alkoxy, N(R⁴, R⁵), or lower-alkoxycarbonyl,
R¹, R³, R⁴, R⁵ and R⁶ independently from each other are hydrogen or lower-alkyl, or a pharmaceutically acceptable salt or pharmaceutically acceptable ester thereof.

The present compounds of formula I and their salts and esters inhibit OSC and therefore also inhibit the biosynthesis of cholesterol, ergosterol and other sterols, and reduce the plasma cholesterol levels. They can therefore be used in the therapy and prophylaxis of hypercholesterolemia, hyperlipemia, arteriosclerosis and vascular diseases in general. Furthermore, they can be used in the therapy and/or prevention of mycoses, parasite infections, gallstones, cholestatic liver disorders, tumors and hyperproliferative disorders, e.g. hyperproliferative skin and vascular disorders. In addition, it has unexpectedly been found that the compounds of the present invention can also be of therapeutical use to improve glucose tolerance in order to treat and/or prevent related diseases such as diabetes. The compounds of the present invention further exhibit improved pharmacological properties compared to known compounds.

DETAILED DESCRIPTION OF THE INVENTION

Unless otherwise indicated the following definitions are set forth to illustrate and define the meaning and scope of the various terms used to describe the invention herein.

In this specification the term "lower" is used to mean a group consisting of one to seven, preferably of one to four carbon atom(s).

The term "lone pair" refers to an unbound electron pair, in particular to the unbound electron pair of a nitrogen atom in e.g. an amine.

The term "halogen" refers to fluorine, chlorine, bromine and iodine, with chlorine, bromine and iodine being preferred.

The term "alkyl", alone or in combination with other groups, refers to a branched or straight-chain monovalent saturated aliphatic hydrocarbon radical of one to twenty carbon atoms, preferably one to sixteen carbon atoms. Alkyl groups can be substituted e.g. with halogen, CN, NO₂ and/or aryl. Other, more preferred substituents are hydroxy, lower-alkoxy, aryl, NH₂, N(lower-alkyl)₂ and/or lower-alkoxycarbonyl.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may have a substitution pattern as described earlier in connection with the term "alkyl".

The term "cycloalkyl" refers to a monovalent carbocyclic radical of 3 to 10 carbon atom(s), preferably 3 to 6 carbon atoms. A cycloalykl group may also be bicyclic. A cycloalkyl group may have a substitution pattern as described earlier in connection with the term "alkyl". Cycloalkyl in which one or —CH₂— group is replaced by O, S, NH or N(lower-alkyl) are referred to as "heterocycloalkyl".

The term "alkoxy" refers to the group R'—O—, wherein R' is an alkyl. The term "lower alkoxy" refers to the group R'—O—, wherein R' is a lower alkyl.

The term "alkenyl", alone or in combination with other groups, stands for a straight-chain or branched hydrocarbon residue comprising an olefinic bond and up to 20, preferably up to 16 carbon atoms. The term "lower-alkenyl" refers to a straight-chain or branched hydrocarbon residue comprising an olefinic bond and up to 7, preferably up to 4 carbon atoms, such as e.g. 2-propenyl. An alkenyl or lower-alkenyl group may have a substitution pattern as described earlier in connection with the term "alkyl".

The term "alkadienyl", alone or in combination with other groups, stands for a straight-chain or branched hydrocarbon residue comprising 2 olefinic bonds and up to 20, preferably up to 16 carbon atoms. The term "lower-alkadienyl" refers to a straight-chain or branched hydrocarbon residue comprising 2 olefinic bonds and up to 7 carbon atoms. An alkadienyl or lower-alkadienyl group may have a substitution pattern as described earlier in connection with the term "alkyl".

The term "alkinyl", alone or in combination with other groups, stands for a straight-chain or branched hydrocarbon residue comprising a tripple bond and up to 20, preferably up to 16 carbon atoms. The term "lower-alkinyl" refers to a straight-chain or branched hydrocarbon residue comprising a tripple bond and up to 7, preferably up to 4 carbon atoms, such as e.g. 2-propinyl. An alkinyl or lower-alkinyl group may have a substitution pattern as described earlier in connection with the term "alkyl".

The term "alkylene" refers to a straight chain or branched divalent saturated aliphatic hydrocarbon group of 1 to 20 carbon atoms, preferably 1 to 16 carbon atoms. The term "lower-alkylene" refers to a straight chair, or branched divalent saturated aliphatic hydrocarbon group of 1 to 7, preferably 2 to 4 carbon atoms. An alkylene or lower-alkylene group may have a substitution pattern as described earlier in connection with the term "alkyl".

The term "alkenylene" refers to a straight chain or branched divalent hydrocarbon group comprising an olefinic bond and up to 20 carbon atoms, preferably up to 16 carbon atoms. The term "lower-alkenylene" refers to a straight chain or branched divalent hydrocarbon group comprising an olefinic bond and up to 7, preferably up to 4 C-atoms. An alkenylene or lower-alkenylene group may have a substitution pattern as described earlier in connection with the term "alkyl".

The term "aryl" relates to the phenyl or naphthyl group which can optionally be mono- or multiply-substituted by lower-alkyl, lower-alkyl-di-oxo, halogen, hydroxy, cyano, $CF_3$, $NH_2$, N(lower-alkyl)$_2$, aminocarbonyl, carboxy, nitro, lower-alkoxy, lower-alkylcarbonyl, lower-alkylcarbonyloxy, aryl, or aryloxy. Preferred substituents are lower-alkyl, fluorine, chlorine, bromine, lower-alkoxy, cyano, $CF_3$, $NO_2$, $NH_2$, and/or N(lower-alkyl)$_2$. More preferred substituents are chlorine and $CF_3$.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, pyrrolyl, with furyl, thienyl and pyridyl being preferred. The term "heteroaryl" further refers to bicyclic aromatic groups comprising two 5- or 6-membered rings, in which one or both rings can contain 1, 2 or 3 atoms selected from nitrogen, oxygen or sulphur such as e,g, indol or chinolin. A heteroaryl group may have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulphuric acid, phosphoric acid, citric acid, formic acid, maleic acid, acetic acid, fumaric acid, succinic acid, tartaric acid, methanesulphonic acid, p-toluenesulphonic acid and the like, which are non toxic to living organisms.

The term "pharmaceutically acceptable esters" embraces esters of the compounds of formula (I), in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "protecting group" refers to groups such as acyl, azoyl, alkoxycarbonyl, aryloxycarbonyl, or silyl. Examples are e.g. t-butyloxycarbonyl or benzyloxycarbonyl which can be used for the protection of amino groups or trimethylsilyl or dimethyl-tert.-butyl-silyl, which can be used for the protection of hydroxy groups.

In detail, the present invention relates to compounds of formula (I)

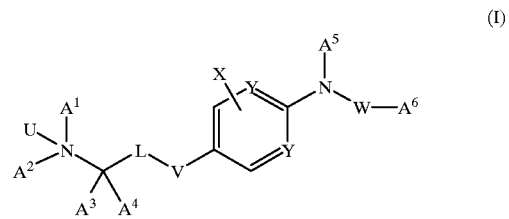

wherein

U is O or a lone pair,
Y is C or N,
V is O, S, $NR^6$, —$CH_2$—, —CH=CH—, —C≡C—, if Y is C, or —$CH_2$—, —CH=CH—, —C≡C—, if Y is N,
W is CO, COO, $CONR^1$, CSO, $CSNR^1$, $SO_2$, or $SO_2NR^1$,
L is lower-alkylene, lower-alkenylene, or a single bond,
$A^1$ is H, lower-alkyl, or lower-alkenyl,
$A^2$ is lower-alkyl, cycloalkyl, cycloalkyl-lower-alkyl, lower-alkenyl, or lower-alkinyl, optionally substituted by $R^2$,
$A^3$, $A^4$ are hydrogen or lower-alkyl, or
$A^1$ and $A^2$ or $A^1$ and $A^3$ are bonded to each other to form a ring and —$A^1$—$A^2$— or —$A^1$—$A^3$— are lower-alkylene or lower-alkenylene, optionally substituted by $R^2$, in which one —$CH_2$— group of —$A^1$—$A^2$— or —$A^1$—$A^3$— can optionally be replaced by $NR^3$, S, or O,
$A^5$ is lower-alkyl,
X is hydrogen or one or more optional halogen substituents,
$A^6$ is lower-alkyl, cycloalkyl, cycloalkyl-lower-alkyl, heterocycloalkyl-lower-alkyl, lower alkenyl, lower-alkadienyl, aryl, aryl-lower-alkyl, heteroaryl, or heteroaryl-lower-alkyl,
$R^2$ is hydroxy, hydroxy-lower-alkyl, lower-alkoxy, N($R^4$, $R^5$), or lower-alkoxycarbonyl,
$R^1$, $R^3$, $R^4$, $R^5$ and $R^6$ independently from each other are hydrogen or lower-alkyl, and pharmaceutically acceptable salts and/or pharmaceutically acceptable esters thereof.

Preferred are compounds of formula (I) and/or pharmaceutically acceptable salts thereof. Another preferred embodiment relates to compounds of formula (I) wherein U is a lone pair. Other preferred compounds of formula (I) are those wherein U is O. Further, compounds of formula (I) in which Y represents C are preferred.

Compounds of formula (I) in which V is O, —C≡C—, or —$CH_2$— relate to another preferred embodiment of the present invention. Compounds of formula (I) in which V represents O are particularly preferred.

Of the compounds of the present invention, those in which W represents COO, $SO_2$, or $CSNR^1$ and $R^1$ is hydrogen are preferred, as are those in which L is lower-alkylene or a single bond, or more preferably L is —(CH$_2$)$_{2-4}$—.

Other preferred compounds of formula (I) are those in which $A^1$ represents methyl, ethyl or 2-propenyl. Another group of preferred compounds of formula (I) are those in which $A^2$ represents lower-alkyl, cycloalkyl, lower-alkenyl, or lower-alkinyl, optionally substituted with $R^2$, wherein $R^2$ is hydroxy, methoxy, or ethoxycarbonyl, with those compounds wherein $A^2$ represents methyl, ethyl, 2-hydroxyethyl, or 2-propenyl being especially preferred.

Compounds of formula (I), wherein $A^1$ and $A^2$ are bonded to each other to form a ring and —$A^1$—$A^2$— is lower-alkylene, or lower-alkenylene, optionally substituted by $R^2$, in which one —$CH_2$— group or —$A^1$—$A^2$— can optionally be replaced by $NR^3$, S, or O, wherein $R^2$ and $R^3$ are as defined above are also preferred, with compounds wherein $R^2$ is methyl, hydroxy, 2-hydroxyethyl, or $N(CH_3)_2$ and/or $R^3$ is methyl being particularly preferred. In compounds wherein $A^1$ and $A^2$ are bonded to each other to form a ring, said ring is preferably a 5-, 6- or 7-membered ring such as e.g. piperidinyl or pyrrolidinyl.

Further individually preferred embodiments of the present invention relate to compounds of formula (I) wherein $A^3$ represents hydrogen and to compounds of formula (I) wherein $A^4$ represents hydrogen. Compounds of formula (I) in which $A^5$ is methyl or ethyl are also preferred, as are compounds of formula (I) in which X is hydrogen.

Compounds of formula (I), wherein $A^6$ represents lower-alkyl, lower-alkenyl, phenyl or phenyl-lower-alkyl, wherein the phenyl group can optionally be substituted by one or more substituents selected from the group consisting of lower-alkyl, lower-alkoxy, fluorine, chlorine, bromine, CN, $CF_3$, $NO_2$, or $N(R^6,R^7)$, wherein $R^6$ and $R^7$ independently from each other are hydrogen or lower-alkyl, are another preferred embodiment of the present invention, with those compounds wherein $A^6$ is 4-trifluoromethyl-phenyl or 4-chloro-phenyl being particularly preferred.

Preferred compounds of general formula (I) are those selected from the group consisting of 1-{4-[6-(Allyl-methyl-amino)-hexyloxy]-phenyl}-3-(4-fluoro-3-trifluoromethyl-phenyl)-1-methyl-urea,
1-{4-[6-(Allyl-methyl-amino)-hexyloxy]-phenyl}-3-(2,4-difluoro-phenyl)-1-methyl-urea,
1-{4-[6-(Allyl-methyl-amino)-hexyloxy]-phenyl}-3-(2,4-dimethoxy-phenyl)-1-methyl-urea,
1-{4-[6-(Allyl-methyl-amino)-hexyloxy]-phenyl}-3-(4-fluoro-phenyl)-1-methyl-urea,
1-{4-[6-(Allyl-methyl-amino)-hexyloxy]-phenyl}-3-(4-methoxy-phenyl)-1-methyl-urea,
1-{4-[6-(Allyl-methyl-amino)-hexyloxy]-phenyl}-1-methyl-3-p-tolyl-urea,
1-{4-[6-(Allyl-methyl-amino)-hexyloxy]-phenyl}-3-(4-methoxy-2-methyl-phenyl)-1-methyl-urea,
1-{4-[6-(Allyl-methyl-amino)-hexyloxy]-phenyl}-3-(2,4-dimethyl-phenyl)-1-methyl-urea,
1-{4-[6-(Allyl-methyl-amino)-hexyloxy]-phenyl}-1-methyl-3-(3,4,5-trimethoxy-phenyl)-urea,
1-{4-[6-(Allyl-methyl-amino)-hexyloxy]-phenyl}-3-(3,4-dimethyl-phenyl)-1-methyl-urea,
3-(4-Acetyl-phenyl)-1-{4-[6-(allyl-methyl-amino)-hexyloxy]-phenyl}-1-methyl-urea,
1-{4-[6-(Allyl-methyl-amino)-hexyloxy],-phenyl}-3-(4-butyl-phenyl)-1-methyl-urea,
1-{4-[6-(Allyl-methyl-amino)-hexyloxy]-phenyl}-1-methyl-3-(4-methylsulfanyl-phenyl)-urea,
1-{4-[6-(Allyl-methyl-amino)-hexyloxy]-phenyl}-3-(4-isopropyl-phenyl)-1-methyl-urea,
1-{4-[6-(Allyl-methyl-amino)-hexyloxy]-phenyl}-3-(3,4-dichloro-phenyl)-1-methyl-urea,
1-{4-[6-(Allyl-methyl-amino)-hexyloxy]-phenyl}-3-(4-bromo-phenyl)-1-methyl-urea,
1-{4-[6-(Allyl-methyl-amino)-hexyloxy]-phenyl}-1-methyl-3-naphthalen-2-yl-urea,
1-{4-[6-(Allyl-methyl-amino)-hexyloxy]-phenyl}-1-methyl-3-naphthalen-1-yl-urea,
1-{4-[6-(Allyl-methyl-amino)-hexyloxy]-phenyl}-1-methyl-3-phenethyl-urea,
{4-[6-(Allyl-methyl-amino)-hexyloxy]-phenyl}-methyl-carbamic acid ethyl ester,
{4-[6-(Allyl-methyl-amino)-hexyloxy]-phenyl}-methyl-carbamic acid 9H-fluoren-9-ylmethyl ester,
{4-[6-(Allyl-methyl-amino)-hexyloxy]-phenyl}-methyl-carbamic acid 2,2,2-trichloro-1,1-dimethyl-ethyl ester,
{4-[6-(allyl-methyl-amino)-hexyloxy]-phenyl}-methyl-carbamic acid 4-nitro-phenyl ester",
{4-[6-(Allyl-methyl-amino)-hexyloxy]-phenyl}-methyl-carbamic acid isobutyl ester,
{4-[6-(Allyl-methyl-amino)-hexyloxy]-phenyl}-methyl-carbamic acid vinyl ester,
{4-[6-(Allyl-methyl-amino)-hexyloxy]-phenyl}-methyl-carbamic acid benzyl ester,
{4-[6-(Allyl-methyl-amino)-hexyloxy]-phenyl}-methyl-carbamic acid allyl ester,
{4-[6-(Allyl-methyl-amino)-hexyloxy]-phenyl}-methyl-carbamic acid phenyl ester,
{4-[6-(Allyl-methyl-amino)-hexyloxy]-phenyl}-methyl-carbamic acid butyl ester,
{4-(4-[6-(Allyl-methyl-amino)-hexyloxy]-phenyl}-methyl-carbamoyloxy)-benzoic acid methyl ester,
{4-[6-(Allyl-methyl-amino)-hexyloxy]-phenyl}-methyl-carbamic acid p-tolyl ester,
{4-[6-(Allyl-methyl-amino)-hexyloxy]-phenyl}-methyl-carbamic acid 4-bromo-phenyl ester,
{4-[6-(Allyl-methyl-amino)-hexyloxy]-phenyl}-methyl-carbamic acid 4-fluoro-phenyl ester,
{4-[6-(Allyl-methyl-amino)-hexyloxy]-phenyl}-methyl-carbamic acid 4-chloro-phenyl ester,
{4-[6-(Allyl-methyl-amino)-hexyloxy]-phenyl}-methyl-carbamic acid hexyl ester,
{4-[6-(Allyl-methyl-amino)-hexyloxy]-phenyl}-methyl-carbamic acid 4-methoxy-phenyl ester,
5-Chloro-thiophene-2-sulfonic acid {4-[6-(allyl-methyl-amino)-hexyloxy]-phenyl}-methyl-amide,
N-{4-[6-(Allyl-methyl-amino)-hexyloxy]-phenyl}-4,N-dimethyl-benzenesulfonamide,
Naphthalene-2-sulfonic acid {4-[6-(allyl-methyl-amino)-hexyloxy]-phenyl}-methyl-amide,
Quinoline-8-sulfonic acid {4-[6-(allyl-methyl-amino)-hexyloxy]-phenyl}-methyl-amide,
N-{4-[6-(Allyl-methyl-amino)-hexyloxy]-phenyl}-N-methyl-C-phenyl-methanesulfonamide,
3,5-Dimethyl-isoxazole-4-sulfonic acid {4-[6-(allyl-methyl-amino)-hexyloxy]-phenyl}-methyl-amide,
Naphthalene-1-sulfonic acid {4-[6-(allyl-methyl-amino)-hexyloxy]-phenyl}-methyl-amide,
N-{ 4-[6-(Allyl-methyl-amino)-hexyloxy]-phenyl}-4-methoxy-N-methyl-benzenesulfonamide,
N-{4-[6-(Allyl-methyl-amino)-hexyloxy]-phenyl}-N-methyl-benzenesulfonamide,
N-{4-[6-(Allyl-methyl-amino)-hexyloxy]-phenyl}-4-fluoro-N-methyl-benzenesulfonamide,
Thiophene-2-sulfonic acid {4-[6-(allyl-methyl-amino)-hexyloxy]-phenyl}-methyl-amide,
N-{4-[6-(Allyl-methyl-amino)-hexyloxy]-phenyl}-2-fluoro-N-methyl-benzenesulfonamide,
N-{4-[6-(Allyl-methyl-amino)-hexyloxy]-phenyl}-4-tert-butyl-N-methyl-benzenesulfonamide,
N-{4-[6-(Allyl-methyl-amino)-hexyloxy]-phenyl}-4-butoxy-N-methyl-benzenesulfonamide,
N-{4-[6-(Allyl-methyl-amino)-hexyloxy]-phenyl}-4-chloro-N-methyl-benzenesulfonamide,
N-{4-[6-(Allyl-methyl-amino)-hexyloxy]-phenyl}-N-methyl-4-trifluoromethyl-benzenesulfonamide,
N-{4-[6-(Allyl-methyl-amino)-hexyloxy]-phenyl}-4-bromo-N-methyl-benzenesulfonamide,
N-{4-[6-(Allyl-methyl-amino)-hexyloxy]-phenyl}-N-methyl-nicotinamide, 1H-Indole-2-carboxylic acid {4-[6-((allyl-methyl-amino)-hexyloxy]-phenyl}—methyl-namide, N-{4-[6-(Allyl-methyl-amino)-hexyloxy]-phenyl-methyl-benzamide,
N-{4-[6-(Allyl-methyl-amino)-hexyloxy]-phenyl}-4-chloro-N-methbenzamide,
N-{4-[6-(Allyl-methyl-amino)-hexyloxy]-phenyl}-4-fluoro-N-methyl-benzamide,
N-{4-[6-(Allyl-methyl-amino)-hexyloxy]-phenyl}-4-bromo-N-methyl-benzamide,
N-{4-[6-(Allyl-methyl-amino)-hexyloxy]-phenyl}-N-methyl-4-trifluoromethyl-benzamide,
Thiophene-3-carboxylic acid {4-[6-(allyl-methyl-amino)-hexyloxy]-phenyl}-methyl-amide,
5-Bromo-thiophene-2-carboxylic acid {4-[6-(allyl-methyl-amino)-hexyloxy]-phenyl}-methyl-amide,
N-{4-[6-(Allyl-methyl-amino)-hexyloxy]-phenyl}-N-methyl-2-thiophen-3-yl-acetamide,
N-{4-[6-(Allyl-methyl-amino)-hexyloxy]-phenyl}-2-(2,4-difluoro-phenyl)-N-methyl-acetamide,
5-Fluoro-1H-indole-2-carboxylic acid {4-[6-(allyl-methyl-amino)-hexyloxy]-phenyl}-methyl-amide,
N-{4-[6-(Allyl-methyl-amino)-hexyloxy]-phenyl}-2-(4-fluoro-phenyl)-N-methyl-acetamide,
1H-Indole-5-carboxylic acid {4-[6-(allyl- methyl-amino)-hexyloxy]-phenyl}-methyl-amid,
N-{4-[6-(Allyl-methyl-amino)-hexyloxy]-phenyl}-3-chloro-N-methyl-benzamide,
N-{4-[6-(Allyl-methyl-amino)-hexyloxy]-phenyl}-4-fluoro-3,N-dimethyl-benzamide,
N-{4-[6-(Allyl-methyl-amino)-hexyloxy]-phenyl}-N-methyl-4-nitro-benzamide,
N-{4-[6-(Allyl-methyl-amino)-hexyloxy]-phenyl}-4,N-dimethyl-benzamide,
N-{4-[6-(Allyl-methyl-amino)-hexyloxy]-phenyl}-3-cyano-N-methyl-benzamide,
N-{4-[6-(Allyl-methyl-amino)-hexyloxy]-phenyl}-3,N-dimethyl-benzamide,
N-{4-[6-(Allyl-methyl-amino)-hexyloxy]-phenyl}-3,4-dimethoxy-N-methyl-benzamide,
N-{4-[6-(Allyl-methyl-amino)-hexyloxy]-phenyl}-4-methoxy-N-methyl-benzamide,
N-{4-[6-(Allyl-methyl-amino)-hexyloxy]-phenyl}-4-fluoro-N-methyl-3-nitro-benzamide,
4-Acetyl-N-{4-[6-(allyl-methamino)-hexyloxy]-phenyl}-N-methyl-benzamide,
{4-[6-(Allyl-methyl-amino)-hexyloxy]-phenyl}-methyl-carbamic acid 4-acetylamino-phenyl ester,
{4-[6-(Allyl-methyl-amino)-hexyloxy]-phenyl}-methyl-carbamic acid 4-trifluoromethyl-phenyl ester,
Pyridine-2-carboxylic acid {4-[6-(allyl-methyl-amino)-hexyloxy]-phenyl}-methyl-amide,
N-[4-(6-Azepan-1-yl-hexyloxy)-phenyl]-4-bromo-N-methyl-benzenesulfonamide,
4-Bromo-N-(4-{6-[(2-methoxy-ethyl)-methyl-amino]-hexyloxy}-phenyl)-N-methyl-benzenesulfonamide,
4-Bromo-N-{4-[6-(ethyl-methyl-amino)-hexyloxy]-phenyl}-N-methyl-benzenesulfonamide,
4-Bromo-N-methyl-N-{4-[6-(2-methyl-piperidin-1-yl)-hexyloxy]-phenyl-benzenesulfonamide,
4-Bromo-N-(4-{6-[(2-hydroxy-ethyl)-methyl-amino]-hexyloxy}-phenyl)-N-methyl-benzenesulfonamide,
[(6-{4-[(4-Bromo-benzenesulfonyl)-methyl-amino]-phenoxy}-hexyl)-methyl-amino]-acetic acid ethyl ester,
4-Bromo-N-{4-[6-(butyl-methyl-amino)-hexyloxy]-phenyl}-N-methyl-benzenesulfonamide,
4-Bromo-N-[4-(6-diallylamino-hexyloxy)-phenyl]-N-methyl-benzenesulfonamide,
4-Bromo-N-methyl-N-[4-(6-pyrrolidin-1-yl-hexyloxy)-phenyl]-benzenesulfonamide,
4-Bromo-N-methyl-N-{4-[6-(methyl-prop-2-ynyl-amino)-hexyloxy]-phenyl}-benzenesulfonamide,
4-Bromo-N-methyl-N-[4-(6-piperidin-1-yl-hexyloxy)-phenyl]-benzenesulfonamide,
4-Bromo-N-{4-[6-(ethyl-isopropyl-amino)-hexyloxy]-phenyl}-N-methyl-benzenesulfonamide,
4-Bromo-N-methyl-N-[4-(6-morpholin-4-yl-hexyloxy)-phenyl]-benzenesulfonamide,
4-Bromo-N-{4-[6-(isopropyl-methyl-amino)-hexyloxy]-phenyl}-N-methyl-benzenesulfonamide,
4-Bromo-N-{4-[6-(3,6-dihydro-2H-pyridin-1-yl)-hexyloxy]-phenyl}-N-methyl-benzenesulfonamide,
4-Bromo-N-(4-{6-[ethyl-(2-hydroxy-ethyl)-amino]-hexyloxy}-phenyl)-N-methyl-benzenesulfonamide,
4-Bromo-N-[4-(6-dimethylamino-hexyloxy)-phenyl]-N-methyl-benzenesulfonamide,
4-Bromo-N-methyl-N-{4-[6-(methyl-propyl-amino)-hexyloxy]-phenyl}-benzenesulfonamide,
4-Bromo-N-{4-[6-(2,5-dihydro-pyrrol-1-yl)-hexyloxy]-phenyl}-N-methyl-benzenesulfonamide,
4-Bromo-N-[4-(6-diethylamino-hexyloxy)-phenyl]-N-methyl-benzenesulfonamide,
4-Bromo-N-methyl-N-[4-(6-thiomorpholin-4-yl-hexyloxy)-phenyl]-benzenesulfonamide,
4-Bromo-N-{4-[6-(butyl-ethyl-amino)-hexyloxy]-phenyl}-N-methyl-benzenesulfonamide,
4-Bromo-N-{4-[6-(4-hydroxy-piperidin-1-yl)-hexyloxy]-phenyl}-N-methyl-benzenesulfonamide,
4-Bromo-N-methyl-N-{4-[6-(4-methyl-piperazin-1-yl)-hexyloxy]-phenyl}-benzenesulfonamide,
4-Bromo-N-{4-[6-(3-hydroxy-piperidin-1-yl)-hexyloxy]-phenyl}-N-methyl-benzenesulfonamide,
4-Bromo-N-{4-[6-(3-dimethylamino-pyrrolidin-1-yl)-hexyloxy]-phenyl}-N-methyl-benzenesulfonamide,
4-Bromo-N-{4-[6-(4-hydroxymethyl-piperidin-1-yl)-hexyloxy]-phenyl}-N-methyl-benzenesulfonamide,
N-[4-(6-Azepan-1-yl-hexyloxy)-phenyl]-4-fluoro-N-methyl-benzenesulfonamide,
4-Fluoro-N-(4-{6-[(2-methoxy-ethyl)-methyl-amino]-hexyloxy}-phenyl)-N-methyl-benzenesulfonamide,
N-{4-[6-(Ethyl-methyl-amino)-hexyloxy]-phenyl}-4-fluoro-N-methyl-benzenesulfonamide,
4-Fluoro-N-methyl-N-{4-[6-(2-methyl-piperidin-1-yl)-hexyloxy]-phenyl}-benzenesulfonamide,
4-Fluoro-N-(4-{6-[(2-hydroxy-ethyl)-methyl-amino]-hexyloxy}-phenyl)-N-methyl-benzenesulfonamide,
[(6-{4-[(4-Fluoro-benzenesulfonyl)-methyl-amino]-phenoxy}-hexyl)-methyl-amino]-acetic acid ethyl ester,
N-{4-[6-(Butyl-methyl-amino)-hexyloxy]-phenyl}-4-fluoro-N-methyl-benzenesulfonamide,
N-[4-(6-Diallylamino-hexyloxy)-phenyl]-4-fluoro-N-methyl-benzenesulfonamide,
4-Fluoro-N-methyl-N-[4-(6-pyrrolidin-1-yl-hexyloxy)-phenyl]-benzenesulfonamide,
4-Fluoro-N-methyl-N-{4-[6-(methyl-prop-2-ynyl-amino)-hexyloxy]-phenyl}-benzenesulfonamide,
4-Fluoro-N-methyl-N-[4-(6-piperidin-1-yl-hexyloxy)-phenyl]-benzenesulfonamide,
N-{4-[6-(Ethyl-isopropyl-amino)-hexyloxy]-phenyl}-4-fluoro-N-methyl-benzenesulfonamide,
4-Fluoro-N-methyl-N-[4-(6-morpholin-4-yl-hexyloxy)-phenyl]-benzenesulfonamide,
4-Fluoro-N-{4-[6-(isopropyl-methyl-amino)-hexyloxy]-phenyl}-N-methyl-benzenesulfonamide,
N-{4-[6-(3,6-Dihydro-2H-pyridin-1-yl)-hexyloxy]-phenyl}-4-fluoro-N-methyl-benzenesulfonamide,
N-(4-{6-[Ethyl-(2-hydroxy-ethyl)-amino]-hexyloxy}-phenyl)-4-fluoro-N-methyl-benzenesulfonamide, N-[4-(6-Dimethylamino-hexyloxy)-phenyl]-4-fluoro-N-methyl-benzenesulfonamide,
4-Fluoro-N-methyl-N-{4-[6-(methyl-propyl-amino)-hexyloxy]-phenyl}-benzenesulfonamide,
N-{4-[6-(2,5-Dihydro-pyrrol-1-yl)-hexyloxy]-phenyl}-4-fluoro-N-methyl-benzenesulfonamide,
N-[4-(6-Diethylamino-hexyloxy)-phenyl]-4-fluoro-methyl-benzenesulfonamide,
4-Fluoro-N-methyl-N-[4-(6-thiomorpholin-4-yl-hexyloxy)-phenyl]-benzenesulfonamide,
N-{4-[6-(Butyl-ethyl-amino)-hexyloxy]-phenyl}-4-fluoro-N-methyl-benzenesulfonamide,
4-Fluoro-N-{4-[6-(4-hydroxy-piperidin-1-yl)-hexyloxy]-phenyl}-N-methyl-benzenesulfonamide,
4-Fluoro-N-methyl-N-{4-[6-(4-methyl-piperazin-1-yl)-hexyloxy]-phenyl}-benzenesulfonamide,
4-Fluoro-N-{4-[6-(3-hydroxy-piperidin-1-yl)-hexyloxy]-phenyl}-N-methyl-benzenesulfonamide,
4-Fluoro-N-{4-[6-(4-hydroxymethyl-piperidin-1-yl)-hexyloxy]-phenyl}-N-methyl-benzenesulfonamide,
N-[4-(6-Azepan-1-yl-hexyloxy)-phenyl],-4-chloro-N-methyl-benzenesulfonamide,
4-Chloro-N-(4-{6-[(2-methoxy-ethyl)-methyl-amino]-hexyloxy}-phenyl)-N-methyl-benzenesulfonamide,
4-Chloro-N-{4-[6-(ethyl-methyl-amino)-hexyloxy]-phenyl}-N-methyl-benzenesulfonamide,
4-Chloro-N-methyl-N-{4-[6-(2-methyl-piperidin-1-yl)-hexyloxy]-phenyl}-benzenesulfonamide,
4-Chloro-N-(4-{[6-(2-hydroxy-ethyl)-methyl-amino]-hexyloxy}-phenyl)-N-methyl-benzenesulfonamide,
[(6-{4-[(4-Chloro-benzenesulfonyl)-methyl-amino]-phenoxy}-hexyl)-methyl-amino]-acetic acid ethyl ester,
N-{4-[6-(Butyl-methyl-amino)-hexyloxy]-phenyl}-4-chloro-N-methyl-benzenesulfonamide,
4-Chloro-N-[4-(6-diallylamino-hexyloxy)-phenyl]-N-methyl-benzenesulfonamide,
4-Chloro-N-methyl-N-[4-(6-pyrrolidin-1-yl-hexyloxy)-phenyl]-benzenesulfonamide,
4-Chloro-N-methyl-N-{4-[6-(methyl-prop-2-ynyl-amino)-hexyloxy]-phenyl}-benzenesulfonamide,
4-Chloro-N-methyl-N-[4-(6-piperidin-1-yl-hexyloxy)-phenyl]-benzenesulfonamide,
4-Chloro-N-{4-[6-(ethyl-isopropyl-amino)-hexyloxy]-phenyl}-N-methyl-benzenesulfonamide,
4-Chloro-N-methyl-N-[4-(6-morpholin-4-yl-hexyloxy)-phenyl]-benzenesulfonamide,
4-Chloro-N-{4-[6-(isopropyl-methyl-amino)-hexyloxy]-phenyl}-N-methyl-benzenesulfonamide,
4-Chloro-N-{4-[6-(3,6-dihydro-2H-pyridin-1-yl)-hexyloxy]-phenyl}-N-methyl-benzenesulfonamide,
4-Chloro-N-(4-{6-[ethyl-(2-hydroxy-ethyl)-amino]-hexyloxy}-phenyl)-N-methyl-benzenesulfonamide,
4-Chloro-N-[4-(6-dimethylamino-hexyloxy)-phenyl]-N-methyl-benzenesulfonamide,
4-Chloro-N-methyl-N-{4-[6-(methyl-propyl-amino)-hexyloxy]-phenyl}-benzenesulfonamide,
4-Chloro-N-{4-[6-(2,5-dihydro-pyrrol-1-yl)-hexyloxy]-phenyl}-N-methyl-benzenesulfonamide,
4-Chloro-N-[4-(6-diethylamino-hexyloxy)-phenyl]-N-methyl-benzenesulfonamide,
4-Chloro-N-methyl-N-[4-(6-thiomorpholin-4-yl-hexyloxy)-phenyl]-benzenesulfonamide,
N-{4-[6-(Butyl-ethyl-amino)-hexyloxy]-phenyl}-4-chloro-N-methyl-benzenesulfonamide,
4-Chloro-N-{4-[6-(4-hydroxy-piperidin-1-yl)-hexyloxy]-phenyl}-N-methyl-benzenesulfonamide,
4-Chloro-N-methyl-N-{4-[6-(4-methyl-piperazin-1-yl)-hexyloxy]-phenyl}-benzenesulfonamide,
4-Chloro-N-{4-[6-(3-hydroxy-piperidin-1-yl)-hexyloxy]-phenyl}-N-methyl-benzenesulfonamide,
4-Chloro-N-{4-[6-(3-dimethylamino-pyrrolidin-1-yl)-hexyloxy]-phenyl}-N-methyl-benzenesulfonamide,
4-Chloro-N-{4-[6-(4-hydroxymethyl-piperidin-1-yl)-hexyloxy]-phenyl}-N-methyl-benzenesulfonamide,
N-[4-(6-Azepan-1-yl-hexyloxy)-phenyl]-N-methyl-4-trifluoromethyl-benzenesulfonamide,
N-(4-{6-[(2-Methoxy-ethyl)-methyl-amino]-hexyloxy}-phenyl)-N-methyl-4-trifluoromethyl-benzenesulfonamide,
N-{4-[6-(Ethyl-methyl-amino)-hexyloxy]-phenyl}-N-methyl-4-trifluoromethyl-benzenesulfonamide,
N-Methyl-N-{4-[6-(2-methyl-piperidin-1-yl)-hexyloxy]-phenyl}-4-trifluoromethyl-benzenesulfonamide,
N-(4-{6-[(2-Hydroxy-ethyl)-methyl-amino]-hexyloxy}-phenyl)-N-methyl-4-trifluoromethyl-benzenesulfonamide,
[Methyl-(6-{4-[methyl-(4-trifluoromethyl-benzenesulfonyl)-amino]-phenoxy}-hexyl)-amino]-acetic acid ethyl ester,
N-{4-[6-(Butyl-methyl-amino)-hexyloxy]-phenyl}-N-methyl-4-trifluoromethyl-benzenesulfonamide,
N-[4-(6-Diallylamino-hexyloxy)-phenyl]-N-methyl-4-trifluoromethyl-benzenesulfonamide,
N-Methyl-N-[4-(6-pyrrolidin-1-yl-hexyloxy)-phenyl]-4-trifluoromethyl-benzenesulfonamide,
N-Methyl-N-{4-[6-(methyl-pr2-ynyl-amino)-hexyloxy]-phenyl}-4-trifluoromethyl-benzenesulfonamide,
N-Methyl-N-[4-(6-piperidin-1-yl-hexyloxy)-phenyl]-4-trifluoromethyl-benzenesulfonamide,
N-{4-[6-(Ethyl-isopropyl-amino)-hexyloxy]-phenyl}-N-methyl-4-trifluoromethyl-benzenesulfonamide,
N-Methyl-N-[4-(6-morpholin-4-yl-hexyloxy)-phenyl]-4-trifluoromethyl-benzenesulfonamide,
N-{4-[6-(Isopropyl-methyl-amino)-hexyloxy]-phenyl}-N-methyl-4-trifluoromethyl-benzenesulfonamide,
N-{4-[6-(3,6-Dihydro-2H-pyridin-1-yl)-hexyloxy]-phenyl}-N-methyl-4-trifluoromethyl-benzenesulfonamide,
N-(4-{6-[Ethyl-(2-hydroxy-ethyl)-amino]-hexyloxy}-phenyl)-N-methyl-4-trifluoromethyl-benzenesulfonamide,
N-[4-(6-Dimethylamino-hexyloxy)-phenyl]-N-methyl-4-trifluoromethyl-benzenesulfonamide,
N-Methyl-N-{4-[6-(methyl-propyl-amino)-hexyloxy]-phenyl}-4-trifluoromethyl-benzenesulfonamide,
N-{4-[6-(2,5-Dihydro-pyrrol-1-yl)-hexyloxy]-phenyl}-N-methyl-4-trifluoromethyl-benzenesulfonamide,
N-[4-(6-Diethylamino-hexyloxy)-phenyl]-N-methyl-4-trifluoromethyl-benzenesulfonamide,
N-Methyl-N-[4-(6-thiomorpholin-4-yl-hexyloxy)-phenyl]-4-trifluoromethyl-benzenesulfonamide,
N-{4-[6-(Butyl-ethyl-amino)-hexyloxy]-phenyl}-N-methyl-4-trifluoromethyl-benzenesulfonamide,
N-{4-[6-(4-Hydroxy-piperidin-1-yl)-hexyloxy]-phenyl}-N-methyl-4-trifluoromethyl-benzenesulfonamide,
N-Methyl-N-{4-[6-(4-methyl-piperazin-1-yl)-hexyloxy]-phenyl}-4-trifluoromethyl-benzenesulfonamide,
N-{4-[6-(3-Hydroxy-piperidin-1-yl)-hexyloxy]-phenyl}-N-methyl-4-trifluoromethyl-benzenesulfonamide,
N-{4-[6-(3-Dimethylamino-pyrrolidin-1-yl)-hexyloxy]-phenyl}-N-methyl-4-trifluoromethyl-benzenesulfonamide,
N-{4-[6-(4-Hydroxymethyl-piperidin-1-yl)-hexyloxy]-phenyl}-N-methyl-4-trifluoromethyl-benzenesulfonamide, N-[4-(4-Dimethylamino-butoxy)-phenyl]-N-methyl-4-trifluoromethyl-benzenesulfonamide,
N-[4-(4-Dimethylamino-butoxy)-phenyl]-N-isopropyl-4-trifluoromethyl-benzenesulfonamide,
N-[4-(4-Dimethylamino-butoxy)-phenyl]-N-ethyl-4-trifluoromethyl-benzenesulfonamide,
N-[4-(5-Dimethylamino-pent-1-ynyl)-phenyl]-N-methyl-4-trifluoromethyl-benzenesulfonamide,
N-[4-(5-Dimethylamino-pentyl)-phenyl]]-N-methyl-4-trifluoromethyl-benzenesulfonamide,
N-[5-(5-Dimethylamino-pent-1-ynyl)-pyrimidin-2-yl]-N-methyl-4-trifluoromethyl-benzenesulfonamide,
[4-(5-Dimethylamino-pent-1-ynyl)-phenyl]-methyl-carbamic acid 4-chloro-phenyl ester,
N-[4-(4-Diethylamino-butoxy)-phenyl]-N-methyl-4-trifluoromethyl-benzenesulfonamide,
N-{4-[4-(Allyl-methyl-amino)-butoxy]-phenyl}-N-methyl-4-trifluoromethyl-benzenesulfonamide,
{4-[4-(Allyl-methyl-amino)-butoxy]-phenyl}-methyl-carbamic acid 4-chloro-phenyl ester,
[4-(4-Dimethylamino-butoxy)-phenyl]-methyl-carbamic acid 4-chloro-phenyl ester,
N-(4-{4-[Ethyl-(2-hydroxy-ethyl)-amino]-butoxy}-phenyl)-N-methyl-4-trifluoromethyl-benzenesulfonamide,
[4-(4-Diethylamino-butoxy)-phenyl]-methyl-carbamic acid 4-chloro-phenyl ester,
(4-{4-[Ethyl-(2-hydroxy-ethyl)-amino]-butoxy}-phenyl)-methyl-carbamic acid 4-chloro-phenyl ester,
4-[3-(Allyl-methyl-amino)-prop-1-ynyl]-phenyl}-methyl-carbamic acid 4-chloro-phenyl ester,
{4-[3-(Allyl-methyl-amino)-prop-1-ynyl]-phenyl}-methyl-carbamic acid 4-chloro-phenyl ester,
1-{4-[6-(Allyl-methyl-amino)-hexyloxy]-phenyl}-3-(2-bromo-4-fluoro-phenyl)-1-methyl-thiourea,
1-{4-[6-(Allyl-methyl-amino)-hexyloxy]-phenyl}-3-(4-bromo-2-methyl-phenyl)-1-methyl-thiourea,
1-{4-[6-(Allyl-methyl-amino)-hexyloxy]-phenyl}-1-methyl-3-(4-trifluoromethyl-phenyl)-thiourea,
1-{4-[6-(Allyl-methyl-amino)-hexyloxy]-phenyl}-3-(4-chloro-phenyl)-1-methyl-thiourea,
1-{4-[6-(Allyl-methyl-amino)-hexyloxy]-phenyl}-3-(4-methoxy-phenyl)-1-methyl-thiourea,
1-{4-[6-(Allyl-methyl-amino)-hexyloxy]-phenyl}-3-(4-cyano-phenyl)-1-methyl-thiourea,
1-{4-[6-(Allyl-methyl-amino)-hexyloxy]-phenyl}-1-methyl-3-(3-methyl-butyl)-thiourea,
1-{4-[6-(Allyl-methyl-amino)-hexyloxy]-phenyl}-3-sec-butyl-1-methyl-thiourea,
1-{4-[6-(Allyl-methyl-amino)-hexyloxy]-phenyl}-3-cyclopropyl-1-methyl-thiourea,
1-{4-[6-(Allyl-methyl-amino)-hexyloxy]-phenyl}-3-(2,4-dichloro-benzyl)-1-methyl-thiourea,
1-{4-[6-(Allyl-methyl-amino)-hexyloxy]-phenyl}-3-(5-chloro-2-methoxy-phenyl)-1-methyl-thiourea,
1-{4-[6-(allyl-methyl-amino)-hexyloxy]-phenyl}-1-methyl-3-(2-methyl-5-nitro-phenyl)-thiourea,
1-{4-[6-(Allyl-methyl-amino)-hexyloxy]-phenyl}-3-(2,3-dihydro-benzo[1,4]dioxin-6-yl)-1-methyl-thiourea,
1-{4-[6-(Allyl-methyl-amino)-hexyloxy]-phenyl}-3-(2-isopropyl-phenyl)-1-methyl-thiourea,
1-{4-[6-(Allyl-methyl-amino)-hexyloxy]-phenyl}-1-methyl-3-(3-phenyl-propyl)-thiourea,
3-(4-Acetyl-phenyl)-1-{4-[6-(allyl-methyl-amino)-hexyloxy]-phenyl}-1-methyl-thiourea,
1-{4-[6-(Allyl-methyl-amino)-hexyloxy]-phenyl}-3-cyclohexylmethyl-1-methyl-thiourea,
1-{4-[6-(Allyl-methyl-amino)-hexyloxy]-phenyl}-1-methyl-3-(tetrahydro-furan-2-ylmethyl)-thiourea,
1-{4-[6-(Allyl-methyl-amino)-hexyloxy]-phenyl}-3-fran-2-ylmetyl-1-methyl-thiourea,
1-{4-[6-(Allyl-methyl-amino)-hexyloxy]-phenyl}-3-cyfopentyl-1-methyl-thiourea,
{4-[6-(Allyl-methyl-amino)-hexyloxy]-phenyl}-3-bicyclo[2.2]hept-2-yl-1-methyl-thiourea,
1-{4-[6-(Allyl-methyl-amino)-hexyloxy]-phenyl}-3-methyl3-(2,3,5,6-tetrafluoro-phenyl)-thiourea,
1-{4-[6-(Allyl-methyl-amino)-hexyloxy]-phenyl}-3-[1-(4-fluoro-phenyl)-ethyl]-1-methyl-thiourea,
1-{4-[6-(Allyl-methyl-amino)-hexyloxy]-phenyl}-3-(4-tert-butyl-phenyl)-e 1-methyl-thiourea,
1-{4-[6-(Allyl-methyl-amino)-hexyloxy]-phenyl}-1-methyl-3-(2,3,4-trimethoxy-benzyl)-thiourea,
1-{4-[6-(Allyl-methyl-amino)-hexyloxy]-phenyl}-3-(3-chloro-4-methyl-benzyl)-1-methyl-thiourea,
1-{4-[6-(Allyl-methyl-amino)-hexyloxy]-phenyl}-1-methyl-3-pyridin-3-yl-thiourea,
1-{4-[6-(Allyl-methyl-amino)-hexyloxy]-phenyl}-3-benzo[1,3]dioxol-5-ylmethyl-1-methyl-thiourea,
1-{4-[6-(Allyl-methyl-amino)-hexyloxy]-phenyl}-1-methyl-3-(4-methylsulfanyl-phenyl)-thiourea,
1-{4-[6-(Allyl-methyl-amino)-hexyloxy]-phenyl}-3-cycloheptyl-1-methyl-thiourea,
1-{4-[6-(Allyl-methyl-amino)-hexyloxy]-phenyl}-3-(2-chloro-5-trifluoromethyl-phenyl)-1-methyl-thiourea,
1-{4-[6-(Allyl-methyl-amino)-hexyloxy]-phenyl}-1-methyl-3-naphthalen-1-yl-thiourea,
1–14-[6-(Allyl-methyl-amino)-hexyloxy]-phenyl}-3-(2-cyclohex-1-enyl-ethyl)-1-methyl-thiourea,
(3-{4-[6-(Allyl-methyl-amino)-hexyloxy]-phenyl}-3-methyl-thioureido-acetic acid methyl ester,
1-{4-[6-(Allyl-methyl-amino)-hexyloxy]-phenyl}-3-ethyl-1-methyl-thiourea,
1-{4-[6-(Allyl-methyl-amino)-hexyloxy]-phenyl}-3-hexyl-1-methyl-thiourea,
1-{4-[6-(Allyl-methyl-amino)-hexyloxy]-phenyl}-3-butyl-1-methyl-thiourea,
1-{4-[6-(Allyl-methyl-amino)-hexyloxy]-phenyl-methyl-3-(2-methyl-butyl)-thiourea,
1-{4-[6-(Allyl-methyl-amino)-hexyloxy]-phenyl}-3-(2-methoxy-ethyl)-1-methyl-thiourea,
1-{4-[6-(Allyl-methyl-amino)-hexyloxy]-phenyl}-1-methyl-3-(3-methyl-butyl)-thiourea,
1-{4-[6-(Allyl-methyl-amino)-hexyloxy]-phenyl}-1-methyl-3-phenyl-thiourea,
4-(3-{4-[6-(Allyl-methyl-amino)-hexyloxy]-phenyl}-3-methyl-thioureido-benzoic acid methyl ester,
1-{4-[6-(Allyl-methyl-amino)-hexyloxy]-phenyl}-3-(4-butyl-phenyl)-1-methyl-thiourea,
1-{4-[6-(Allyl-methyl-amino)-hexyloxy]-pheny3-benzyl-1-methyl-thiourea,
1-{4-[6-(Allyl-methyl-amino)-hexyloxy]-phenyl}-1-methyl-3-(4-methyl-benzyl)-thiourea,
1-{4-[6-(Allyl-methyl-amino)-hexyloxy]-phenyl}-3-(4-methoxy-benzyl)-1-methyl-thiourea,
1-{4-[6-(Allyl-methyl-amino)-hexyloxy]-phenyl}-3-(4-fluoro-benzyl)-1-methyl-thiourea,
1-{4-[6-(Allyl-methyl-amino)-hexyloxy]-phenyl}-3-(4-chloro-benzyl)-1-methyl-thiourea,
1-{4-[6-(Allyl-methyl-amino)-hexyloxy]-phenyl}-1-methyl-3-(1-phenyl-ethyl)-thiourea,
1-{4-[6-(Allyl-methyl-amino)-hexyloxy]-phenyl}-3-[2-(4-chloro-phenyl)-ethyl]-1-methyl-thiourea,
1-{4-[6-(Allyl-methyl-amino)-hexyloxy]-phenyl}-1-methyl-3-phenethyl-thiourea, 1-{4-[6-(Allyl-methyl-amino)-hexyloxy]-phenyl}-1-methyl-3-(2-p-tolyl-ethyl)-thiourea,
1-{4-[6-(Allyl-methyl-amino)-hexyloxy]-phenyl}-3-cyclohexyl-1-methyl-thiourea,
{4-[6-(Allyl-methyl-amino)-hexyloxy]-phenyl}-methyl-thiocarbamic acid O-(4-chloro-phenyl) ester,
{4-[6-(Allyl-methyl-amino)-hexyloxy]-phenyl}-methyl-thiocarbamic acid O-pentafluorophenyl ester,
{4-[6-(Allyl-methyl-amino)-hexyloxy]-phenyl}-methyl-thiocarbamic acid O-(2,4,6-trichloro-phenyl)ester,
{4-[6-(Allyl-methyl-amino)-hexyloxy]-phenyl}-methyl-thiocarbamic acid O-(4-fluoro-phenyl)ester,
{4-[6-(Allyl-methyl-amino)-hexyloxy]-phenyl}-methyl-sulfamic acid benzyl amide,
{4-[6-(Allyl-methyl-amino)-hexyloxy]-phenyl}-methyl-sulfamic acid phenyl amide,
{4-[6-(Allyl-methyl-amino)-hexyloxy]-phenyl}-methyl-sulfamic acid furan-2-ylmethyl amide,
({4-[6-(Allyl-methyl-amino)-hexyloxy]-phenyl}-methyl-sulfonylamino)-acetic acid ethyl ester,
{4-[6-(Allyl-methyl-amino)-hexyloxy]-phenyl}-methyl-sulfamic acid 2,2,2-trifluoro-ethyl amide,
{4-[6-(Allyl-methyl-amino)-hexyloxy]-phenyl}-methyl-sulfamic acid benzo[1,3]dioxol-5-ylmethyl amide,
4-[6-(Allyl-methyl-amino)-hexyloxy]-phenyl}-methyl-sulfamic acid phenethyl amide,
4-[6-(Allyl-methyl-amino)-hexyloxy]-phenyl}-methyl-sulfamic acid cycopropyl amide,
{4-[6-(Allyl-methyl-amino)-hexyloxy]-phenyl}-methyl-sulfamic acid 2,2,2-trifluoro-ethyl amide,
{4-[6-(Allyl-methyl-amino)-hexyloxy]-phenyl}-methyl-sulfamic acid 4-chloro-phenyl amide,
{4-[6-(Allyl-methyl-amino)-hexyloxy]-phenyl}-methyl-sulfamic acid 4-bromo-phenyl amide,
{4-[6-(Allyl-methyl-amino)-hexyloxy]-phenyl}-methyl-sulfamic acid p-tolyl amide,
{4-[6-(Allyl-methyl-amino)-hexyloxy]-phenyl}-methyl-sulfamic acid 4-trifluoromethyl-phenyl amide,
{4-[6-(Allyl-methyl-amino)-hexyloxy]-phenyl}-methyl-sulfamic acid 4-cyano-phenyl amide,
{4-[6-(Allyl-methyl-amino)-hexyloxy]-phenyl}-methyl-sulfamic acid 4-methoxy-phenyl amide,
{4-[6-(Allyl-methyl-amino)-hexyloxy]-phenyl}-methyl-sulfamic acid 4-fluoro-phenyl amide,
{4-[6-(Allyl-methyl-amino)-hexyloxy]-phenyl}-methyl-sulfamic acid 3,4-difluoro-phenyl amide,
{4-[6-(Allyl-methyl-amino)-hexyloxy]-phenyl}-methyl-sulfamic acid 3-fluoro-phenyl amide,
{4-[6-(Allyl-methyl-amino)-hexyloxy]-phenyl}-methyl-sulfamic acid 2,4-difluoro-phenyl amide,
{4-[6-(Allyl-methyl-amino)-hexyloxy]-phenyl}-methyl-sulfamic acid 2,5-difluoro-phenyl amide,
{4-[5-(Allyl-methyl-amino)-pentyloxy]-phenyl}-methyl-sulfamic acid (4-chloro-phenyl)-amide,
{4-[4-(Allyl-methyl-amino)-butoxy]-phenyl}-methyl-sulfamic acid (4-chloro-phenyl)-amide,
{4-[5-(Allyl-methyl-amino)-pentyloxy]-phenyl}-methyl-sulfamic acid (4-fluoro-phenyl)-amide,
{4-[4-(Allyl-methyl-amino)—butoxy]-phenyl}-methyl-sulfamic acid (4-fluoro-phenyl)-amide,
{4-[5-(Allyl-methyl-amino)-pentyloxy]-phenyl}-methyl-sulfamic acid (4-bromo-phenyl)-amide,
{4-[4-(Allyl-methyl-amino)-butoxy]-phenyl}-methyl-sulfamic acid (4-bromo-phenyl)-amide,
{4-[5-(Allyl-methyl-amino)-pentyloxy]-phenyl}-methyl-sulfamic acid p-tolyl-amide,
{4-[4-(Allyl-methyl-amino)-butoxy]-phenyl}-methyl-sulfamic acid (p-tolyl)-amide,
{4-[5-(Allyl-methyl-amino)-pentyloxy]-phenyl}-methyl-sulfamic acid (3,4-difluoro-phenyl)-amide,
{4-[4-(Allyl-methyl-amino)-butoxy]-phenyl}-methyl-sulfamic acid (3,4-difluoro-phenyl)-amide,
{4-[5-(Allyl-methyl-amino)-pentyloxy]-phenyl}-methyl-sulfamic acid (4-trifluoromethyl-phenyl)-amide,
{4-[4-(Allyl-methyl-amino)-butoxy]-phenyl}-methyl-sulfamic acid (4-trifluoromethyl-phenyl)-amide,
{4-[4-(Allyl-methyl-amino)-butoxy]-phenyl}-methyl-sulfamic acid (3-fluoro-phenyl)-amide,
{4-[5-(Allyl-methyl-amino)-pentyloxy]-phenyl}-methyl-sulfamic acid (4-cyano-phenyl)-amide,
{4-[4-(Allyl-methyl-amino)-butoxy]-phenyl}-methyl-sulfamic acid (4-cyano-phenyl)-amide,
{4-[5-(Allyl-methyl-amino)-pentyloxy]-phenyl}-methyl-sulfamic acid (2,4-difluoro-phenyl)-amide,
{4-[4-(Allyl-methyl-amino)-butoxy]-phenyl}-methyl-sulfamic acid (2,4-difluoro-phenyl)-amide,
{4-[5-(Allyl-methyl-amino)-pentyloxy]-phenyl}-methyl-sulfamic acid (4-methoxy-phenyl)-amide,
{4-[4-(Allyl-methyl-amino)-butoxy]-phenyl}-methyl-sulfamic acid (4-methoxy-phenyl)-amide,
{4-[5-(Allyl-methyl-amino)-pentyloxy]-phenyl}-methyl-sulfamic acid (2,5-difluoro-phenyl)-amide,
{4-[4-(Allyl-methyl-amino)-butoxy]-phenyl}-methyl-sulfamic acid (2,5-difluoro-phenyl)-amide,
{4-[5-(Allyl-methyl-amino)-pentyloxy]-phenyl}-methyl-sulfamic acid (phenyl)-amide,
and {4-[4-(Allyl-methyl-amino)-butoxy]-phenyl}-methyl-sulfamic acid (phenyl)-amide, and
pharmaceutically acceptable salts thereof.

Particularly preferred compounds of general formula (I) are those selected from the group consisting of {4-[4-(Allyl-methyl-amino)-butoxy]-phenyl}-methyl-carbamic acid 4-chloro-phenyl ester,
N-{4-[4-(Allyl-methyl-amino)-butoxy]-phenyl}-N-methyl-4-trifluoromethyl-benzenesulfonamide,
N-[4-(4-Dimethylamino-butoxy)-phenyl]-N-methyl-4-trifluoromethyl-benzenesulfonamide,
N-[4-(4-Diethylamino-butoxy)-phenyl]-N-methyl-4-trifluoromethyl-benzenesulfonamide,
[4-(5-Dimethylamino-pent-1-ynyl)-phenyl]-methyl-carbamic acid 4-chloro-phenyl ester,
[4-(4-Diethylamino-butoxy)-phenyl]-methyl- carbamic acid 4- chloro-phenyl ester,
(4-{ 4-[Ethyl-(2-hydroxy- ethyl)-amino]-butoxy}-phenyl)-methyl- carbamic acid 4-chloro-phenyl ester,
[4-(4-Dimethylamino-butoxy)-phenyl]-methyl-carbamic acid 4-chloro-phenyl ester,
N-(4-{4-[Ethyl-(2-hydroxy-ethyl)-amino]-butoxy}-phenyl)-N-methyl-4-trifluoromethyl-benzenesulfonamide,
N-[4-(4-Dimethylamino-butoxy)-phenyl]-N-ethyl-4-trifluoromethyl-benzenesulfonamide, and
1-{4-[6-(Allyl-methyl-amino)-hexyloxy]-phenyl}-3-(4-chloro-phenyl)-1-methyl-thiourea,
and pharmaceutically acceptable salts thereof.

Compounds of formula (I) can have one or more asymmetric carbon atoms and can exist in the form of optically pure enantiomers or as racemats. The invention embraces all of these forms.

It will be appreciated, that the compounds of general formula (I) in this invention may be derivatised at functional groups to provide derivatives which are capable of conversion back to the parent compound in vivo.

The present invention also relates to a process for the manufacture of compounds as described above, which process comprises reacting a compound of formula (II)

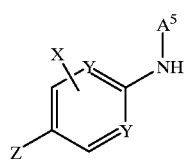
(II)

wherein

X, Y, $A^5$ have the significances given above,
Z is a group $(A^1,A^2)N—C(A^3,A^4)—L—V—$, halogen—$CH_2—L—V—$, or halogen, wherein $A^1, A^2, A^3, A^4$, L and V have the significances given above,
or Z is P—V— wherein V is O, S, or $NR^6$, P is a protecting group and $R^6$ is as defined above,
with $ClSO_2—A^6$, $ClCOO—A^6$, $ClCSO—A^6$, $OCN—A^6$, $SCN—A^6$, $HOOC—A^6$, or $ClSO_2A6$,
wherein $A^6$ is as defined above.

In processes as described above wherein Z is halogen —$CH_2—L—V—$, the term "halogen" preferrably refers to bromine. In processes as described above wherein Z is halogen, the term "halogen" preferrably refers to bromine or iodine.

The invention further relates to compounds of formula (I) as defined above, when manufactured according to a process as defined above.

As described above, the compounds of formula (I) of the present invention can be used for the treatment and/or prophylaxis of diseases which are associated with OSC such as hypercholesterolemia, hyperlipemia, arteriosclerosis, vascular diseases, mycoses, parasite infections and gallstones, and/or treatment and/or prophylaxis of impaired glucose tolerance, diabetes, tumors and/or hyperproliferative disorders, preferably for the treatment and/or prophylaxis of hypercholesterolemia and/or hyperlipemia. Hyperproliferative skin and vascular disorders particularly come into consideration as hyperproliferative disorders.

The invention therefore also relates to pharmaceutical compositions comprising a compound as defined above and a pharmaceutically acceptable carrier and/or adjuvant.

Further, the invention relates to compounds as defined above for use as therapeutic active substances, particularly as therapeutic active substances for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In another embodiment, the invention relates to a method for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia, which method comprises administering a compound as defined above to a human being or animal.

The invention further relates to the use of compounds as defined above for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia.

In addition, the invention relates to the use of compounds as defined above for the preparation of medicaments for the treatment and/or prophylaxis of diseases which are associated with OSC such as hypercholesterolemia, hyperlipemia, arteriosclerosis, vascular diseases, mycoses, parasite infections, gallstones, tumors and/or hyperproliferative disorders, and/or treatment and/or prophylaxis of impaired glucose tolerance and diabetes, preferably for the treatment and/or prophylaxis of hypercholesterolemia and/or hyperlipemia. Such medicaments comprise a compound as defined above.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given in the examples or by methods known in the art.

Compounds of formula (I), in which V represents O, $NR^6$ or S and Y represents C can be prepared by the method outlined in scheme 1. In scheme 2, the preparation of compounds of formula (I), in which V represents —$CH_2$—, —CH=CH— or —C≡C— and Y is C is outlined. Scheme 3 shows an overview of the preparation of compounds of formula (I) in which V represents —$CH_2$—, —CH=CH— or —C≡C— and Y is N.

Scheme 1

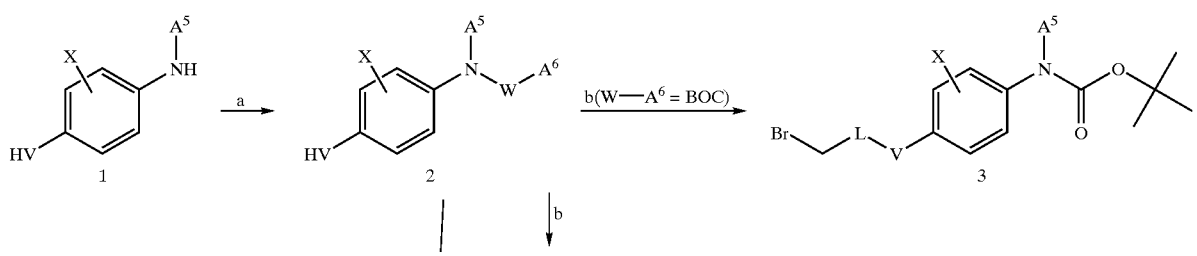

-continued
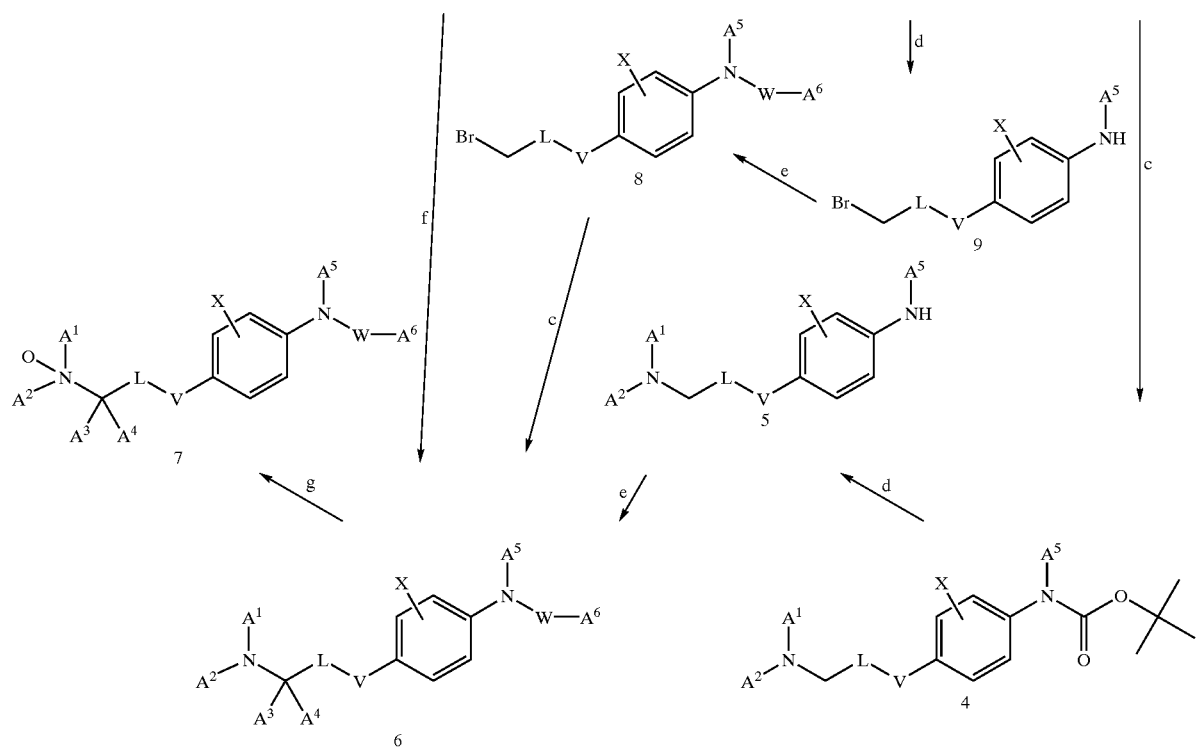
Scheme 2
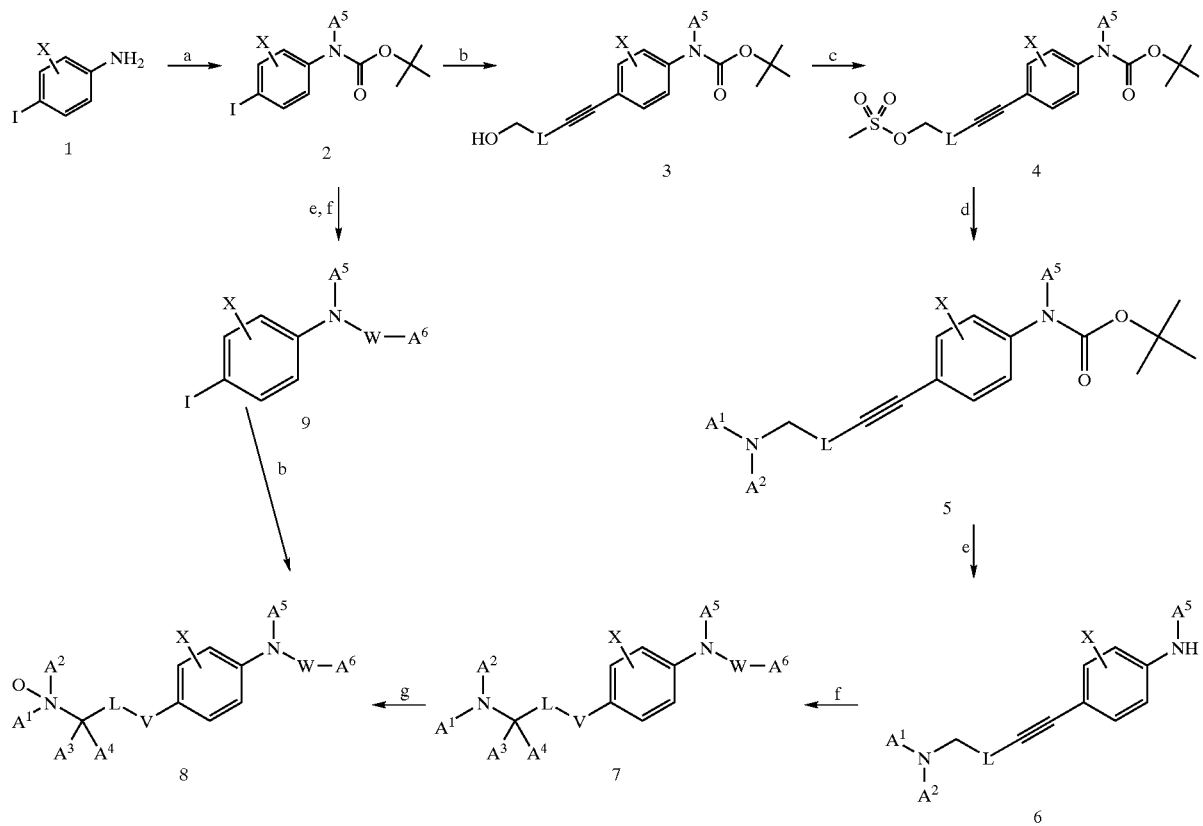

Scheme 3

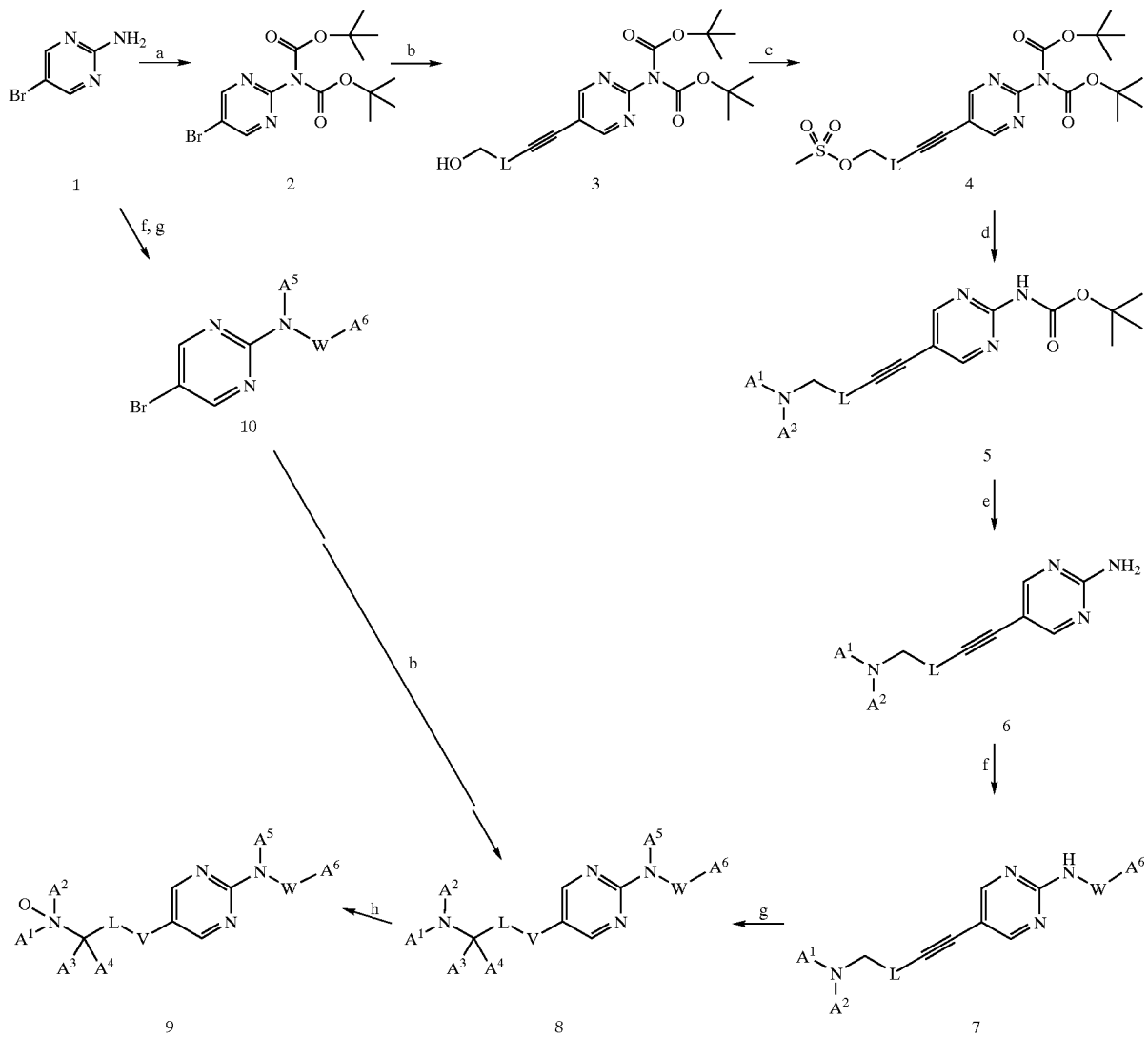

In scheme 1, the synthesis is described for an 4-alkylaminobenzene-VH and 4-aminobenzene-VH, such as 4-alkylaminophenol, 4-aminophenol, 4-alkylamino-benzenethiol, 4-amino-benzenethiol or monoprotected 1,4-benzene-diamine, all possibly substituted by a group X. The 4-aminobenzene-VH are commercial available, the 4-alkylaminobenzene-VH are also commercially available or are synthesized by known procedures. 4-Alkyl-sidechain can alternatively be introduced in a later stage of the synthesis.

N-alkyl-p-anisidine is deprotected for example with 62% aqueous HBr in acetic acid at 110° C. The resulting 4-alkylamino-phenol 1 as an example is then N-BOC-protected (reaction step a) in THF/acetonitril with pyridine (if the aminophenol is a salt) and di-tert-butyl dicarbonate at 70° C. Alkylation of the (4-Hydroxy-phenyl)-alkyl-carbamic acid tert-butyl ester in acetone with $K_2CO_3$ and a suitable dihaloalkane, dihaloalkene, or a N-protected diha-loalkylaminoalkane (halogene is here represented by bromine, but can be also Cl or I. It is also possible to use mesylates or tosylates instead of halogenides) at reflux yields halogenide 3 (reaction step b). This compound is then converted (reaction step c) to the amine 4 in DMA at RT with an excess of the corresponding amine. Boc deprotection (reaction step d) in $CH_2Cl_2$ at −20° C. with TFA, following by warming up to room temperature yields the alkyl-aniline 5. This intermediate compound is then converted to the compounds of the present invention 6 by one of the following reactions (step e):

Sulfonylation of compounds 5 is done in dioxane with Huinigsbase and a sulfonyl chloride over night at RT to give the sulfonamide 6. N-alkylation (in case $A^5$=H) under Mitsunobu-conditions in THF with DEAD and the corresponding alcohol results in the final product 6 as a free amine.

Compounds 5 may be reacted with $A^6OCOCl$/Huenigsbase in dioxane or $A^6OH/Cl_3COCl$/quinoline (formation of the chloroformate) may be reacted with compound 5 and Huenigsbase.

Compounds 5 may be reacted with $A^6OCSCl$ in dioxane.

Compounds 5 may be reacted with isocyanate in dioxane at room temperature.

Compounds 5 may be reacted with isothiocyanate in dioxane at room temperature.

Compounds 5 may be reacted with A⁶COOH/EDCI/DMAP (with anhydride formation, and subsequent addition of the starting amine at −10° C. to room temperature) or as alternative with A⁶COOH/EDCI/DMAP or A⁶COOH/Huenigsbase/EDCI/HOBT in DMF, dioxane or $CH_2Cl_2$ at room temperature.

Compounds 5 may be reacted with sulfamoyl chlorides in dioxane in the presence of an excess of triethylamine to give sulfamide 6. The sulfamoyl chlorides are synthesized from A⁶NH₂ and chiorosulfonic acid in $CH_2Cl_2$ at 0° C. to room temperature followed by reaction with $PCl_5$ in toluene at 75° C. Alternatively, the sulfamoyl chlorides can be synthesized in acetonitrile with A⁶NH₂ and sulfuryl chloride at 0° C. to 65° C.

Alternatively, the group A¹A²NC(A³A⁴)L—OH or the mesylate/halogenide of them can be synthesized by known methods and attached to compound 2 (Mitsunobu or alkylating conditions), to give directly amine 6 (reaction step f).

The amines 6 can optionally be converted to a salt or to the N-oxide 7 (reaction of compounds 6 with a mixture of hydrogen peroxid urea adduct and phthalic anhydride in $CH_2Cl_2$ at RT, reaction step g).

Another strategy outlined in scheme 1 is the introduction of the desired group —W—A⁶ in compound 1. The 4-alkylaminophenol salt (e.g. hemisulfate) or another suitable compound as described above is persilylated (reflux in hexamethyldisilazane and evaporated) and reacted with a suitable sulfonyl chloride or chloroformate or is transformed in analogy to reaction step e as described above. Aqueous work-up (deprotection of the V-Silylprotection) yields compound 2.Alkylation of 2 with for example dihaloalkane in DMF with NaH as base yields halogenide 8 (reaction step b). Amination of the halogenide 8 as described above yields the final compound 6, which can optionally be transformed to salts or to the N-oxide 7.

A third possibility which is described in Scheme 1 is the deprotection of Boc-protected compound 3 (in $CH_2Cl_2$ at 0° C. to RT with TFA during 20 min) which yields compound 9. With this compound, introduction of the W—A⁶ group (which yields compound 8 in analogy to reaction step e as described above) followed by amination to the final compound 6 (reaction step c) as described above is also possible.

In scheme 2, the preparation of compounds of formula (I), in which V represents —$CH_2$—, —CH=CH— or —C≡C— and Y is C is outlined starting from 4-Iodoaniline I as an example, which is BOC-protected with di-tert-butyl dicarbonate in THF for 30 h at 80° C. and N-alkylated with A⁵-halogenide in THF at −18° C. to RT with 55% NaH as base to yield compound 2 (reaction step a). Sonogashira-coupling (reaction step b) of the iodo-aniline derivative 2 and a suitable alkinol in piperidine with $Pd(PPh_3)_4$/CuI at 45° C. to 80° C. in analogy to a literature procedure [Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649–672.]yields alcohol 3. Mesylation with methanesulfonylchloride/pyridine/DMAP (reaction step c) and subsequent amination (reaction step d) of the resulting mesylate 4 with a suitable amine in DMA at RT yields the amine 5. Boc-deprotection of 5 (reaction step e) in $CH_2Cl_2$ at a temperature between 0° C. and RT with TFA during 20 min yields te aniline derivative 6. This intermediate compound is then converted to the compounds of the present invention 7 by introduction of the desired W—A⁶ group (reaction step f) in analogy to the methods described above in context with scheme 1.

Optionally the alkine side chain can be hydrogenated in MeOH/dioxane/AcOH with $Pd/C_{10}$% and hydrogene at 1 atm (reaction step g) to yield the corresponding saturated compound 7 in which V is —$CH_2$—.

Alternatively compound 2 can be BOC-deprotected and the desired W—A⁶ group can be introduced as described above (reaction steps e, f) to yield compound 9. The group A¹A²NC(A³A⁴)L-acethylene can then be synthesized by known methods (see for example Imada, Yasushi; Yuasa, Mari; Nakamura, Ishin; Murahashi, Shun-Ichi. Copper(I)-Catalyzed Amination of Propargyl Esters. Selective Synthesis of Propargylamines, 1-Alken-3-ylamines, and (Z)-Allylamines. J. Org. Chem. (1994), 59(9), 2282–4) and attached to compound 9 (Sonogashira-coupling), to yield the compounds of the present invention 7 (reaction step b).

The compounds 7 can optionally be converted to a salt or to the N-oxide 8 (reaction of compounds 7 with a mixture of hydrogen peoxid urea adduct and phthalic anhydride in $CH_2Cl_2$ at RT, reaction step g).

Scheme 3 shows an overview of the preparation of compounds of formula (I) in which V represents —$CH_2$—, —CH=CH— or —C≡C— and Y is N. As an example, BOC-protection of 2-amino-5-bromopyrimdine 1 with di-tert-butyl dicarbonate in THF/$CH_3CN$ with pyridine/DMAP at a temperature between RT and 80° C. yields the di-BOC-pyrimidine 2 (reaction step a). Sonogashira-coupling of compound 2 with a suitable alkinol in DMF with $Et_3N$, CuI $PdCl_2(dppf).CH_2Cl_2$ at 80° C. in analogy to a literature procedure [The synthesis followed a procedure of Arco Y. Jeng; Design and Synthesis of Potent, Selective Inhibitors of Endothelin-Converting Enzyme, Journal of Medicinal Chemistry; 1998; 41(9); 1513–1523.] yields alcohol 3 (reaction step b). Mesylation with methanesulfonylchloride/pyridine/DMAP (reaction step c) and subsequent amination (reaction step d) of the resulting mesylate 4 with a suitable amine in DMA at RT yields the amine 5. Compound 6 is obtained after Boc-deprotection in $CH_2Cl_2$ at 0° C. to RT with TFA during 20 min (reaction step e). Sulfonylation of compound 6 with a suitable sulfonyl chloride in pyridine at 70° C. overnight (reaction step f) yields compound 7 which is N-alkylated under Mitsunobu-conditions with triphenylphosphine/DEAD/alkanol in THF at 0° C. to RT (reaction step g) to yield the compounds of the present invention 8.

Alternatively compounds 10 with suitable W—A⁶ and A⁵ groups can be synthesized in analogy to the methods as described above (reaction steps f,g). Other residues A¹A²NC(A³A⁴)L-acethylene can be synthesized by known methods (see for example Imada, Yasushi; Yuasa, Mari; Nakamura, Ishin; Murahashi, Shun-Ichi. Copper(I)-Catalyzed Amination of Propargyl Esters. Selective Synthesis of Propargylamines, 1-Alken-3-ylamines, and (Z)-Allylamines. J. Org. Chem. (1994), 59(9), 2282–4) and attached to compounds 10 (Sonogashira-coupling), to yield the compounds 8 (reaction step b) in analogy to the methods described above.

The compounds 8 can optionally be converted to a salt or to the N-oxide 9 (reaction step h) by the methods described above.

The following tests were carried out in order to determine the activity of the compounds of formula I and their salts.

Inhibition of Human Liver Microsomal 2,3-oxidosqualene-lanosterol Cyclase (OSC)

Liver microsomes from a healthy volunteer were prepared in sodium phosphate buffer (pH 7.4). The OSC activity was measured in the same buffer, which also contained 1 mM EDTA and 1 mM dithiothreitol. The microsomes were diluted to 0.8 mg/ml protein in cold phosphate buffer. Dry [$^{14}$C]R,S-monooxidosqualene (MOS, 12.8 mCi/mmol) was diluted to 20 nCi/µl with ethanol and mixed with phosphate buffer—1% BSA (bovine serum albumin). A stock solution of 1 mM test substance in DMSO was diluted to the desired concentration with phosphate buffer—1% BSA. 40 µl of microsomes were mixed with 20 µl of the solution of the test substance and the reaction was subsequently started with 20 µl of the [$^{14}$C]R,S-MOS solution. The final conditions were: 0.4 mg/ml of microsomal proteins and 30 µl of [$^{14}$C]R,S-MOS in phosphate buffer, pH 7.4, containing 0.5% albumin, DMSO <0.1% and ethanol <2%, in a total volume of 80 µl.

After 1 hour at 37° C. the reaction was stopped by the addition of 0.6 ml of 10% KOH-methanol, 0.7 ml of water and 0.1 ml of hexane:ether (1:1, v/v) which contained 25 µg of non-radioactive MOS and 25 µg of lanosterol as carriers. After shaking, 1 ml of hexane:ether (1:1, v/v) was added to each test tube, these were again shaken and then centrifuged. The upper phase was transferred into a glass test tube, the lower phase was again extracted with hexane:ether and combined with the first extract. The entire extract was evaporated to dryness with nitrogen, the residue was suspended in 50 µl of hexane:ether and applied to a silica gel plate. Chromatographic separation was effected in hexane:ether (1:1, v/v) as the eluent. The Rf values for the MOS substrate and the lanosterol product were 0.91 and, respectively, 0.54. After drying, radioactive MOS and lanosterol were observed on the silica gel plate. The ratio of MOS to lanosterol was determined from the radioactive bands in order to determine the yield of the reaction and OSC inhibition.

The test was carried out on the one hand with a constant test substance concentration of 100 nM and the percentage OSC inhibition against controls was calculated. The more preferred compounds of the present invention exhibit inhibitions larger than 50%. In addition, the test was carried out with different test substance concentrations and subsequently the IC$_{50}$ value was calculated, i.e. the concentration required to reduce the conversion of MOS into lanosterol to 50% of the control value. The preferred compounds of the present invention exhibit IC$_{50}$ values of 1 nM to 10 µM, preferably of 1–100 nM.

The compounds of formula I and their pharmaceutically acceptable acid addition salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable acid addition salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 50 mg to about 500 mg, comes into consideration for the prevention and control of topical and systemic infections by pathogenic fungi. For cholesterol lowering and treatment of impaired glucose tolerance and diabetes the daily dosage conveniently amounts to between 1 and 1000 mg, preferably 10 to 100 mg, for adult patients. Depending on the dosage it is convenient to administer the daily dosage in several dosage units.

The pharmaceutical preparations conveniently contain about 1–500 mg, preferably 10–100 mg, of a compound of formula I.

The following Examples serve to illustrate the present invention in more detail. They are, however, not intended to limit its scope in any manner.

EXAMPLES

Abbreviations:

AcOH=acetic acid, EtOAc=ethylacetate, EtOH=ethanol, THF=tetrahydrofurane, Et$_2$O=diethylether, MeOH=methanol, CH$_2$Cl$_2$=dichloromethane, BOC=t-butyloxycarbonyl, DEAD=Diethyl azodicarboxylate, DBU=1,8-Diazabicyclo[5.4.0]undec-7-ene(1,5–5), DMA=N,N-dimethylacetamide, DMAP=4-Dimethylaminopyridine, EDCI=N-(3-Dime-thylaminopropyl)-N'-ethylcarbodiimide hydrochloride, Et$_3$N=triethylamine, HOBT=1-Hydroxybenzo-triazole, LAH=Lithium aluminium hydride, LDA=lithium diisopropylamide, PdCl$_2$(dppf)=(1,1'-bis (diphenylphosphino)ferrocene)dichloropalladium(II). CH$_2$Cl$_2$ (1:1), Pd(Ph$_3$P)$_4$=tetrakis(triphenylphosphine) palladium, iPr$_2$NEt=DIPEA=Huenigsbase=N-ethyldiisopropylamine, TFA=trifluoroacetic acid.

General Remarks

All reactions were performed under argon.

The purification of the final amines by preparative HPLC [e.g. RP-18, acetonitrile (0.1% HCOOH)/water (0.1% HCOOH), 10% to 95% acetonitrile] yielded mixtures of the corresponding amino formiate and the corresponding halogenide which was used in the reaction. The ratio was not always determined, the purity the final amino salts was >80% after LC-MS.

Example 1

1.1

A solution of 30 g (219 mmol) N-methyl-p-anisidine was dissolved in 250 ml 62% aqueous HBr and 435 ml acetic acid. The reaction mixture was heated to 110° C. for 8 h, cooled and evaporated to yield 44.1 g (99%) of 4-Methylamino-phenol hydrobromide (1:1) as a brown solid, MS: 124 (MH$^+$).

1.2

A solution of 44 g (216 mmol) 4-Methylamino-phenol.hydrobromide (1:1) in 1.1l THF, 270 ml acetonitril and 17.4 ml (216 mmol) pyridine was treated with 49.5 g (227 mmol) of di-tert-butyl dicarbonate and heated for 2 h at 70° C. The reaction was continued at RT for 16 h after the addition of 8.7 ml (108 mmol) pyridine and 24.8 g (113 mmol) of di-tert-butyl dicarbonate. The solution was evaporated to a third and extracted with aqueous 10% KHSO$_4$/Et2O (3×). The organic phase was washed with aqueous 10% NaCl, dried over Na$_2$SO$_4$ and evaporated to yield 47.8 g (99%) of (4-Hydroxy-phenyl)-methyl-carbamic acid tert-butyl ester, MS: 223 (M).

1.3

In analogy to example 1.2, 4-Aminophenol was converted (without pyridine) to (4-Hydroxy-phenyl)-carbamic acid tert-butyl ester, MS: (209, M).

1.4

A solution of 6.56 g (29.4 mmol) of (4-Hydroxy-phenyl)-methyl-carbamic acid tert-butyl ester dissolved in 250 ml of acetone was treated with 12.2 g (88.1 mmol) of K$_2$CO$_3$ and 13.4 ml (88.1 mmol) of 1,6-dibromohexane. The suspension was heated under reflux overnight, cooled, filtered and concentrated. Purification by flash chromatography on silica gel with toluene/EtOAc (95:5) as eluent yielded 9.79 g (86%) of [4-(6-Bromo-hexyloxy)-phenyl]-methyl-carbamic acid tert-butyl ester, MS: 386 (MH$^+$, 1Br).

1.5

In analogy to example 1.4, reaction of (4-Hydroxy-phenyl)-methyl-carbamic acid tert-butyl ester with 1,4-dibromopentane yielded [4-(5-Bromo-pentyloxy)-phenyl]-methyl-carbamic acid tert-butyl ester, MS: 372 (MH$^+$, 1Br).

1.6

In analogy to example 1.4, reaction of (4-Hydroxy-phenyl)-methyl-carbamic acid tert-butyl ester with 1,4-dibromobutane yielded [4-(4-Bromo-butoxy)-phenyl]-methyl-carbamic acid tert-butyl ester, MS: 360 (MH$^{+,}$ $^1$Br).

1.7

In analogy to example 1.4, reaction of (4-Hydroxy-phenyl)-carbamic acid tert-butyl ester with 1,4-dibromobutane yielded [4-(4-Bromo-butoxy)-phenyl]-carbamic acid tert-butyl ester, MS: 344 (MH$^{+,}$ $^1$Br).

1.8

A solution of 40 g (103.7 mmol) of [4-(6-Bromo-hexyloxy)-phenyl]-methyl-carbamic acid tert-butyl ester in 400 ml DMA was treated at RT with 19.9 ml (207.4 mmol) of N-methylallylamine and stirred at RT for 22 h. The solution was concentrated and dissolved in aqueous saturated NaHCO$_3$/Et$_2$O (3×). The organic phase was dried over Na$_2$SO$_4$ and evaporated. Flash column chromatography on silica gel with CH$_2$Cl$_2$/MeOH (95:5) yielded 33.9 g (87%) of {4-[6-(Allyl-methyl-amino)-hexyloxy]-phenyl}-methyl-carbamic acid tert-butyl ester, MS: 377 (MH$^+$).

1.9

In analogy to example 1.8, reaction of [4-(5-Bromo-pentyloxy)-phenyl]-methyl-carbamic acid tert-butyl ester with N-methylallylamine yielded {4-[5-(Allyl-methyl-amino)-pentyloxy]-phenyl}-methyl-carbamic acid tert-butyl ester, MS: 363 (MH$^+$).

1.10

In analogy to example 1.8, reaction of [4-(4-Bromo-butoxy)-phenyl]-methyl-carbamic acid tert-butyl ester with N-methylallylamine yielded {4-[4-(Allyl-methyl-amino)-butoxy]-phenyl}-methyl-carbamic acid tert-butyl ester, MS: 349 (MH$^+$).

1.11

In analogy to example 1.8, reaction of [4-(4-Bromo-butoxy)-phenyl]-carbamic acid tert-butyl ester with 10 eq dimethylamine (33% in ethanol, 5.6 M) yielded (without extraction with aqueous saturated NaHCO$_3$ solution) [4-(4-Dimethylamino-butoxy)-phenyl]-carbamic acid tert-butyl ester hydrobromid (1:1), MS: 309 (MH$^+$).

1.12

A solution of 30.3 g (80.5 mmol) of {4-[6-(Allyl-methyl-amino)-hexyloxy]-phenyl}-methyl-carbamic acid tert-butyl ester in 160 ml CH$_2$Cl$_2$ was treated at −20° C. with 180 ml TFA and warmed up to room temperature during 5 h. The reaction mixture was evaporated, treated with aqueous saturated NaHCO$_3$ solution/Et$_2$O (3×), dried (Na$_2$SO$_4$) and evaporated to yield {4-[6-(Allyl-methyl-amino)-hexyloxy]-phenyl}-methyl-amine, MS: 277 (MH$^+$).

1.13

In analogy to example 1.12, {4-[5-(Allyl-methyl-amino)-pentyloxy]-phenyl}-methyl-carbamic acid tert-butyl ester was converted to {4-[5-(Allyl-methyl-amino)-pentyloxy]-phenyl}-methyl-amine, MS: 263 (MH$^+$).

1.14

In analogy to example 1.12, {4-[4-(Allyl-methyl-amino)-butoxy]-phenyl}-methyl-carbamic acid tert-butyl ester was converted to {4-[4-(Allyl-methyl-amino)-butoxy]-phenyl}-methyl-amine, MS: 249 (MH$^+$).

1.15

In analogy to example 1.12, [4-(4-Dimethylamino-butoxy)-phenyl]-carbamic acid tert-butyl ester hydrobromid (1:1) was converted (after extraction with aqueous saturated NaHCO$_3$ solution/CH$_2$Cl$_2$ (3×)) to 4-(4-Dimethylamino-butoxy)-phenylamine, MS: 209 (MH$^+$).

1.16

In analogy to example 1.12, [4-(6-Bromo-hexyloxy)-phenyl]-methyl-carbamic acid tert-butyl ester was converted (without extraction with aqueous saturated NaHCO$_3$ solution) to [4-(6-Bromo-hexyloxy)-phenyl]-methyl-amine.trifluoro-acetate, MS: 288 (MH$^+$).

Example 2

Step 1

4.5 mmol [4-(6-Bromo-hexyloxy)-phenyl]-methyl-ammonium trifluoro-acetate were dissolved in CH$_2$Cl$_2$ and extracted with aqueous Na$_2$CO$_3$ (2M). The aqueous phase was again extracted with CH$_2$Cl$_2$, the combined organic phases were dried with MgSO$_4$, evaporated and dissolved in 25 ml CH$_2$Cl$_2$.4.95 mmol DIPEA and 4.95 mmol of either 4-bromo-benzenesulfonyl chloride, 4-fluoro-benzenesulfonyl chloride, 4-chloro-benzenesulfonyl chloride or 4-trifluoromethyl-benzenesulfonyl chloride were added. After 16 h at RT the solvent was evaporated and the residue was purified by prep. HPLC: RP-18, Acetonitril (0.1% HCOOH)/water (0.1% HCOOH), 20%–95% Acetonitril. The following compounds were obtained and immediately used in step 2:

4-Bromo-N-[4-(6-bromo-hexyloxy)-phenyl]-N-methyl-benzenesulfonamide, 4-fluoro-N-[4-(6-bromo-hexyloxy)-phenyl]-N-methyl-benzenesulfonamide, 4-chloro-N-[4-(6-bromo-hexyloxy)-phenyl]-N-methyl-benzenesulfonamide, 4-trifluoromethN-[4-(6-bromo-hexyloxy)-phenyl]-N-methyl-benzenesulfonamide.

Step 2

A solution of 0.25 mmol (1 equivalent) 6-bromo compound in 0.7 ml dry DMA was treated with a solution of 0.5 mmol (2 equivalents) secondary amine in 0.15 ml dry DMA at room temperature. After 16 h, 2 equivalents of secondary amine were added again to the solution. The reaction mixture was allowed to stand over night at room temperature, treated with 0.2 ml formic acid and purified by preparative HPLC [RP-18, acetonitrile (0.1% HCOOH)/water (0.1% HCOOH), 10% to 95% acetonitrile]. After evaporation, the tertiary amine was received as amino.hydrobromide. The following compounds were obtained using 4-Bromo-N-[4-(6-bromo-hexyloxy)-phenyl]-N-methyl-benzenesulfonamide as the 6-bromo compound and the corresponding amines:

| Example | Product | MS MH+ 1 Br | Amine (educt) |
|---|---|---|---|
| 2.1 | N-[4-(6-Azepan-1-yl-hexyloxy)-phenyl]-4-bromo-N-methyl-benzenesulfonamide | 523 | HEXAMETHYLENEIMINE |
| 2.2 | 4-Bromo-N-(4-{6-[(2-methoxy-ethyl)-methyl-amino]-hexyloxy}-phenyl)-N-methyl-benzenesulfonamide | 513 | N-(2-METHOXYETHYL)-METHYLAMINE |
| 2.3 | 4-Bromo-N-{4-[6-(ethyl-methyl-amino)-hexyloxy]-phenyl}-N-methyl-benzenesulfonamide | 483 | N-ETHYLMETHYLAMINE |
| 2.4 | 4-Bromo-N-methyl-N-{4-[6-(2-methyl-piperidin-1-yl)-hexyloxy]-phenyl}-benzenesulfonamide | 523 | 2-METHYLPIPERIDINE |
| 2.5 | 4-Bromo-N-(4-{6-[(2-hydroxy-ethyl)-methyl-amino]-hexyloxy}-phenyl)-N-methyl-benzenesulfonamide | 499 | 2-(METHYLAMINO)-ETHANOL |
| 2.6 | [(6-{4-[(4-Bromo-benzenesulfonyl)-methyl-amino]-phenoxy}-hexyl)-methyl-amino]-acetic acid ethyl ester | 541 | SARCOSINE ETHYL ESTER HYDROCHLORIDE |
| 2.7 | 4-Bromo-N-{4-[6-(butyl-methyl-amino)-hexyloxy]-phenyl}-N-methyl-benzenesulfonamide | 511 | N-METHYLBUTYLAMINE |
| 2.8 | 4-Bromo-N-[4-(6-diallylamino-hexyloxy)-phenyl]-N-methyl-benzenesulfonamide | 521 | DIALLYLAMINE |
| 2.9 | 4-Bromo-N-methyl-N-[4-(6-pyrrolidin-1-yl-hexyloxy)-phenyl]-benzenesulfonamide | 495 | PYRROLIDINE |
| 2.10 | 4-Bromo-N-methyl-N-{4-[6-(methyl-prop-2-ynyl-amino)-hexyloxy]-phenyl}-benzenesulfonamide | 493 | N-METHYLPROPARGYL-AMINE |
| 2.11 | 4-Bromo-N-methyl-N-[4-(6-piperidin-1-yl-hexyloxy)-phenyl]-benzenesulfonamide | 509 | PIPERIDINE |
| 2.12 | 4-Bromo-N-{4-[6-(ethyl-isopropyl-amino)-hexyloxy]-phenyl}-N-methyl-benzenesulfonamide | 511 | N-ETHYLISOPROPYL-AMINE |
| 2.13 | 4-Bromo-N-methyl-N-[4-(6-morpholin-4-yl-hexyloxy)-phenyl]-benzenesulfonamide | 511 | MORPHOLINE |
| 2.14 | 4-Bromo-N-{4-[6-(isopropyl-methyl-amino)-hexyloxy]-phenyl}-N-methyl-benzenesulfonamide | 497 | N-METHYLISOPROPYL-AMINE |
| 2.15 | 4-Bromo-N-{4-[6-(3,6-dihydro-2H-pyridin-1-yl)-hexyloxy]-phenyl}-N-methyl-benzenesulfonamide | 507 | 1,2,3,6-TETRAHYDRO-PYRIDINE |
| 2.16 | 4-Bromo-N-(4-{6-[ethyl-(2-hydroxy-ethyl)-amino]-hexyloxy}-phenyl)-N-methyl-benzenesulfonamide | 513 | 2-(ETHYLAMINO)-ETHANOL |
| 2.17 | 4-Bromo-N-[4-(6-dimethylamino-hexyloxy)-phenyl]-N-methyl-benzenesulfonamide | 469 | DIMETHYLAMINE |
| 2.18 | 4-Bromo-N-methyl-N-{4-[6-(methyl-propyl-amino)-hexyloxy]-phenyl}-benzenesulfonamide | 497 | N-METHYL-N-PROPYL AMINE |
| 2.19 | 4-Bromo-N-{4-[6-(2,5-dihydro-pyrrol-1-yl)-hexyloxyl-phenyl}-N-methyl-benzenesulfonamide | 493 | 3-PYRROLINE |
| 2.20 | 4-Bromo-N-[4-(6-diethylamino-hexyloxy)-phenyl]-N-methyl-benzenesulfonamide | 497 | DIETHYLAMINE |
| 2.21 | 4-Bromo-N-methyl-N-[4-(6-thiomorpholin-4-yl-hexyloxy)-phenyl]-benzenesulfonamide | 527 | THIOMORPHOLINE |

-continued

| Example | Product | MS MH+ 1 Br | Amine (educt) |
|---|---|---|---|
| 2.22 | 4-Bromo-N-{4-[6-(butyl-ethyl-amino)-hexyloxy]-phenyl}-N-methyl-benzenesulfonamide | 525 | N-ETHYL-N-BUTYLAMINE |
| 2.23 | 4-Bromo-N-{4-[6-(4-hydroxy-piperidin-1-yl)-hexyloxy]-phenyl}-N-methyl-benzenesulfonamide | 525 | 4-HYDROXYPIPERIDINE |
| 2.24 | 4-Bromo-N-methyl-N-{4-[6-(4-methyl-piperazin-1-yl)-hexyloxy]-phenyl}-benzenesulfonamide | 524 | 1-METHYLPIPERAZINE |
| 2.25 | 4-Bromo-N-{4-[6-(3-hydroxy-piperidin-1-yl)-hexyloxy]-phenyl}-N-methyl-benzenesulfonamide | 525 | 3-HYDROXY-1-METHYL-PIPERIDINE |
| 2.26 | 4-Bromo-N-{4-[6-(3-dimethylamino-pyrrolidin-1-yl)-hexyloxy]-phenyl}-N-methyl-benzenesulfonamide | 538 | 3-(DIMETHYLAMINO)-PYRROLIDINE |
| 2.27 | 4-Bromo-N-{4-[6-(4-hydroxymethyl-piperidin-1-yl)-hexyloxy]-phenyl}-N-methyl-benzenesulfonamide | 539 | 4-PIPERIDYLMETHANOL |

The following compounds were obtained using 4-Fluoro-N-[4-(6-bromo-hexyloxy)-phenyl]-N-methyl-benzenesulfonamide as the 6-bromo compound and the corresponding amines in the above described reaction:

| Example | Product | MS MH+ | Amine (educt) |
|---|---|---|---|
| 2.28 | N-[4-(6-Azepan-1-yl-hexyloxy)-phenyl]-4-fluoro-N-methyl-benzenesulfonamide | 463 | HEXAMETHYLENEIMINE |
| 2.29 | 4-Fluoro-N-(4-{6-[(2-methoxy-ethyl)-methyl-amino]-hexyloxy}-phenyl)-N-methyl-benzenesulfonamide | 453 | N-(2-METHOXYETHYL)-METHYLAMINE |
| 2.30 | N-{4-[6-(Ethyl-methyl-amino)-hexyloxy]-phenyl}-4-fluoro-N-methyl-benzenesulfonamide | 423 | N-ETHYLMETHYLAMINE |
| 2.31 | 4-Fluoro-N-methyl-N-{4-[6-(2-methyl-piperidin-1-yl)-hexyloxy]-phenyl}-benzenesulfonamide | 463 | 2-METHYLPIPERIDINE |
| 2.32 | 4-Fluoro-N-(4-{6-[(2-hydroxy-ethyl)-methyl-amino]-hexyloxy}-phenyl)-N-methyl-benzenesulfonamide | 439 | 2-(METHYLAMINO)-ETHANOL |
| 2.33 | [(6-{4-[(4-Fluoro-benzenesulfonyl)-methyl-amino]-phenoxy}-hexyl)-methyl-amino]-acetic acid ethyl ester | 481 | SARCOSINE ETHYL ESTER HYDROCHLORIDE |
| 2.34 | N-{4-[6-(Butyl-methyl-amino)-hexyloxy]-phenyl}-4-fluoro-N-methyl-benzenesulfonamide | 451 | N-METHYLBUTYLAMINE |
| 2.35 | N-[4-(6-Diallylamino-hexyloxy)-phenyl]-4-fluoro-N-methyl-benzenesulfonamide | 461 | DIALLYLAMINE |
| 2.36 | 4-Fluoro-N-methyl-N-[4-(6-pyrrolidin-1-yl-hexyloxy)-phenyl]-benzenesulfonamide | 435 | PYRROLIDINE |
| 2.37 | 4-Fluoro-N-methyl-N-{4-[6-(methyl-prop-2-ynyl-amino)-hexyloxy]-phenyl}-benzenesulfonamide | 433 | N-METHYLPROPARGYL-AMINE |
| 2.38 | 4-Fluoro-N-methyl-N-[4-(6-piperidin-1-yl-hexyloxy)-phenyl]-benzenesulfonamide | 449 | PIPERIDINE |
| 2.39 | N-{4-[6-(Ethyl-isopropyl-amino)-hexyloxy]-phenyl}-4-fluoro-N-methyl-benzenesulfonamide | 451 | N-ETHYLISOPROPYL-AMINE |
| 2.40 | 4-Fluoro-N-methyl-N-[4-(6-morpholin-4-yl-hexyloxy)-phenyl]-benzenesulfonamide | 451 | MORPHOLINE |
| 2.41 | 4-Fluoro-N-{4-[6-(isopropyl-methyl-amino)-hexyloxy]-phenyl}-N-methyl-benzenesulfonamide | 437 | N-METHYLISOPROPYL-AMINE |

-continued

| Example | Product | MS MH+ | Amine (educt) |
|---|---|---|---|
| 2.42 | N-{4-[6-(3,6-Dihydro-2H-pyridin-1-yl)-hexyloxy]-phenyl}-4-fluoro-N-methyl-benzenesulfonamide | 447 | 1,2,3,6-TETRAHYDRO-PYRIDINE |
| 2.43 | N-(4-{6-[Ethyl-(2-hydroxy-ethyl)-amino]-hexyloxy}-phenyl)-4-fluoro-N-methyl-benzenesulfonamide | 453 | 2-(ETHYLAMINO)-ETHANOL |
| 2.44 | N-[4-(6-Dimethylamino-hexyloxy)-phenyl]-4-fluoro-N-methyl-benzenesulfonamide | 409 | DIMETHYLAMINE |
| 2.45 | 4-Fluoro-N-methyl-N-{4-[6-(methyl-propyl-amino)-hexyloxy]-phenyl}-benzenesulfonamide | 437 | N-METHYL-N-PROPYL-AMINE |
| 2.46 | N-{4-[6-(2,5-Dihydro-pyrrol-1-yl)-hexyloxy]-phenyl}-4-fluoro-N-methyl-benzenesulfonamide | 434 | 3-PYRROLINE |
| 2.47 | N-[4-(6-Diethylamino-hexyloxy)-phenyl]-4-fluoro-N-methyl-benzenesulfonamide | 437 | DIETHYLAMINE |
| 2.48 | 4-Fluoro-N-methyl-N-[4-(6-thiomorpholin-4-yl-hexyloxy)-phenyl]-benzenesulfonamide | 467 | THIOMORPHOLINE |
| 2.49 | N-{4-[6-(Butyl-ethyl-amino)-hexyloxy]-phenyl}-4-fluoro-N-methyl-benzenesulfonamide | 465 | N-ETHYL-N-BUTYLAMINE |
| 2.50 | 4-Fluoro-N-{4-[6-(4-hydroxy-piperidin-1-yl)-hexyloxy]-phenyl}-N-methyl-benzenesulfonamide | 465 | 4-HYDROXYPIPERIDINE |
| 2.51 | 4-Fluoro-N-methyl-N-{4-[6-(4-methyl-piperazin-1-yl)-hexyloxy]-phenyl}-benzenesulfonamide | 464 | 1-METHYLPIPERAZINE |
| 2.52 | 4-Fluoro-N-{4-[6-(3-hydroxy-piperidin-1-yl)-hexyloxy]-phenyl}-N-methyl-benzenesulfonamide | 465 | 3-HYDROXY-1-METHYL-PIPERIDINE |
| 2.53 | 4-Fluoro-N-{4-[6-(4-hydroxymethyl-piperidin-1-yl)-hexyloxy]-phenyl}-N-methyl-benzenesulfonamide | 479 | 4-PIPERIDYLMETHANOL |

The following compounds were obtained using 4-Chloro-N-[4-(6-bromo-hexyloxy)-phenyl]-N-methyl-benzenesulfonamide as the 6-bromo compound and the corresponding amines in the above described reaction:

| Example | Product | MS MH+ 1 Cl | Amine (educt) |
|---|---|---|---|
| 2.54 | N-[4-(6-Azepan-1-yl-hexyloxy)-phenyl]-4-chloro-N-methyl-benzenesulfonamide | 479 | HEXAMETHYLENEIMINE |
| 2.55 | 4-Chloro-N-(4-{6-[(2-methoxy-ethyl)-methyl-amino]-hexyloxy}-phenyl)-N-methyl-benzenesulfonamide | 469 | N-(2-METHOXYETHYL)-METHYLAMINE |
| 2.56 | 4-Chloro-N-{4-[6-(ethyl-methyl-amino)-hexyloxy]-phenyl}-N-methyl-benzenesulfonamide | 439 | N-ETHYLMETHYLAMINE |
| 2.57 | 4-Chloro-N-methyl-N-{4-[6-(2-methyl-piperidin-1-yl)-hexyloxy]-phenyl}-benzenesulfonamide | 479 | 2-METHYLPIPERIDINE |
| 2.58 | 4-Chloro-N-(4-{6-[(2-hydroxy-ethyl)-methyl-amino]-hexyloxy}-phenyl)-N-methyl-benzenesulfonamide | 455 | 2-(METHYLAMINO)-ETHANOL |
| 2.59 | [(6-{4-[(4-Chloro-benzenesulfonyl)-methyl-amino]-phenoxy}-hexyl)-methyl-amino]-acetic acid ethyl ester | 497 | SARCOSINE ETHYL ESTER HYDROCHLORIDE |
| 2.60 | N-{4-[6-(Butyl-methyl-amino)-hexyloxy]-phenyl}-4-chloro-N-methyl-benzenesulfonamide | 467 | N-METHYLBUTYLAMINE |
| 2.61 | 4-Chloro-N-[4-(6-diallylamino-hexyloxy)-phenyl]-N-methyl-benzenesulfonamide | 477 | DIALLYLAMINE |

| Example | Product | MS MH+ 1 Cl | Amine (educt) |
|---|---|---|---|
| 2.62 | 4-Chloro-N-methyl-N-[4-(6-pyrrolidin-1-yl-hexyloxy)-phenyl]-benzenesulfonamide | 451 | PYRROLIDINE |
| 2.63 | 4-Chloro-N-methyl-N-{4-[6-(methyl-prop-2-ynyl-amino)-hexyloxy]-phenyl}-benzenesulfonamide | 449 | N-METHYLPROPARGYL-AMINE |
| 2.64 | 4-Chloro-N-methyl-N-[4-(6-piperidin-1-yl-hexyloxy)-phenyl]-benzenesulfonamide | 465 | PIPERIDINE |
| 2.65 | 4-Chloro-N-{4-[6-(ethyl-isopropyl-amino)-hexyloxy]-phenyl}-N-methyl-benzenesulfonamide | 467 | N-ETHYLISOPROPYL-AMINE |
| 2.66 | 4-Chloro-N-methyl-N-[4-(6-morpholin-4-yl-hexyloxy)-phenyl]-benzenesulfonamide | 467 | MORPHOLINE |
| 2.67 | 4-Chloro-N-{4-[6-(isopropyl-methyl-amino)-hexyloxy]-phenyl}-N-methyl-benzenesulfonamide | 453 | N-METHYLISOPROPYL AMINE |
| 2.68 | 4-Chloro-N-{4-[6-(3,6-dihydro-2H-pyridin-1-yl)-hexyloxy]-phenyl}-N-methyl-benzenesulfonamide | 463 | 1,2,3,6-TETRAHYDRO-PYRIDINE |
| 2.69 | 4-Chloro-N-(4-{6-[ethyl-(2-hydroxy-ethyl)-amino]-hexyloxy}-phenyl)-N-methyl-benzenesulfonamide | 469 | 2-(ETHYLAMINO)-ETHANOL |
| 2.70 | 4-Chloro-N-[4-(6-dimethylamino-hexyloxy)-phenyl]-N-methyl-benzenesulfonamide | 425 | DIMETHYLAMINE |
| 2.71 | 4-Chloro-N-methyl-N-{4-[6-(methyl-propyl-amino)-hexyloxy]-phenyl}-benzenesulfonamide | 453 | N-METHYL-N-PROPYLAMINE |
| 2.72 | 4-Chloro-N-{4-[6-(2,5-dihydro-pyrrol-1-yl)-hexyloxy]-phenyl}-N-methyl-benzenesulfonamide | 449 | 3-PYRROLINE |
| 2.73 | 4-Chloro-N-[4-(6-diethylamino-hexyloxy)-phenyl]-N-methyl-benzenesulfonamide | 453 | DIETHYLAMINE |
| 2.74 | 4-Chloro-N-methyl-N-[4-(6-thiomorpholin-4-yl-hexyloxy)-phenyl]-benzenesulfonamide | 483 | THIOMORPHOLINE |
| 2.75 | N-{4-[6-(Butyl-ethyl-amino)-hexyloxy]-phenyl}-4-chloro-N-methyl-benzenesulfonamide | 481 | N-ETHYL-N-BUTYLAMINE |
| 2.76 | 4-Chloro-N-{4-[6-(4-hydroxy-piperidin-1-yl)-hexyloxy]-phenyl}-N-methyl-benzenesulfonamide | 481 | 4-HYDROXYPIPERIDINE |
| 2.77 | 4-Chloro-N-methyl-N-{4-[6-(4-methyl-piperazin-1-yl)-hexyloxy]-phenyl}-benzenesulfonamide | 480 | 1-METHYLPIPERAZINE |
| 2.78 | 4-Chloro-N-{4-[6-(3-hydroxy-piperidin-1-yl)-hexyloxy]-phenyl}-N-methyl-benzenesulfonamide | 481 | 3-HYDROXY-1-METHYL-PIPERIDINE |
| 2.79 | 4-Chloro-N-{4-[6-(3-dimethylamino-pyrrolidin-1-yl)-hexyloxy]-phenyl}-N-methyl-benzenesulfonamide | 494 | 3-(DIMETHYLAMIINO)-PYRROLIDINE |
| 2.80 | 4-Chloro-N-{4-[6-(4-hydroxymethyl-piperidin-1-yl)-hexyloxy]-phenyl}-N-methyl-benzenesulfonamide | 495 | 4-PIPERIDYLMETHANOL |

The following compounds were obtained using 4-Trifluorometh-N-[4-(6-bromo-hexyloxy)-phenyl]-N-methyl-benzenesulfonamide as the 6-bromo compound and the corresponding amines in the above described reaction:

| Example | Product | MS MH+ | Amine (educt) |
|---|---|---|---|
| 2.81 | N-[4-(6-Azepan-1-yl-hexyloxy)-phenyl]-N-methyl-4-trifluoromethyl-benzenesulfonamide | 513 | HEXAMETHYLENEIMINE |

| Example | Product | MS MH+ | Amine (educt) |
|---|---|---|---|
| 2.82 | N-(4-{6-[(2-Methoxy-ethyl)-methyl-amino]-hexyloxy}-phenyl)-N-methyl-4-trifluoromethyl-benzenesulfonamide | 503 | N-(2-METHOXYETHYL)-METHYLAMINE |
| 2.83 | N-{4-[6-(Ethyl-methyl-amino)-hexyloxy]-phenyl}-N-methyl-4-trifluoromethyl-benzenesulfonamide | 473 | N-ETHYLMETHYLAMINE |
| 2.84 | N-Methyl-N-{4-[6-(2-methyl-piperidin-1-yl)-hexyloxy]-phenyl}-4-trifluoromethyl-benzenesulfonamide | 513 | 2-METHYLPIPERIDINE |
| 2.85 | N-(4-{6-[(2-Hydroxy-ethyl)-methyl-amino]-hexyloxy}-phenyl)-N-methyl-4-trifluoromethyl-benzenesulfonamide | 489 | 2-(METHYLAMINO)-ETHANOL |
| 2.86 | [Methyl-(6-{4-[methyl-(4-trifluoromethyl-benzenesulfonyl)-amino]-phenoxy}-hexyl)-amino]-acetic acid ethyl ester | 531 | SARCOSINE ETHYL ESTER HYDROCHLORIDE |
| 2.87 | N-{4-[6-(Butyl-methyl-amino)-hexyloxy]-phenyl}-N-methyl-4-trifluoromethyl-benzenesulfonamide | 501 | N-METHYLBUYTYLAMINE |
| 2.88 | N-[4-(6-Diallylamino-hexyloxy)-phenyl]-N-methyl-4-trifluoromethyl-benzenesulfonamide | 511 | DIALLYLAMINE |
| 2.89 | N-Methyl-N-[4-(6-pyrrolidin-1-yl-hexyloxy)-phenyl]-4-trifluoromethyl-benzenesulfonamide | 485 | PYRROLIDINE |
| 2.90 | N-Methyl-N-{4-[6-(methyl-prop-2-ynyl-amino)-hexyloxy]-phenyl}-4-trifluoromethyl-benzenesulfonamide | 483 | N-METHYLPROPARGYL-AMINE |
| 2.91 | N-Methyl-N-[4-(6-piperidin-1-yl-hexyloxy)-phenyl]-4-trifluoromethyl-benzenesulfonamide | 499 | PIPERIDINE |
| 2.92 | N-{4-[6-(Ethyl-isopropyl-amino)-hexyloxy]-phenyl}-N-methyl-4-trifluoromethyl-benzenesulfonamide | 501 | N-ETHYLISOPROPYL-AMINE |
| 2.93 | N-Methyl-N-[4-(6-morpholin-4-yl-hexyloxy)-phenyl]-4-trifluoromethyl-benzenesulfonamide | 501 | MORPHOLINE |
| 2.94 | N-{4-[6-(Isopropyl-methyl-amino)-hexyloxy]-phenyl}-N-methyl-4-trifluoromethyl-benzenesulfonamide | 487 | N-METHYLISOPROPYL-AMINE |
| 2.95 | N-{4-[6-(3,6-Dihydro-2H-pyridin-1-yl)-hexyloxy]-phenyl}-N-methyl-4-trifluoromethyl-benzenesulfonamide | 497 | 1,2,3,6-TETRAHYDRO-PYRIDINE |
| 2.96 | N-(4-{6-[Ethyl-(2-hydroxy-ethyl)-amino]-hexyloxy}-phenyl)-N-methyl-4-trifluoromethyl-benzenesulfonamide | 503 | 2-(ETHYLAMINO)-ETHANOL |
| 2.97 | N-[4-(6-Dimethylamino-hexyloxy)-phenyl]-N-methyl-4-trifluoromethyl-benzenesulfonamide | 459 | DIMETHYLAMINE |
| 2.98 | N-Methyl-N-{4-[6-(methyl-propyl-amino)-hexyloxy]-phenyl}-4-trifluoromethyl-benzenesulfonamide | 487 | N-METHYL-N-PROPYL-AMINE |
| 2.99 | N-{4-[6-(2,5-Dihydro-pyrrol-1-yl)-hexyloxy]-phenyl}-N-methyl-4-trifluoromethyl-benzenesulfonamide | 483 | 3-PYRROLINE |
| 2.100 | N-[4-(6-Diethylamino-hexyloxy)-phenyl]-N-methyl-4-trifluoromethyl-benzenesulfonamide | 487 | DIETHYLAMINE |
| 2.101 | N-Methyl-N-[4-(6-thiomorpholin-4-yl-hexyloxy)-phenyl]-4-trifluoromethyl-benzenesulfonamide | 517 | THIOMORPHOLINE |
| 2.102 | N-{4-[6-(Butyl-ethyl-amino)-hexyloxyl-phenyl}-N-methyl-4-trifluoromethyl-benzenesulfonamide | 515 | N-ETHYL-N-BUTYLAMINE |
| 2.103 | N-{4-[6-(4-Hydroxy-piperidin-1-yl)-hexyloxy]-phenyl}-N-methyl-4-trifluoromethyl-benzenesulfonamide | 515 | 4-HYDROXYPIPERIDINE |
| 2.104 | N-Methyl-N-{4-[6-(4-methyl-piperazin-1-yl)-hexyloxy]-phenyl}-4-trifluoromethyl-benzenesulfonamide | 514 | 1-METHYLPIPERAZINE |
| 2.105 | N-{4-[6-(3-Hydroxy-piperidin-1-yl)-hexyloxy]-phenyl}-N-methyl-4-trifluoromethyl-benzenesulfonamide | 515 | 3-HYDROXY-1-METHYL-PIPERIDINE |
| 2.106 | N-{4-[6-(3-Dimethylamino-pyrrolidin-1-yl)-hexyloxy]-phenyl}-N-methyl-4-trifluoromethyl-benzenesulfonamide | 528 | 3-(DIMETHYLAMINO)-PYRROLIDINE |

-continued

| Example | Product | MS MH+ | Amine (educt) |
|---------|---------|--------|---------------|
| 2.107 | N-{4-[6-(4-Hydroxymethyl-piperidin-1-yl)-hexyloxy]-phenyl}-N-methyl-4-trifluoromethyl-benzenesulfonamide | 529 | 4-PIPERIDYLMETHANOL |

Example 3

A solution of 0.153 mmol of free amine in 0.35 ml dry dioxane was treated with 0.23 mmol isocyanate in 0.54 ml dry dioxane. The solution was allowed to stand over night at room temperature. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation the urea was obtained as the amino formiate. The following compounds were obtained using the corresponding amines and isocyanates:

| Example | Product | MS MH+ | Amine (educt) | Isocyanate (educt) |
|---------|---------|--------|---------------|--------------------|
| 3.1 | 1-{4-[6-(Allyl-methyl-amino)-hexyloxy]-phenyl}-3-(4-fluoro-3-trifluoromethyl-phenyl)-1-methyl-urea; HCOOH | 482 | {4-[6-(Allyl-methyl-amino)-hexyloxy]-phenyl}-methyl-amine | 4-Fluoro-3-trifluoromethyl-phenylisocyanate |
| 3.2 | 1-{4-[6-(Allyl-methyl-amino)-hexyloxy]-phenyl}-3-(2,4-difluoro-phenyl)-1-methyl-urea; HOOH | 432 | {4-[6-(Allyl-methyl-amino)-hexyloxy]-phenyl}-methyl-amine | 2,4-Difluoro-phenylisocyanate |
| 3.3 | 1-{4-[6-(Allyl-methyl-amino)-hexyloxy]-phenyl}-3-(2,4-dimethoxy-phenyl)-1-methyl-urea; HOOH | 456 | {4-[6-(Allyl-methyl-amino)-hexyloxy]-phenyl}-methyl-amine | 2,4 Dimethoxy-phenylisocyanate |
| 3.4 | 1-{4-[6-(Allyl-methyl-amino)-hexyloxy]-phenyl}-3-(4-fluoro-phenyl)-1-methyl-urea; HOOH | 414 | {4-[6-(Allyl-methyl-amino)-hexyloxy]-phenyl}-methyl-amine | 4-Fluorophenyl-isocyanate |
| 3.5 | 1-{4-[6-(Allyl-methyl-amino)-hexyloxy]-phenyl}-3-(4-methoxy-phenyl)-1-methyl-urea; HOOH | 426 | {4-[6-(Allyl-methyl-amino)-hexyloxy]-phenyl}-methyl-amine | 4-Methoxyphenyl-isocyanate |
| 3.6 | 1-{4-[6-(Allyl-methyl-amino)-hexyloxy]-phenyl}-1-methyl-3-p-tolyl-urea; HOOH | 410 | {4-[6-(Allyl-methyl-amino)-hexyloxy]-phenyl}-methyl-amine | 4-Methylphenyl-isocyanate |
| 3.7 | 1-{4-[6-(Allyl-methyl-amino)-hexyloxy]-phenyl}-3-(4-methoxy-2-methyl-phenyl)-1-methyl-urea; HCOOH | 440 | {4-[6-(Allyl-methyl-amino)-hexyloxy]-phenyl}-methyl-amine | 4-Methoxy-2-Methylphenyl-isocyanate |
| 3.8 | 1-{4-[6-(Allyl-methyl-amino)-hexyloxy]-phenyl}-3-(2,4-dimethyl-phenyl)-1-methyl-urea; HOOH | 424 | {4-[6-(Allyl-methyl-amino)-hexyloxy]-phenyl}-methyl-amine | 2,4 Dimethyl-phenylisocyanate |
| 3.9 | 1-{4-[6-(Allyl-methyl-amino)-hexyloxy]-phenyl}-1-methyl-3-(3,4,5-trimethoxy-phenyl)-urea; HOOH | 486 | {4-[6-(Allyl-methyl-amino)-hexyloxy]-phenyl}-methyl-amine | 3,4,5 Trimethoxy-phenylisocyanate |
| 3.10 | 1-{4-[6-(Allyl-methyl-amino)-hexyloxy]-phenyl}-3-(3,4-dimethyl-phenyl)-1-methyl-urea; HCOOH | 424 | {4-[6-(Allyl-methyl-amino)-hexyloxy]-phenyl}-methyl-amine | 3,4 Dimethyl-phenylisocyanate |
| 3.11 | 3-(4-Acetyl-phenyl)-1-{4-[6-(allyl-methyl-amino)-hexyloxy]-phenyl}-1-methyl-urea; HCOOH | 438 | {4-[6-(Allyl-methyl-amino)-hexyloxy]-phenyl}-methyl-amine | 4-Acetylphenyl-isocyanate |
| 3.12 | 1-{4-[6-(Allyl-methyl-amino)-hexyloxy]-phenyl}-3-(4-butyl-phenyl)-1-methyl-urea; HCOOH | 452 | {4-[6-(Allyl-methyl-amino)-hexyloxy]-phenyl}-methyl-amine | 4-Butylphenyl-isocyanate |
| 3.13 | 1-{4-[6-(Allyl-methyl-amino)-hexyloxy]-phenyl}-1-methyl-3-(4-methylsulfanyl-phenyl)-urea; HCOOH | 442 | {4-[6-(Allyl-methyl-amino)-hexyloxy]-phenyl}-methyl-amine | 4-Methyl-mercaptophenyl-isocyanate |

-continued

| Example | Product | MS MH+ | Amine (educt) | Isocyanate (educt) |
|---|---|---|---|---|
| 3.14 | 1-{4-[6-(Allyl-methyl-amino)-hexyloxy]-phenyl}-3-(4-isopropyl-phenyl)-1-methyl-urea; HCOOH | 438 | {4-[6-(Allyl-methyl-amino)-hexyloxy]-phenyl}-methyl-amine | 4-Isopropylphenyl-isocyanate |
| 3.15 | 1-{4-[6-(Allyl-methyl-amino)-hexyloxy]-phenyl}-3-(3,4-dichloro-phenyl)-1-methyl-urea; HCOOH | 464 (2 Cl) | {4-[6-(Allyl-methyl-amino)-hexyloxy]-phenyl}-methyl-amine | 3,4 Dichlorphenyl-isocyanate |
| 3.16 | 1-{4-[6-(Allyl-methyl-amino)-hexyloxy]-phenyl}-3-(4-bromo-phenyl)-1-methyl-urea; HCOOH | 474 (1 Br) | {4-[6-(Allyl-methyl-amino)-hexyloxy]-phenyl}-methyl-amine | 4-Bromphenyl-isocyanate |
| 3.17 | 1-{4-[6-(Allyl-methyl-amino)-hexyloxy]-phenyl}-1-methyl-3-naphthalen-2-yl-urea; HCOOH | 446 | {4-[6-(Allyl-methyl-amino)-hexyloxy]-phenyl}-methyl-amine | 2-Naphthyl-isocyanate |
| 3.18 | 1-{4-[6-(Allyl-methyl-amino)-hexyloxy]-phenyl}-1-methyl-3-naphthalen-1-yl-urea; HCOOH | 446 | {4-[6-(Allyl-methyl-amino)-hexyloxy]-phenyl}-methyl-amine | 1-Naphthyl-isocyanate |
| 3.19 | 1-{4-[6-(Allyl-methyl-amino)-hexyloxy]-phenyl}-1-methyl-3-phenethyl-urea; HCOOH | 424 | {4-[6-(Allyl-methyl-amino)-hexyloxy]-phenyl}-methyl-amine | 2-Phenylethyl-isocyanate |

Example 4

A solution of 0.153 mmol of amine in 0.35 ml dry dioxane was treated with (0.46 mmol; 3 equivalents) Hünigsbase and 0.2 mmol chloroformate in 0.54 ml dry dioxane. The solution was allowed to stand over night at room temperature and the resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation the carbamate was obtained as a mixture of amino hydrochloride and formiate. The following compounds were obtained using the corresponding amines and chloroformates:

| Example | Product | MS MH+ | Amine (educt) | Chloroformate (educt) |
|---|---|---|---|---|
| 4.1 | {4-[6-(Allyl-methyl-amino)-hexyloxy]-phenyl}-methyl-carbamic acid ethyl ester; HCl | 349 | {4-[6-(Allyl-methyl-amino)-hexyloxy]-phenyl}-methyl-amine; 68–7967 | Ethylchloroformate |
| 4.2 | {4-[6-(Allyl-methyl-amino)-hexyloxy]-phenyl}-methyl-carbamic acid 9H-fluoren-9-ylmethyl ester; HCl | 499 | {4-[6-(Allyl-methyl-amino)-hexyloxy]-phenyl}-methyl-amine; 68–7967 | 9-Fluorenylmethyl-chloroformate |
| 4.3 | {4-[6-(Allyl-methyl-amino)-hexyloxy]-phenyl}-methyl-carbamic acid 2,2,2-trichloro-1,1-dimethyl-ethyl ester; HCl | 479 (3 Cl) | {4-[6-(Allyl-methyl-amino)-hexyloxy]-phenyl}-methyl-amine; 68–7967 | 2,2,2-Trichloro-1,1-Dimethylethylchloroformate |
| 4.4 | {4-[6-(allyl-methyl-amino)-hexyloxy]-phenyl}-methyl-carbamic acid 4-nitro-phenyl ester HCl | 442 | {4-[6-(Allyl-methyl-amino)-hexyloxy]-phenyl}-methyl-amine; 68–7967 | 4-Nitrophenyl-chloroformate |
| 4.5 | {4-[6-(Allyl-methyl-amino)-hexyloxy]-phenyl}-methyl-carbamic acid isobutyl ester; Hcl | 377 | {4-[6-(Allyl-methyl-amino)-hexyloxy]-phenyl}-methyl-amine; 68–7967 | Isobutyl-chloroformate |
| 4.6 | {4-[6-(Allyl-methyl-amino)-hexyloxy]-phenyl}-methyl-carbamic acid vinyl ester; Hcl | 347 | {4-[6-(Allyl-methyl-amino)-hexyloxy]-phenyl}-methyl-amine; 68–7967 | Vinylchloroformate |
| 4.7 | {4-[6-(Allyl-methyl-amino)-hexyloxy]-phenyl}-methyl-carbamic acid benzyl ester; HCl | 411 | {4-[6-(Allyl-methyl-amino)-hexyloxy]-phenyl}-methyl-amine; 68–7967 | Benzyl-chloroformate |
| 4.8 | {4-[6-(Allyl-methyl-amino)-hexyloxy]-phenyl}-methyl-carbamic acid allyl ester; HCl | 361 | {4-[6-(Allyl-methyl-amino)-hexyloxy]-phenyl}-methyl-amine; 68–7967 | Allylchloroformate |

-continued

| Example | Product | MS MH+ | Amine (educt) | Chloroformate (educt) |
|---------|---------|--------|---------------|------------------------|
| 4.9 | {4-[6-(Allyl-methyl-amino)-hexyloxy]-phenyl}-methyl-carbamic acid phenyl ester; HCl | 397 | {4-[6-(Allyl-methyl-amino)-hexyloxy]-phenyl}-methyl-amine; 68–7967 | Phenyl-chloroformate |
| 4.10 | {4-[6-(Allyl-methyl-amino)-hexyloxy]-phenyl}-methyl-carbamic acid butyl ester; HCl | 377 | {4-[6-(Allyl-methyl-amino)-hexyloxy]-phenyl}-methyl-amine; 68–7967 | Butylchloroformate |
| 4.11 | 4-({4-[6-(Allyl-methyl-amino)-hexyloxy]-phenyl}-methyl-carbamoyloxy)-benzoic acid methyl ester; HCl | 455 | {4-[6-(Allyl-methyl-amino)-hexyloxy]-phenyl}-methyl-amine; 68–7967 | 4-Methoxy-carbonylphenyl-chloroformate |
| 4.12 | {4-[6-(Allyl-methyl-amino)-hexyloxy]-phenyl}-methyl-carbamic acid p-tolyl ester; HCl | 411 | {4-[6-(Allyl-methyl-amino)-hexyloxy]-phenyl}-methyl-amine; 68–7967 | 4-Tosyl-chloroformate |
| 4.13 | {4-[6-(Allyl-methyl-amino)-hexyloxy]-phenyl}-methyl-carbamic acid 4-bromo-phenylester; HCl | 475 (1 Br) | {4-[6-(Allyl-methyl-amino)-hexyloxy]-phenyl}-methyl-amine; 68–7967 | 4-Bromphenyl-chloroformate |
| 4.14 | {4-[6-(Allyl-methyl-amino)-hexyloxy]-phenyl}-methyl-carbamic acid 4-fluoro-phenyl ester; HCl | 415 | {4-[6-(Allyl-methyl-amino)-hexyloxy]-phenyl}-methyl-amine; 68–7967 | 4-Fluorophenylchloroformate |
| 4.15 | {4-[6-(Allyl-methyl-amino)-hexyloxy]-phenyl}-methyl-carbamic acid 4-chloro-phenyl ester; HCL | 431 (1 Cl) | {4-[6-(Allyl-methyl-amino)-hexyloxy]-phenyl}-methyl-amine; 68–7967 | 4-Chlorophenyl-chloroformate |
| 4.16 | {4-[6-(Allyl-methyl-amino)-hexyloxy]-phenyl}-methyl-carbamic acid hexyl ester; HCl | 405 | {4-[6-(Allyl-methyl-amino)-hexyloxy]-phenyl}-methyl-amine; 68–7967 | Hexylchloroformate |
| 4.17 | {4-[6-(Allyl-methyl-amino)-hexyloxy]-phenyl}-methyl-carbamic acid 4-methoxy-phenyl ester; HCl | 427 | {4-[6-(Allyl-methyl-amino)-hexyloxy]-phenyl}-methyl-amine; 68–7967 | 4-Methoxyphenyl-chloroformate |

Example 5

A solution of 1.5 mmol trichloromethyl-chloroformate (diphosgene) in 20 ml $CH_2Cl_2$ was treated at 0° C. with 3 mmol phenol and 3 mmol quinoline and then stirred for 3 h at room temperature. The reaction was then cooled (0° C.) and a solution of 1 mmol amine and 2.5 mmol pyridine in 3 ml $CH_2Cl_2$ was added, followed by 1 mmol DMAP. The mixture was stirred over night at room temperature, treated with 0.15 ml formic acid and purified by preparative HPLC [RP-18, acetonitrile (0.1% HCOOH)/water (0.1% HCOOH), 10% to 95% acetonitrile]. After evaporation the carbamate was received as a mixture of amino hydrochloride and formiate. The following compounds were obtained using the corresponding amines and phenoles:

Example 6

A solution of 0.143 mmol amine in 0.35 ml dry dioxane was treated with (0.46mmol; 3 equivalents) Hünigsbase and 0.18 mmol sulfonylchloride in 0.5 ml dry dioxane. The solution was allowed to stand over night at room temperature. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation, the sulfonamide was obtained as a mixture of amino hydrochloride and formiate. The following compounds were obtained using the corresponding amines and sulfonylchlorides:

| Example | Product | MS MH+ | Amine (educt) | Phenole (educt) |
|---------|---------|--------|---------------|-----------------|
| 5.1 | {4-[6-(Allyl-methyl-amino)-hexyloxy]-phenyl}-methyl-carbamic acid 4-trifluoro-methyl-phenyl ester; HCl | 465 | {4-[6-(Allyl-methyl-amino)-hexyloxy]-phenyl}-methyl-amine | 4-Trifluoromethyl-phenol |
| 5.2 | {4-[6-(Allyl-methyl-amino)-hexyloxyl]-phenyl}-methyl-carbamic acid 4-acetyl-amino-phenyl ester; HCl | 454 | {4-[6-(Allyl-methyl-amino)-hexyloxy]-phenyl}-methyl-amine | 4-Acetamidophenol |

| Example | Product | MS MH+ | Amine (educt) | Sulfonylchloride (educt) |
|---|---|---|---|---|
| 6.1 | 5-Chloro-thiophene-2-sulfonic acid {4-[6-(allyl-methyl-amino)-hexyloxy]-phenyl}-methyl-amide; HCl | 457 (1 Cl) | {4-[6-(Allyl-methyl-amino)-hexyloxy]-phenyl}-methyl-amine | 5-Chlorothiophene-2-sulphonylchloride |
| 6.2 | N-{4-[6-(Allyl-methyl-amino)-hexyloxy]-phenyl}-4,N-dimethyl-benzenesulfonamide; HCl | 431 | {4-[6-(Allyl-methyl-amino)-hexyloxy]-phenyl}-methyl-amine | 4-Tosylsulphonyl-chloride |
| 6.3 | Naphthalene-2-sulfonic acid {4-[6-(allyl-methyl-amino)-hexyloxy]-phenyl}-methyl-amide; HCl | 467 | {4-[6-(Allyl-methyl-amino)-hexyloxy]-phenyl}-methyl-amine | 2-Naphthyl-sulphonylchloride |
| 6.4 | Quinoline-8-sulfonic acid {4-[6-(allyl-methyl-amino)-hexyloxy]-phenyl}-methyl-amide; HCl | 468 | {4-[6-(Allyl-methyl-amino)-hexyloxy]-phenyl}-methyl-amine | 8-Quinoline-sulphonylchloride |
| 6.5 | N-{4-[6-(Allyl-methyl-amino)-hexyloxy]-phenyl}-N-methyl-C-phenyl-methanesulfonamide; HCl | 431 | {4-[6-(Allyl-methyl-amino)-hexyloxy]-phenyl}-methyl-amine | Benzenesulphonyl-chloride |
| 6.6 | 3,5-Dimethyl-isoxazole-4-sulfonic acid {4-[6-(allyl-methyl-amino)-hexyloxy]-phenyl}-methyl-amide; HCl | 436 | {4-[6-(Allyl-methyl-amino)-hexyloxy]-phenyl}-methyl-amine | 3,5 Dimethyl-isoxazolsulphonylchloride |
| 6.7 | Naphthalene-1-sulfonic acid {4-[6-(allyl-methyl-amino)-hexyloxy]-phenyl}-methyl-amide; HCl | 467 | {4-[6-(Allyl-methyl-amino)-hexyloxy]-phenyl}-methyl-amine | 1-Naphthy-lsulphonylchloride |
| 6.8 | N-{4-[6-(Allyl-methyl-amino)-hexyloxy]-phenyl}-4-methoxy-N-methyl-benzenesulfonamide; HCl | 447 | {4-[6-(Allyl-methyl-amino)-hexyloxy]-phenyl}-methyl-amine | 4-Methoxybenzene-sulphonylchloride |
| 6.9 | N-{4-[6-(Allyl-methyl-amino)-hexyloxy]-phenyl}-N-methyl-benzenesulfonamide; HCl | 417 | {4-[6-(Allyl-methyl-amino)-hexyloxy]-phenyl}-methyl-amine | Benzenesulphonyl-chloride |
| 6.10 | N-{4-[6-(Allyl-methyl-amino)-hexyloxy]-phenyl}-4-fluoro-N-methyl-benzenesulfonamide; HCl | 435 | {4-[6-(Allyl-methyl-amino)-hexyloxy]-phenyl}-methyl-amine | 4-Fluorobenzene-sulphonylchloride |
| 6.11 | Thiophene-2-sulfonic acid {4-[6-(allyl-methyl-amino)-hexyloxy]-phenyl}-methyl-amide; HCl | 423 | {4-[6-(Allyl-methyl-amino)-hexyloxy]-phenyl}-methyl-amine | 2-Thiophene-sulphonylchloride |
| 6.12 | N-{4-[6-(Allyl-methyl-amino)-hexyloxy]-phenyl}-2-fluoro-N-methyl-benzenesulfonamide; HCl | 435 | {4-[6-(Allyl-methyl-amino)-hexyloxy]-phenyl}-methyl-amine | 2-Fluorobenzene-sulphonylchloride |
| 6.13 | N-{4-[6-(Allyl-methyl-amino)-hexyloxy]-phenyl}-4-tert-butyl-N-methyl-benzenesulfonamide; HCl | 473 | {4-[6-(Allyl-methyl-amino)-hexyloxy]-phenyl}-methyl-amine | 4-tert.-Butyl-benzenesulphonyl-chloride |
| 6.14 | N-{4-[6-(Allyl-methyl-amino)-hexyloxy]-phenyl}-4-butoxy-N-methyl-benzenesulfonamide; HCl | 489 | {4-[6-(Allyl-methyl-amino)-hexyloxy]-phenyl}-methyl-amine | 4-Butoxybenzene-sulphonylchloride |
| 6.15 | N-{4-[6-(Allyl-methyl-amino)-hexyloxy]-phenyl}-4-chloro-N-methyl-benzenesulfonamide; HCl | 451 (1 Cl) | {4-[6-(Allyl-methyl-amino)-hexyloxy]-phenyl}-methyl-amine | 4-Chlorobenzene-sulphonylchloride |
| 6.16 | N-{4-[6-(Allyl-methyl-amino)-hexyloxy]-phenyl}-N-methyl-4-trifluoromethyl-benzenesulfonamide; HCl | 485 | {4-[6-(Allyl-methyl-amino)-hexyloxy]-phenyl}-methyl-amine | 4-Trifluoromethyl-benzenesulphonyl-chloride |
| 6.17 | N-{4-[6-(Allyl-methyl-amino)-hexyloxy]-phenyl}-4-bromo-N-methyl-benzenesulfonamide; HCl | 495 (1 Br) | {4-[6-(Allyl-methyl-amino)-hexyloxy]-phenyl}-methyl-amine | 4-Brombenzene-sulphonylchloride |

Example 7

A solution of 0.133 mmol amine in 0.5 ml dry DMF was treated subsequently with 0.17 mmol (1.3 equivalents) acid, 0.266 mmol (2 equivalents) Hünigsbase, 0.266 mmol (2 equivalents) N-(3-Dimethylaminopropyl)-N'-ethylcarbodiimide hydrochloride) (EDCI) as well as catalytic amount of Hydroxybenzotriazole (HOBt) (approximately 0.02 mmol). The solution was allowed to stand over night at room temperature. The resulting reaction mixture was treated with 0.15 ml formic acid and purified by preparative HPLC [RP-18, acetonitrile (0.1% HCOOH)/water (0.1% HCOOH), 10% to 95% acetonitrile]. After evaporation, the amide was received as a mixture of amino hydrochloride and formiate.

The following compounds were obtained using the corresponding amines and acids:

| Example | Product | MS MH+ | Amine (educt) | Acid (educt) |
|---|---|---|---|---|
| 7.1 | 1H-Indole-2-carboxylic acid {4-[6-(allyl-methyl-amino)-hexyloxy]-phenyl}-methyl-amide; HCl | 420 | {4-[6-(Allyl-methyl-amino)-hexyloxy]-phenyl}-methyl-amine | 1H-Indole-2-carboxylicacid |
| 7.2 | N-{4-[6-(Allyl-methyl-amino)-hexyloxy]-phenyl}-4-chloro-N-methyl-benzamide; HCl | 415 (1 Cl) | {4-[6-(Allyl-methyl-amino)-hexyloxy]-phenyl}-methyl-amine | 4-Chloro-benzoicacid |
| 7.3 | N-{4-[6-(Allyl-methyl-amino)-hexyloxy]-phenyl}-4-fluoro-N-methyl-benzamide; HCl | 399 | {4-[6-(Allyl-methyl-amino)-hexyloxy]-phenyl}-methyl-amine | 4-Fluoro-benzoicacid |
| 7.4 | N-{4-[6-(Allyl-methyl-amino)-hexyloxy]-phenyl}-4-bromo-N-methyl-benzamide; HCl | 459 (1 Br) | {4-[6-(Allyl-methyl-amino)-hexyloxy]-phenyl}-methyl-amine | 4-Bromo-benzoicacid |
| 7.5 | N-{4-[6-(Allyl-methyl-amino)-hexyloxy]-phenyl}-N-methyl-4-trifluoro-methyl-benzamide; HCl | 449 | {4-[6-(Allyl-methyl-amino)-hexyloxy]-phenyl}-methyl-amine | 4-Trifluoromethyl-benzoicacid |
| 7.6 | Thiophene-3-carboxylic acid {4-[6-(allyl-methyl-amino)-hexyloxy]-phenyl}-methyl-amide; HCl | 387 | {4-[6-(Allyl-methyl-amino)-hexyloxy]-phenyl}-methyl-amine | Thiophene-3-carboxylicacid |
| 7.7 | 5-Bromo-thiophene-2-carboxylic acid {4-[6-(allyl-methyl-amino)-hexyloxy]-phenyl}-methyl-amide; HCl | 465 | {4-[6-(Allyl-methyl-amino)-hexyloxy]-phenyl}-methyl-amine | 5-Bromothiophene-2 carboxylicacid |
| 7.8 | N-{4-[6-(Allyl-methyl-amino)-hexyloxy]-phenyl}-N-methyl-2-thiophen-3-yl-acetamide; HCl | 401 | {4-[6-(Allyl-methyl-amino)-hexyloxy]-phenyl}-methyl-amine | Thiophene-3-aceticacid |
| 7.9 | N-{4-[6-(Allyl-methyl-amino)-hexyloxy]-phenyl}-2-(2,4-difluoro-phenyl)-N-methyl-acetamide; HCl | 431 | {4-[6-(Allyl-methyl-amino)-hexyloxy]-phenyl}-methyl-amine | 2,4-Difluoro-aceticacid |
| 7.10 | 5-Fluoro-1H-indole-2-carboxylic acid {4-[6-(allyl-methyl-amino)-hexyloxy]-phenyl}-methyl-amide; HCl | 438 | {4-[6-(Allyl-methyl-amino)-hexyloxy]-phenyl}-methyl-amine | 1H-Indole-5-Fluoro-2-carboxylicacid |
| 7.11 | N-{4-[6-(Allyl-methyl-amino)-hexyloxy]-phenyl}-2-(4-fluoro-phenyl)-N-methyl-acetamide; HCl | 413 | {4-[6-(Allyl-methyl-amino)-hexyloxy]-phenyl}-methyl-amine | 4-Fluorophenyl-aceticacid |
| 7.12 | 1H-Indole-5-carboxylic acid {4-[6-(allyl-methyl-amino)-hexyloxy]-phenyl}-methyl-amide; HCl | 420 | {4-[6-(Allyl-methyl-amino)-hexyloxy]-phenyl}-methyl-amine | 1H-Indole-5-carboxylicacid |
| 7.13 | N-{4-[6-(Allyl-methyl-amino)-hexyloxy]-phenyl}-3-chloro-N-methyl-benzamide; HCl | 415 | {4-[6-(Allyl-methyl-amino)-hexyloxy]-phenyl}-methyl-amine | 3-Chloro-benzoicacid |
| 7.14 | N-{4-[6-(Allyl-methyl-amino)-hexyloxy]-phenyl}-4-fluoro-3,N-dimethyl-benzamide; HCl | 413 | {4-[6-(Allyl-methyl-amino)-hexyloxy]-phenyl}-methyl-amine | 4-Fluor-3-Methyl-benzoicacid |
| 7.15 | N-{4-[6-(Allyl-methyl-amino)-hexyloxy]-phenyl}-N-methyl-4-nitro-benzamide; HCl | 426 | {4-[6-(Allyl-methyl-amino)-hexyloxy]-phenyl}-methyl-amine | 4-Nitrobenzoicacid |
| 7.16 | N-{4-[6-(Allyl-methyl-amino)-hexyloxy]-phenyl}- | 395 | {4-[6-(Allyl-methyl-amino)-hexyloxy]- | p-Toluicacid |

| Example | Product | MS MH+ | Amine (educt) | Acid (educt) |
|---|---|---|---|---|
| | 4,N-dimethyl-benzamide; HCl | | phenyl}-methyl-amine | |
| 7.17 | N-{4-[6-(Allyl-methyl-amino)-hexyloxy]-phenyl}-3-cyano-N-methyl-benzamide; HCl | 406 | {4-[6-(Allyl-methyl-amino)-hexyloxy]-phenyl}-methyl-amine | 3-Cyanobenzoicacid |
| 7.18 | N-{4-[6-(Allyl-methyl-amino)-hexyloxy]-phenyl}-3,N-dimethyl-benzamide; HCl | 395 | {4-[6-(Allyl-methyl-amino)-hexyloxy]-phenyl}-methyl-amine | m-Toluoicacid |
| 7.19 | N-{4-[6-(Allyl-methyl-amino)-hexyloxy]-phenyl}-3,4-dimethoxy-N-methyl-benzamide; HCl | 441 | {4-[6-(Allyl-methyl-amino)-hexyloxy]-phenyl}-methyl-amine | 3,4 Dimethoxy-benzoicacid |
| 7.20 | N-{4-[6-(Allyl-methyl-amino)-hexyloxy]-phenyl}-4-methoxy-N-methyl-benzamide; HCL | 411 | {4-[6-(Allyl-methyl-amino)-hexyloxy]-phenyl}-methyl-amine | 4-Methoxy-benzoicacid |
| 7.21 | N-{4-[6-(Allyl-methyl-amino)-hexyloxy]-phenyl}-4-fluoro-N-methyl-3-nitro-benzamide; HCl | 444 | {4-[6-(Allyl-methyl-amino)-hexyloxy]-phenyl}-methyl-amine | 4-Fluoro-3-nitro-benzoicacid |
| 7.22 | 4-Acetyl-N-{4-[6-(allyl-methyl-amino)-hexyloxy]-phenyl}-N-methyl-benzamide; HCl | 423 | {4-[6-(Allyl-methyl-amino)-hexyloxy]-phenyl}-methyl-amine | 4-Acetylbenzoicacid |
| 7.23 | N-{4-[6-(Allyl-methyl-amino)-hexyloxy]-phenyl}-N-methyl-nicotinamide; HCl | 382 | {4-[6-(Allyl-methyl-amino)-hexyloxy]-phenyl}-methyl-amine | Nicotinicacid |
| 7.24 | N-{4-[6-(Allyl-methyl-amino)-hexyloxy]-phenyl}-N-methyl-benzamide; HCl | 381 | {4-[6-(Allyl-methyl-amino)-hexyloxy]-phenyl}-methyl-amine | Benzoicacid |
| 7.25 | Pyridine-2-carboxylic acid {4-[6-(allyl-methyl-amino)-hexyloxy]-phenyl}-methyl-amide; HCl | 382 | {4-[6-(Allyl-methyl-amino)-hexyloxy]-phenyl}-methyl-amine | Picolinicacid |

Example 8

A solution of 0.133 mmol amine was treated with 0.17 mmol (1.3 equivalents) isothiocyanate in 0.35 ml dry dioxane. The solution was allowed to stand over night at room temperature, treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the thiourea was received as amino formiate. The following compounds were obtained using the corresponding isothiocyanates and {4-[6-(Allyl-methyl-amino)-hexyloxy]-phenyl}-methyl-amine as the amine:

| Example | Product | MS MH+ | Isothiocyanate (educt) |
|---|---|---|---|
| 8.1 | 1-{4-[6-(Allyl-methyl-amino)-hexyloxy]-phenyl}-3-(2-bromo-4-fluoro-phenyl)-1-methyl-thiourea; compound with formic acid | 508 (1 Br) | 2-Bromo-4-fluoro-phenylisothiocyanate |
| 8.2 | 1-{4-[6-(Allyl-methyl-amino)-hexyloxy]-phenyl}-3-(4-bromo-2-methyl-phenyl)-1-methyl-thiourea; compound with formic acid | 504 (1 Br) | 4-Bromo-2-methyl-phenylisothiocyanate |
| 8.3 | 1-{4-[6-(Allyl-methyl-amino)-hexyloxy]-phenyl}-1-methyl-3-(4-trifluoromethyl-phenyl)-thiourea; compound with formic acid | 480 | 4-Trifluoromethyl-phenylisothiocyanate |
| 8.4 | 1-{4-[6-(Allyl-methyl-amino)-hexyloxy]-phenyl}-3-(4-chloro-phenyl)-1-methyl-thiourea; compound with formic acid | 446 (1 Cl) | 4-Chloro-phenylisothiocyanate |
| 8.5 | 1-{4-[6-(Allyl-methyl-amino)-hexyloxy]-phenyl}-3-(4-methoxy-phenyl)-1-methyl-thiourea; compound with formic acid | 442 | 4-Methoxy-phenylisothiocyanate |
| 8.6 | 1-{4-[6-(Allyl-methyl-amino)-hexyloxy]-phenyl}-3-(4-cyano-phenyl)-1-methyl-thiourea; compound with formic acid | 437 | 4-Cyano-phenylisothiocyanate |

-continued

| Example | Product | MS MH+ | Isothiocyanate (educt) |
|---|---|---|---|
| 8.7 | 1-{4-[6-(Allyl-methyl-amino)-hexyloxy]-phenyl}-1-methyl-3-(3-methyl-butyl)-thiourea; compound with formic acid | 406 | 3-Methyl-butylisothiocyanate |
| 8.8 | 1-{4-[6-(Allyl-methyl-amino)-hexyloxy]-phenyl}-3-sec-butyl-1-methyl-thiourea; compound with formic acid | 392 | sec-Butylisothiocyanate |
| 8.9 | 1-{4-[6-(Allyl-methyl-amino)-hexyloxy]-phenyl}-3-cyclopropyl-1-methyl-thiourea; compound with formic acid | 376 | Cyclopropylisothiocyanate |
| 8.10 | 1-{4-[6-(Allyl-methyl-amino)-hexyloxy]-phenyl}-3-(2,4-dichloro-benzyl)-1-methyl-thiourea; compound with formic acid | 494 (2 Cl) | 2,4-Dichloro-benzylisothiocyanate |
| 8.11 | 1-{4-[6-(Allyl-methyl-amino)-hexyloxy]-phenyl}-3-(5-chloro-2-methoxy-phenyl)-1-methyl-thiourea; compound with formic acid | 476 (1 Cl) | 5-Chloro-2-methoxy-phenylisothiocyanate |
| 8.12 | 1-{4-[6-(allyl-methyl-amino)-hexyloxy]-phenyl}-1-methyl-3-(2-methyl-5-nitro-phenyl)-thiourea; compound with formic acid | 471 | 2-Methyl-5-nitro-phenylisothiocyanate |
| 8.13 | 1-{4-[6-(Allyl-methyl-amino)-hexyloxy]-phenyl}-3-(2,3-dihydro-benzo [1,4] dioxin-6-yl)-1-methyl-thiourea; compound with formic acid | 470 | 2,3-Dihydro-benzo [1,4] dioxin-6-isothiocyanate |
| 8.14 | 1-{4-[6-(Allyl-methyl-amino)-hexyloxy]-phenyl}-3-(2-isopropyl-phenyl)-1-methyl-thiourea; compound with formic acid | 454 | 2-Isopropyl-phenylisothiocyanate |
| 8.15 | 1-{4-[6-(Allyl-methyl-amino)-hexyloxy]-phenyl}-1-methyl-3-(3-phenyl-propyl)-thiourea; compound with formic acid | 454 | 3-Phenyl-propylisothiocyanate |
| 8.16 | 3-(4-Acetyl-phenyl)-1-{4-[6-(allyl-methyl-amino)-hexyloxy]-phenyl}-1-methyl-thiourea; compound with formic acid | 454 | 4-Acetyl-phenylisothiocyanate |
| 8.17 | 1-{4-[6-(Allyl-methyl-amino)-hexyloxy]-phenyl}-3-cyclohexylmethyl-1-methyl-thiourea; compound with formic acid | 432 | Cyclohexylmethylisothiocyanate |
| 8.18 | 1-{4-[6-(Allyl-methyl-amino)-hexyloxy]-phenyl}-1-methyl-3-(tetrahydro-furan-2-ylmethyl)-thiourea; compound with formic acid | 420 | Tetrahydro-furan-2-ylmethylisothiocyanate |
| 8.19 | 1-{4-[6-(Allyl-methyl-amino)-hexyloxy]-phenyl}-3-furan-2-ylmethyl-1-methyl-thiourea; compound with formic acid | 416 | Furan-2-ylmethylisothiocyanate |
| 8.20 | 1-{4-[6-(Allyl-methyl-amino)-hexyloxy]-phenyl}-3-cyclopentyl-1-methyl-thiourea; compound with formic acid | 404 | Cyclopentylisothiocyanate |
| 8.21 | 1-{4-[6-(Allyl-methyl-amino)-hexyloxy]-phenyl}-3-bicyclo [2.2.1]hept-2-yl-1-methyl-thiourea; compound with formic acid | 430 | Bicyclo [2.2.1]hept-2-isothiocyanate |
| 8.22 | 1-{4-[6-(Allyl-methyl-amino)-hexyloxy]-phenyl}-1-methyl-3-(2,3,5,6-tetrafluoro-phenyl)-thiourea; compound with formic acid | 484 | 2,3,5,6-Tetrafluoro-phenylisothiocyanate |
| 8.23 | 1-{4-[6-(Allyl-methyl-amino)-hexyloxy]-phenyl}-3-[1-(4-fluoro-phenyl)-ethyl]-1-methyl-thiourea; compound with formic acid | 458 | 4-Fluoro-phenylisothiocyanate |
| 8.24 | 1-{4-[6-(Allyl-methyl-amino)-hexyloxy]-phenyl}-3-(4-tert-butyl-phenyl)-1-methyl-thiourea; compound with formic acid | 468 | 4-tert-Butyl-phenylisothiocyanate |
| 8.25 | 1-{4-[6-(Allyl-methyl-amino)-hexyloxy]-phenyl}-1-methyl-3-(2,3,4-trimethoxy-benzyl)-thiourea; compound with formic acid | 516 | 2,3,4-Trimethoxy-benzylisothiocyanate |
| 8.26 | 1-{4-[6-(Allyl-methyl-amino)-hexyloxy]-phenyl}-3-(3-chloro-4-methyl-benzyl)-1-methyl-thiourea; compound with formic acid | 474 (1 Cl) | 3-Chloro-4-methyl-benzylisothiocyanate |
| 8.27 | 1-{4-[6-(Allyl-methyl-amino)-hexyloxy]-phenyl}-1-methyl-3-pyridin-3-yl-thiourea; compound with formic acid | 413 | Pyridin-3-isothiocyanate |
| 8.28 | 1-{4-[6-(Allyl-methyl-amino)-hexyloxy]-phenyl}-3-benzo [1,3] dioxol-5-ylmethyl-1-methyl-thiourea; compound with formic acid | 470 | Benzo [1,3] dioxol-5-ylmethylisothiocyanate |
| 8.29 | 1-{4-[6-(Allyl-methyl-amino)-hexyloxy]-phenyl}-1-methyl-3-(4-methylsulfanyl-phenyl)-thiourea; compound with formic acid | 458 | 4-Methylsulfanyl-phenylisothiocyanate |
| 8.30 | 1-{4-[6-(Allyl-methyl-amino)-hexyloxy]-phenyl}-3-cycloheptyl-1-methyl-thiourea; compound with formic acid | 432 | Cycloheptylisothiocyanate |
| 8.31 | 1-{4-[6-(Allyl-methyl-amino)-hexyloxy]-phenyl}-3-(2-chloro-5-trifluoromethyl- | 514 (1 Cl) | 2-Chloro-5-trifluoromethyl- |

-continued

| Example | Product | MS MH+ | Isothiocyanate (educt) |
|---|---|---|---|
| | phenyl)-1-methyl-thiourea; compound with formic acid | | phenylisothiocyanate |
| 8.32 | 1-{4-[6-(Allyl-methyl-amino)-hexyloxy]-phenyl}-1-methyl-3-naphthalen-1-yl-thiourea; compound with formic acid | 462 | Naphthalen-1-isothiocyanate |
| 8.33 | 1-{4-[6-(Allyl-methyl-amino-hexyloxy]-phenyl}-3-(2-cyclohex-1-enyl-ethyl-1-methyl-thiourea; compound with formic acid | 444 | 1-(2-Isothiocyanato-ethyl)-cyclohexene |
| 8.34 | (3-{4-[6-(Allyl-methyl-amino-hexyloxy]-phenyl}-3-methyl-thioureido-acetic acid methyl ester; compound with formic acid | 408 | Isothiocyanato-acetic acid methyl ester |
| 8.35 | 1-{4-[6-(Allyl-methyl-amino-hexyloxy]-phenyl}-3-ethyl-1-methyl-thiourea; compound with formic acid | 364 | Isothiocyanato-ethane |
| 8.36 | 1-{4-[6-(Allyl-methyl-amino-hexyloxy]-phenyl}-3-hexyl-1-methyl-thiourea; compound with formic acid | 420 | Isothiocyanato-hexane |
| 8.37 | 1-{4-[6-(Allyl-methyl-amino-hexyloxy]-phenyl}-3-butyl-1-methyl-thiourea; compound with formic acid | 392 | Isothiocyanato-butane |
| 8.38 | 1-{4-[6-(Allyl-methyl-amino-hexyloxy]-phenyl}-1-methyl-3-(2-methyl-butyl-thiourea; compound with formic acid | 406 | 1-Isothiocyanato-2-methyl-butane |
| 8.39 | 1-{4-[6-(Allyl-methyl-amino-hexyloxy]-phenyl}-3-(2-methoxy-ethyl-1-methyl-thiourea; compound with formic acid | 394 | 1-Isothiocyanato-2-methoxy-ethane |
| 8.40 | 1-{4-[6-(Allyl-methyl-amino-hexyloxy]-phenyl}-1-methyl-3-(3-methyl-butyl-thiourea; compound with formic acid | 406 | 1-Isothiocyanato-3-methyl-butane |
| 8.41 | 1-{4-[6-(Allyl-methyl-amino-hexyloxy]-phenyl}-1-methyl-3-phenyl-thiourea; compound with formic acid | 412 | Isothiocyanato-benzene |
| 8.42 | 4-(3-{4-[6-(Allyl-methyl-amino-hexyloxy]-phenyl}-3-methyl-thioureido-benzoic acid methyl ester; compound with formic acid | 470 | 4-Isothiocyanato-benzoic acid methyl ester |
| 8.43 | 1-{4-[6-(Allyl-methyl-amino-hexyloxy]-phenyl}-3-(4-butyl-phenyl-1-methyl-thiourea; compound with formic acid | 468 | 1-Butyl-4-isothiocyanato-benzene |
| 8.44 | 1-{4-[6-(Allyl-methyl-amino-hexyloxy]-phenyl}-3-benzyl-1-methyl-thiourea; compound with formic acid | 426 | Isothiocyanatomethyl-benzene |
| 8.45 | 1-{4-[6-(Allyl-methyl-amino-hexyloxy]-phenyl}-1-methyl-3-(4-methyl-benzyl-thiourea; compound with formic acid | 440 | 1-Isothiocyanatomethyl-4-methyl-benzene |
| 8.46 | 1-{4-[6-(Allyl-methyl-amino-hexyloxy]-phenyl}-3-(4-methoxy-benzyl-1-methyl-thiourea; compound with formic acid | 456 | 1-Isothiocyanatomethyl-4-methoxy-benzene |
| 8.47 | 1-{4-[6-(Allyl-methyl-amino-hexyloxy]-phenyl}-3-(4-fluoro-benzyl-1-methyl-thiourea; compound with formic acid | 444 | 1-Isothiocyanatomethyl-4-fluoro-benzene |
| 8.48 | 1-{4-[6-(Allyl-methyl-amino-hexyloxy]-phenyl}-3-(4-chloro-benzyl-1-methyl-thiourea; compound with formic acid | 460 (1 Cl) | 1-Isothiocyanatomethyl-4-chloro-benzene |
| 8.49 | 1-{4-[6-(Allyl-methyl-amino-hexyloxy]-phenyl}-1-methyl-3-(1-phenyl-ethyl-thiourea; compound with formic acid | 440 | (1-Isothiocyanato-ethyl)-benzene |
| 8.50 | 1-{4-[6-(Allyl-methyl-amino-hexyloxy]-phenyl}-3-[2-(4-chloro-phenyl-ethyl]-1-methyl-thiourea; compound with formic acid | 474 (1 Cl) | 1-Chloro-4-(2-isothiocyanato-ethyl)-benzene |
| 8.51 | 1-{4-[6-(Allyl-methyl-amino-hexyloxy]-phenyl}-1-methyl-3-phenethyl-thiourea; compound with formic acid | 440 | (2-Isothiocyanato-ethyl)-benzene |
| 8.52 | 1-{4-[6-(Allyl-methyl-amino-hexyloxy]-phenyl}-1-methyl-3-(2-p-tolyl-ethyl-thiourea; compound with formic acid | 454 | 1-(2-Isothiocyanato-ethyl)-4-methyl-benzene |
| 8.53 | 1-{4-[6-(Allyl-methyl-amino-hexyloxy]-phenyl}-3-cyclohexyl-1-methyl-thiourea; compound with formic acid | 418 | Isothiocyanato-cyclohexane |

Example 9

A solution of 0.14 mmol amine in 0.5 ml dry dioxane was treated with a solution of 0.14 mmol chlorothionoformate in 0.35 ml dry dioxane. The solution was allowed to stand over night at room temperature, treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the thiocarbamate was received as a mixture of amino hydrochloride and formiate. The following compounds were obtained using the corresponding chlorothionoformates and {4-[6-(Allyl-methyl-amino)-hexyloxy]-phenyl}-methyl-amine as the amine:

| Example | Product | MS MH$^+$ | Chlorothionoformate (educt) |
|---|---|---|---|
| 9.1 | {4-[6-(Allyl-methyl-amino)-hexyloxy]-phenyl}-methyl-thiocarbamic acid O-(4-chloro-phenyl) ester; compound with formic acid | 447 (1 Cl) | 4-Chlorophenyl chlorothionoformiate |
| 9.2 | {4-[6-(Allyl-methyl-amino)-hexyloxy]-phenyl}-methyl-thiocarbamic acid O-pentafluorophenyl ester; compound with formic acid | 503 | Pentafluorophenyl chlorothionoformiate |
| 9.3 | {4-[6-(Allyl-methyl-amino)-hexyloxy]-phenyl}-methyl-thiocarbamic acid O-(2,4,6-trichloro-phenyl) ester; compound with formic acid | 515 (3 Cl) | 2,4,6-Trichlorophenyl chlorothionoformiate |
| 9.4 | {4-[6-(Allyl-methyl-amino)-hexyloxy]-phenyl}-methyl-thiocarbamic acid O-(4-fluoro-phenyl) ester; compound with formic acid | 431 | 4-Fluorophenyl chlorothionoformiate |

Example 10

A solution of 0.135 mmol amine in 0.75 ml dry dioxane was treated with 5 equivalents of triethylamine followed by a solution of 0.175 mmol (1.3 equivalente) sulfamoylchloride in 0.25 ml dry dioxane. The suspension was allowed to stand over night at room temperature, treated with 0.15 ml formic acid and purified by preparative HPLC [RP-18, acetonitrile (0.1% HCOOH)/water (0.1% HCOOH), 10% to 95% acetonitrile]. After evaporation of the corresponding fraction, the sulfamide was received as a mixture of amino hydrochloride and formiate. The following compounds were obtained using the corresponding amines and sulfamoyl-chlorides:

| Example | Product | MS MH$^+$ | Amine (educt) | Sulfamoylchloride (educt) |
|---|---|---|---|---|
| 10.1 | {4-[6-(Allyl-methyl-amino)-hexyloxy]-phenyl}-methyl-sulfamic acid benzyl amide; compound with formic acid | 446 | {4-[6-(Allyl-methyl-amino)-hexyloxy]-phenyl}-methyl-amine | Benzylsulfamoyl-chloride |
| 10.2 | {4-[6-(Allyl-methyl-amino)-hexyloxy]-phenyl}-methyl-sulfamic acid phenyl amide; compound with formic acid | 432 | {4-[6-(Allyl-methyl-amino)-hexyloxy]-phenyl]-methyl-amine | Phenylsulfamoyl-chloride |
| 10.3 | {4-[6-(Allyl-methyl-amino)-hexyloxy]-phenyl}-methyl-sulfamic acid furan-2-ylmethyl amide; compound with formic acid | 436 | {4-[6-(Allyl-methyl-amino)-hexyloxy]-phenyl}-methyl-amine | Furan-2-ylmethyl-sulfamoylchloride |
| 10.4 | ({4-[6-(Allyl-methyl-amino)-hexyloxy]-phenyl}-methyl-sulfonylamino)-acetic acid ethyl ester; compound with formic acid | 442 | {4-[6-(Allyl-methyl-amino)-hexyloxy]-phenyl}-methyl-amine | Chlorosulfonyl-amino-acetic acid ethyl ester |
| 10.5 | {4-[6-(Allyl-methyl-amino)-hexyloxy]-phenyl}-methyl-sulfamic acid 2,2,2-trifluoro-ethyl amide; compound with formic acid | 438 | {4-[6-(Allyl-methyl-amino)-hexyloxy]-phenyl}-methyl-amine | 2,2,2-Trifluoro-ethylsulfamoylchloride |
| 10.6 | {4-[6-(Allyl-methyl-amino)-hexyloxy]-phenyl}-methyl-sulfamic acid benzo[1,3]dioxol-5-ylmethyl amide; compound with formic acid | 490 | {4-[6-(Allyl-methyl-amino)-hexyloxy]-phenyl}-methyl-amine | Benzo[1,3]dioxol-5-ylmethylsulfamoyl chloride |
| 10.7 | {4-[6-(Allyl-methyl-amino)-hexyloxy]-phenyl}-methyl-sulfamic acid phenethyl amide; compound with formic acid | 460 | {4-[6-(Allyl-methyl-amino)-hexyloxy]-phenyl}-methyl-amine | Phenethylsulfamoyl chloride |
| 10.8 | {4-[6-(Allyl-methyl-amino)-hexyloxy]-phenyl}-methyl-sulfamic acid cyclopropyl | 396 | {4-[6-(Allyl-methyl-amino)-hexyloxy]-phenyl]-methyl- | Cyclopropyl-sulfamoylchloride |

-continued

| Example | Product | MS MH+ | Amine (educt) | Sulfamoylchloride (educt) |
|---|---|---|---|---|
| | amide; compound with formic acid | | amine | |
| 10.9 | {4-[6-(Allyl-methyl-amino)-hexyloxy]-phenyl}-methyl-sulfamic acid 2,2,2-trifluoro-ethyl amide; compound with formic acid | 438 | {4-[6-(Allyl-methyl-amino)-hexyloxy]-phenyl}-methyl-amine | 2,2,2-Trifluoro-ethylsulfamoylchloride |
| 10.10 | {4-[6-(Allyl-methyl-amino)-hexyloxy]-phenyl}-methyl-sulfamic acid 4-chloro-phenyl amide; compound with formic acid | 466 (1 Cl) | {4-[6-(Allyl-methyl-amino)-hexyloxy]-phenyl}-methyl-amine | 4-Chloro-phenyl-sulfamoyl chloride |
| 10.11 | {4-[6-(Allyl-methyl-amino)-hexyloxy]-phenyl}-methyl-sulfamic acid 4-bromo-phenyl amide; compound with formic acid | 510 (1 Br) | {4-[6-(Allyl-methyl-amino)-hexyloxy]-phenyl}-methyl-amine | 4-Bromo-phenyl-sulfamoyl chloride |
| 10.12 | {4-[6-(Allyl-methyl-amino)-hexyloxy]-phenyl}-methyl-sulfamic acid p-tolyl amide; compound with formic acid | 446 | {4-[6-(Allyl-methyl-amino)-hexyloxy]-phenyl}-methyl-amine | 4-Methyl-phenyl-sulfamoyl chloride |
| 10.13 | {4-[6-(Allyl-methyl-amino)-hexyloxy]-phenyl}-methyl-sulfamic acid 4-trifluoromethyl-phenyl amide; compound with formic acid | 500 | {4-[6-(Allyl-methyl-amino)-hexyloxy]-phenyl}-methyl-amine | 4-Trifluoromethyl-phenylsulfamoyl chloride |
| 10.14 | {4-[6-(Allyl-methyl-amino)-hexyloxyl-phenyl}-methyl-sulfamic acid 4-cyano-phenyl amide; compound with formic acid | 457 | {4-(6-(Allyl-methyl-amino)-hexyloxy]-phenyl}-methyl-amine | 4-Cyano-phenyl-sulfamoyl chloride |
| 10.15 | {4-[6-(Allyl-methyl-amino)-hexyloxy]-phenyl}-methyl-sulfamic acid 4-methoxy-phenyl amide; compound with formic acid | 462 | {4-[6-(Allyl-methyl-amino)-hexyloxy]-phenyl}-methyl-amine | 4-Methoxy-phenyl-sulfamoyl chloride |
| 10.16 | {4-[6-(Allyl-methyl-amino)-hexyloxy]-phenyl}-methyl-sulfamic acid 4-fluoro-phenyl amide; compound with formic acid | 450 | {4-(6-(Allyl-methyl-amino)-hexyloxy]-phenyl}-methyl-amine | 4-Fluoro-phenyl-sulfamoyl chloride |
| 10.17 | {4-[6-(Allyl-methyl-amino)-hexyloxy]-phenyl}-methyl-sulfamic acid 3,4-difluoro-phenyl amide; compound with formic acid | 468 | {4-[6-(Allyl-methyl-amino)-hexyloxy]-phenyl}-methyl-amine | 3,4-Difluoro-phenylsulfamoyl chloride |
| 10.18 | {4-[6-(Allyl-methyl-amino)-hexyloxy]-phenyl}-methyl-sulfamic acid 3-fluoro-phenyl amide; compound with formic acid | 450 | {4-[6-(Allyl-methyl-amino)-hexyloxy]-phenyl}-methyl-amine | 3-Fluoro-phenyl-sulfamoyl chloride |
| 10.19 | {4-[6-(Allyl-methyl-amino)-hexyloxy]-phenyl}-methyl-sulfamic acid 2,4-difluoro-phenyl amide; compound with formic acid | 468 | {4-[6-(Allyl-methyl-amino)-hexyloxy]-phenyl}-methyl-amine | 2,4-Difluoro-phenylsulfamoyl chloride |
| 10.20 | {4-[6-(Allyl-methyl-amino)-hexyloxy]-phenyl}-methyl-sulfamic acid 2,5-difluoro-phenyl amide; compound with formic acid | 468 | {4-[6-(Allyl-methyl-amino)-hexyloxy]-phenyl}-methyl-amine | 2,5-Difluoro-phenylsulfamoyl chloride |
| 10.21 | {4-[5-(Allyl-methyl-amino)-pentyloxy]-phenyl}-methyl-sulfamic acid (4-chloro-phenyl)-amide; compound with formic acid | 453 (1 Cl) | {4-[5-(Allyl-methyl-amino)-pentyloxy]-phenyl}-methyl-amine | 4-Chloro-phenyl-sulfamoyl chloride |
| 10.22 | {4-[4-(Allyl-methyl-amino)-butoxy]-phenyl}-methyl-sulfamic acid (4-chloro-phenyl)-amide; compound with formic acid | 438 (1 Cl) | {4-[4-(Allyl-methyl-amino)-butoxy]-phenyl}-methyl-amine | 4-Chloro-phenyl-sulfamoyl chloride |
| 10.23 | {4-[5-(Allyl-methyl-amino)-pentyloxy]-phenyl}-methyl-sulfamic acid (4-fluoro- | 436 | {4-[5-(Allyl-methyl-amino)-pentyloxy]-phenyl}-methyl- | 4-Fluoro-phenyl-sulfamoyl chloride |

-continued

| Example | Product | MS MH+ | Amine (educt) | Sulfamoylchloride (educt) |
|---|---|---|---|---|
| | phenyl)-amide; compound with formic acid | | amine | |
| 10.24 | {4-[4-(Allyl-methyl-amino) butoxy]-phenyl}-methyl-sulfamic acid (4-fluoro-phenyl)-amide; compound with formic acid | 422 | {4-[4-(Allyl-methyl-amino)-butoxy]-phenyl}-methyl-amine | 4-Fluoro-phenyl-sulfamoyl chloride |
| 10.25 | {4-[5-(Allyl-methyl-amino)-pentyloxy]-phenyl}-methyl-sulfamic acid (4-bromo-phenyl)-amide; compound with formic acid | 496 (1 Br) | {4-[5-(Allyl-methyl-amino)-pentyloxy]-phenyl}-methyl-amine | 4-Bromo-phenyl-sulfamoyl chloride |
| 10.26 | {4-[4-(Allyl-methyl-amino)-butoxy]-phenyl}-methyl-sulfamic acid (4-bromo-phenyl)-amide; compound with formic acid | 482 (1 Br) | {4-[4-(Allyl-methyl-amino)-butoxy]-phenyl}-methyl-amine | 4-Bromo-phenyl-sulfamoyl chloride |
| 10.27 | {4-[5-(Allyl-methyl-amino)-pentyloxy]-phenyl}-methyl-sulfamic acid p-tolyl-amide; compound with formic acid | 432 | {4-[5-(Allyl-methyl-amino)-pentyloxyl]-phenyl}-methyl-amine | p-tolylsulfamoyl chloride |
| 10.28 | {4-[4-(Allyl-methyl-amino)-butoxy]-phenyl}-methyl-sulfamic acid (p-tolyl)-amide; compound with formic acid | 418 | {4-[4-(Allyl-methyl-amino)-butoxy]-phenyl}-methyl-amine | p-tolylsulfamoyl chloride |
| 10.29 | {4-[5-(Allyl-methyl-amino)-pentyloxy]-phenyl}-methyl-sulfamic acid (3,4-difluoro-phenyl)-amide; compound with formic acid | 454 | {4-[5-(Allyl-methyl-amino)-pentyloxy]-phenyl}-methyl-amine | 3,4-Difluorophenyl-sulfamoyl chloride |
| 10.30 | {4-[4-(Allyl-methyl-amino)-butoxy]-phenyl}-methyl-sulfamic acid (3,4-difluoro-phenyl)-amide; compound with formic acid | 440 | {4-[4-(Allyl-methyl-amino)-butoxy]-phenyl}-methyl-amine | 3,4-Difluorophenyl-sulfamoyl chloride |
| 10.31 | {4-[5-(Allyl-methyl-amino)-pentyloxy]-phenyl}-methyl-sulfamic acid (4-trifluoromethyl-phenyl)-amide; compound with formic acid | 486 | {4-[5-(Allyl-methyl-amino)-pentyloxy]-phenyl}-methyl-amine | 4-Trifluoromethyl-phenylsulfamoyl chloride |
| 10.32 | {4-[4-(Allyl-methyl-amino)-butoxy]-phenyl}-methyl-sulfamic acid (4-trifluoromethyl-phenyl)-amide; compound with formic acid | 472 | {4-[4-(Allyl-methyl-amino)-butoxy]-phenyl}-methyl-amine | 4-Trifluoromethyl-phenylsulfamoyl chloride |
| 10.33 | {4-[4-(Allyl-methyl-amino)-butoxy]-phenyl}-methyl-sulfamic acid (3-fluoro-phenyl)-amide; compound with formic acid | 422 | {4-[4-(Allyl-methyl-amino)-butoxy]-phenyl}-methyl-amine | 3-Fluorophenyl-sulfamoyl chloride |
| 10.34 | {4-[5-(Allyl-methyl-amino)-pentyloxy]-phenyl}-methyl-sulfamic acid (4-cyano-phenyl)-amide; compound with formic acid | 453 | {4-[5-(Allyl-methyl-amino)-pentyloxy]-phenyl}-methyl-amine | 4-Cyanophenyl-sulfamoyl chloride |
| 10.35 | {4-[4-(Allyl-methyl-amino)-butoxy]-phenyl}-methyl-sulfamic acid (4-cyano-phenyl)-amide; compound with formic acid | 429 | {4-[4-(Allyl-methyl-amino)-butoxy]-phenyl}-methyl-amine | 4-Cyanophenyl-sulfamoyl chloride |
| 10.36 | {4-[5-(Allyl-methyl-amino)-pentyloxyl-phenyl}-methyl-sulfamic acid (2,4-difluoro-phenyl)-amide; compound with formic acid | 554 | {4-[5-(Allyl-methyl-amino)-pentyloxy]-phenyl}-methyl-amine | 2,4-Difluorophenyl-sulfamoyl chloride |
| 10.37 | {4-[4-(Allyl-methyl-amino)-butoxy]-phenyl}-methyl-sulfamic acid (2,4-difluoro-phenyl)-amide; compound with formic acid | 440 | {4-[4-(Allyl-methyl-amino)-butoxy]-phenyl}-methyl-amine | 2,4-Difluorophenyl-sulfamoyl chloride |
| 10.38 | {4-[5-(Allyl-methyl-amino)-pentyloxy]-phenyl}-methyl-sulfamic acid (4-methoxy- | 448 | {4-[5-(Allyl-methyl-amino)-pentyloxy]-phenyl}-methyl- | 4-Methoxyphenyl-sulfamoyl chloride |

-continued

| Example | Product | MS MH+ | Amine (educt) | Sulfamoylchloride (educt) |
|---|---|---|---|---|
| | phenyl)-amide; compound with formic acid | | amine | |
| 10.39 | {4-[4-(Allyl-methyl-amino)-butoxy]-phenyl}-methyl-sulfamic acid (4-methoxy-phenyl)-amide; compound with formic acid | 434 | {4-[4-(Allyl-methyl-amino)-butoxy]-phenyl}-methyl-amine | 4-Methoxyphenyl-sulfamoyl chloride |
| 10.40 | {4-[5-(Allyl-methyl-amino)-pentyloxy]-phenyl}-methyl-sulfamic acid (2,5-difluoro-phenyl)-amide; compound with formic acid | 454 | {4-[5-(Allyl-methyl-amino)-pentyloxy]-phenyl}-methyl-amine | 2,5-Difluorophenyl-sulfamoyl chloride |
| 10.41 | {4-[4-(Allyl-methyl-amino)-butoxy]-phenyl}-methyl-sulfamic acid (2,5-difluoro-phenyl)-amide; compound with formic acid | 440 | {4-[4-(Allyl-methyl-amino)-butoxy]-phenyl}-methyl-amine | 2,5-Difluorophenyl-sulfamoyl chloride |
| 10.42 | {4-[5-(Allyl-methyl-amino)-pentyloxy]-phenyl}-methyl-sulfamic acid (phenyl)-amide; compound with formic acid | 418 | {4-[5-(Allyl-methyl-amino)-pentyloxy]-phenyl}-methyl-amine | Phenylsulfamoyl chloride |
| 10.43 | {4-[4-(Allyl-methyl-amino)-butoxy]-phenyl}-methyl-sulfamic acid (phenyl)-amide; compound with formic acid | 404 | {4-[4-(Allyl-methyl-amino)-butoxy]-phenyl}-methyl-amine | Phenylsulfamoyl chloride |

Example 11

Sulfamoyl chlorides were prepared according to the following procedure. 3 equivalents of the corresponding amine were dissolved in $CH_2Cl_2$ (1 ml/mmol) and placed in an ice bath. A solution of chlorosulfonic acid (1 eq.) in $CH_2Cl_2$ (0.5 ml/mmol) was added slowly (30 min). The reaction mixture was stirred at 0° C. for a further 30 min. Afterwards, the ice bath was removed and the stirring was continued for 1 h at room temperature. The precipitate was collected by filtration and dried under high vacuum. This salt was suspended in toluene (1 ml/mmol amine) and $PCl_5$ (1 eq) was added. The mixture was stirred at 75° C. for 2 h, cooled to room temperature and filtered. The solid residue was washed with toluene. The filtrate was evaporated and dried under high vacuum. The crude sulfamoyl chloride was used in the next step without further purification. The following sulfamoyl chlorides were prepared:
Benzylsulfamoyl chloride, Phenylsulfamoyl chloride, 2,4-Difluoro-phenylsulfamoyl chloride, 2,5-Difuoro-phenylsulfamoyl chloride, 3,4-Difuoro-phenylsulfamoyl chloride, 3-Fluoro phenyl- sulfamoyl chloride, 4-Fluoro-phenylsulfamoyl chloride, 4-Chloro-phenylsulfamoyl chloride, 4-Bromo-phenylsulfamoyl chloride, 4-Methyl-phenylsulfamoyl chloride, 4-trifluoromethyl-phenylsulfamoyl chloride, 4-Cyano-phenylsulfamoyl chloride, 4-Methoxy-phenylsulfamoyl chloride, Butylsulfamoyl chloride, Phenethylsulfamoyl chloride, 2-Phenoxyethylsulfamoyl chloride, Cyclohexylmethylsulfamoyl chloride, Cyclopropylsulfamoyl chloride, 2,2,2-Trifluoroethylsulfamoyl chloride, 4-Fluoro-benzylsulfamoyl chloride, Furan-2-ylmethylsulfamoyl chloride, Benzo[1,3]dioxol-5-ylmethylsulfamoyl chloride.

Example 12

Sulfamoyl chlorides were prepared according to the following procedure. 1 equivalent of the corresponding amine hydrochloride was dissolved in $CH_3CN$ and placed in an ice bath. Sulfuryl chloride (3 eq.) was added slowly within 20 min. The reaction mixture was stirred at room temperature for 15 min and at 65° C. for 20 h. The solvent was evaporated and the residue was dried under high vacuum. The crude sulfamoyl chloride was used in the next step without further purification. The following sulfamoyl chlorides were prepared:
Chlorosulfonylamino-acetic acid ethyl ester, 4-(Chlorosulfonylamino-methyl)-benzoic acid methyl ester.

Example 13

A solution of 1.26 (6.03 mmol) of 4-(4-Dimethylamino-butoxy)-phenylamine in 15 ml dioxane was treated with 1.13 ml (6.1 mmol) Hünigsbase and 1.86 g (7.59 mmol) 4-(trifluoromethyl)benzenesulfonyl chloride. The reaction mixture was stirred over night at room temperature and extracted with aqueous saturated $NaHCO_3$ solution/EtOAc (3×). The organic phase was dried over $Na_2SO_4$ and evaporated. The residue (partially disulfonamide) was dissolved in 20 ml dioxane, treated with 11.1 ml 1N NaOH and heated for 1 h at 100° C. The reaction mixture was neutralized (pH 7 with 1 N HCl) and extracted with EtOAc (2×). The organic phase was washed with aqueous saturated $NaHCO_3$, dried over $Na_2SO_4$ and evaporated to yield 2.1 g (84%) of N-[4-(4-Dimethylamino-butoxy)-phenyl]-4-trifluoromethyl-benzenesulfonamide, MS: 417 (MH+).

Example 14

14.1
A solution of 98 mg (0.375 mmol) triphenylphosphine in 0.5 ml THF was treated at 0° C. with 0.06 ml (0.375 mmol) DEAD, then with 0.012 ml (0.3 mmol) methanol in 0.33 ml THF and finally with 104 mg (0.25 mmol) of N-[4-(4-Dimethylamino-butoxy)-phenyl]-4-trifluoromethyl-benzenesulfonamide in 0.3 ml THF. The reaction mixture was stirred over night at RT, evaporated and extracted with aqueous saturated $NaHCO_3$/Et2O (3×). The organic phases were dried over $Na_2SO_4$ evaporated and purified by flash column chromatography on silica gel with $CH_2Cl_2$/MeOH (99:1 to 95:5) to yield 80 mg (74%) of N-[4-(4-Dimethylamino-butoxy)-phenyl]-N-methyl-4-trifluoromethyl-benzenesulfonamide, mp: 151–153° C.; MS: 431 ($MH^+$).

14.2

In analogy to example 14.1, reaction of N-[4-(4-Dimethylamino-butoxy)-phenyl]-4-trifluoromethyl-benzenesulfonamide 69-2511 with 1-propanol yielded N-[4-(4-Dimethylamino-butoxy)-phenyl]-N-isopropyl-4-trifluoromethyl-benzenesulfonamide, MS: 459 ($MH^+$).

14.3

In analogy to example 14.1, reaction of N-[4-(4-Dimethylamino-butoxy)-phenyl]-4-trifluoromethyl-benzenesulfonamide 69-2511 with ethanol yielded N-[4-(4-Dimethylamino-butoxy)-phenyl]-N-ethyl-4-trifluoromethyl-benzenesulfonamide, MS: 445 ($MH^+$).

Example 15

15.1

13.8 g (40 mmol) of 4-methylaminophenol hemisulfate (twice suspended in toluene and evaporated under reduced pressure to remove water) were suspended in 100 ml hexamethyldisilazane and refluxed for 2.5 h. The solution was evaporated under reduced pressure and dissolved in 270 ml THF. 9.79 g (40 mmol) of 4-(trifluoromethyl)benzenesulfonyl chloride were added slowly at 0° C. and the reaction mixture was stirred for 16 h at room temperature. 30 ml $H_2O$ were added and after 1 h the solvents were evaporated. The residue was extracted with water/$Et_2O$ (3×), the organic phases were washed with 10% NaCl, dried ($Na_2SO_4$) and evaporated to yield 13.3 g (100%) of N-(4-hydroxy-phenyl)-N-methyl-4-trifluoromethyl-benzenesulfonamide, mp: 145–146° C.; MS: 331 (M).

15.2

In analogy to example 15.1, reaction of 4-methylaminophenol hemisulfate with 4-chlorophenylchloroformate yielded (4-Hydroxy-phenyl)-methyl-carbamic acid 4-chloro-phenyl ester, mp: 143–145° C., dec.; MS: 278 ($MH^+$, 1Cl).

Example 16

16.1

A solution of 6.63 g (20 mmol) of N-(4-Hydroxy-phenyl)-N-methyl-4-trifluoromethyl-benzenesulfonamide in 150 ml of DMF was treated with 7.1 ml (60 mmol) of 1,4-dibromobutane and with 1.00 g (23 mmol) of 55% NaH (in small portions) at 0° C. The reaction mixture was stirred for 4 h at RT, poured into cooled aqueous saturated $NH_4Cl$ and extracted ($Et_2O$ 3×). The organic phase was washed with aqueous 10% NaCl, dried ($NaSO_4$) evaporated and purified by flash silica gel column (first with hexane to remove the dibromobutane and then Hexane/EtOAc 95:5) to yield 7.7 g (83%) of N-[4-(4-Bromo-butoxy)-phenyl]-N-methyl-4-trifluoromethyl-benzenesulfonamide, mp: 91–92° C.; MS: 465 (M, 1 Br).

16.2

In analogy to example 16.1, (4-Hydroxy-phenyl)-methyl-carbamic acid 4-chloro-phenyl ester 69–9787 was converted to [4-(4-Bromo-butoxy)-phenyl]-methyl-carbamic acid 4-chloro-phenyl ester, MS: 412 ($MH^+$, 1 Br, 1Cl).

Example 17

17.1

A solution of 466 mg (1 mmol) of N-[4-(4-Bromo-butoxy)-phenyl]-N-methyl-4-trifluoromethyl-benzenesulfonamide 69–9844 in 3.5 ml DMA was treated at 0° C. with 0.195 ml (2 mmol) of 2-ethylaminoethanol and stirred at RT for 15 h. The reaction mixture was cooled (0° C.) again, treated with 0.195 ml (2 mmol) of 2-ethylaminoethanol and stirred at RT for further 24 h. The solution was concentrated, the residual oil was dissolved in water/acetontrile 1:1/5% formic acid and purified by prep. HPLC: RP-18, acetonitrile/water, 10%–60% acetonitrile. The pure fractions were collected, dissolved in EtOAc, washed with aqueous sat. $NaHCO_3$ solution, and the organic phase was dried ($Na_2SO_4$) and evaporated to yield 360 mg (76%) of N-(4-{4-[Ethyl-(2-hydroxy-ethyl)-amino]-butoxy}-phenyl)-N-methyl-4-trifluoromethyl-benzenesulfonamide, MS: 475 ($MH^+$).

17.2

In analogy to example 17.1, reaction of N-[4-(4-Bromo-butoxy)-phenyl]-N-methyl-4-trifluoromethyl-benzenesulfonamide with N-methylallylamine yielded N-{4-[4-(Allyl-methyl-amino)-butoxy]-phenyl}-N-methyl-4-trifluoromethyl-benzenesulfonamide; compound with formic acid, MS: 457 ($MH^+$).

17.3

In analogy to example 17.1, reaction of N-[4-(4-Bromo-butoxy)-phenyl]-N-methyl-4-trifluoromethyl-benzenesulfonamide with diethylamine yielded N-[4-(4-Diethylamino-butoxy)-phenyl]-N-methyl-4-trifluoromethyl-benzenesulfonamide, MS: 459 ($MH^+$).

17.4

In analogy to example 17.1, reaction of [4-(4-Bromo-butoxy)-phenyl]-methyl-carbamic acid 4-chloro-phenyl ester with 2-ethylaminoethanol yielded (4-{4-[Ethyl-(2-hydroxy-ethyl)-amino]-butoxy}-phenyl)-methyl-carbamic acid 4-chloro-phenyl ester, MS: 421 ($MH^+$).

17.5

In analogy to example 17.1, reaction of [4-(4-Bromo-butoxy)-phenyl]-methyl-carbamic acid 4-chloro-phenyl ester with N-methylallylamine yielded {4-[4-(Allyl-methyl-amino)-butoxy]-phenyl}-methyl-carbamic acid 4-chloro-phenyl ester; compound with formic acid, MS: 403 ($MH^+$).

17.6

In analogy to example 17.1, reaction of [4-(4-Bromo-butoxy)-phenyl]-methyl-carbamic acid 4-chloro-phenyl ester with 10 eq dimethylamine (33% in ethanol, 5.6 M) yielded [4-(4-Dimethylamino-butoxy)-phenyl]-methyl-carbamic acid 4-chloro-phenyl ester; compound with formic acid, MS: 377 ($MH^+$).

17.7

In analogy to example 17.1, reaction of [4-(4-Bromo-butoxy)-phenyl]-methyl-carbamic acid 4-chloro-phenyl ester with diethylamine yielded [4-(4-Diethylamino-butoxy)-phenyl]-methyl-carbamic acid 4-chloro-phenyl ester, MS: 405 ($MH^+$).

Example 18

18.1

A solution of 21.9 g (100 mmol) 4-iodoaniline and 22.9 g (105 mmol) of di-tert-butyl dicarbonate in 300 ml THF was heated for 30 h at 80° C. The solution was evaporated and extracted with aqueous 10% $KHSO_4$/$Et_2O$ (3×). The organic phase was washed with aqueous 10% NaCl, dried over $Na_2SO_4$ and evaporated to yield 31.0 g (97%) of (4-Iodo-phenyl)-carbamic acid tert-butyl ester, MS: 320 ($MH^+$).

18.2

A solution of 15.96 g (50 mmol) (4-Iodo-phenyl)-carbamic acid tert-butyl ester and 24.96 ml (400 mmol) iodomethane in 250 ml THF was treated at –18° C. with 4.36 (100 mmol) 55% NaH during 1 h. The reaction was warmed up over night to room temperature, neutralized at 0° C. with aqueous 10% $KHSO_4$, evaporated and extracted with aqueous 10% KHSO$_4$/Et$_2$O (3×). The organic phases were washed with aqueous 10% NaCl, dried (Na$_2$SO$_4$) and evaporated to yield 17.8 g (quantitative) of (4-Iodo-phenyl)-methyl-carbamic acid tert-butyl ester, MS: 333 (M).

18.3

The synthesis was performed following a procedure of Stara, Irena G.; Stary, Ivo; Kollarovic, Adrian; Teply, Filip; Saman, David; Fiedler, Pavel. Coupling reactions of halobenzenes with alkynes. The synthesis of phenylacetylenes and symmetrical or unsymmetrical 1,2-diphenylacetylenes. Collect. Czech. Chem. Commun. (1999), 64(4), 649–672. A solution of 4.45 g (12.5 mmol) of (4-Iodo-phenyl)-methyl-carbamic acid tert-butyl ester in 25 ml piperidine was degassed (argon) and treated with 722 mg (0.625 mmol) Pd(PPh$_3$)$_4$ and 119 mg (0.625 mmol) CuI. The reaction mixture was stirred at 45° C. for 10 min and then slowly (45 min) heated to 80° C. while adding 0.9 ml (9.4 mmol) of 4-pentin-1-ol. At 80° C. a second portion of 0.9 ml (9.4 mmol) 4-pentin-1-ol was added during 45 min. The reaction mixture was stirred at this temperature for 2 h and then extracted with chilled water acidified with KHSO$_4$/Et$_2$O (3×). The organic phases were washed with aqueous 10% NaCl, dried (Na$_2$SO$_4$) and evaporated. Purification by flash-chromatography on silica gel (CH$_2$Cl$_2$/EtOAc 95:5) yielded 3.15 g (87%) of [4-(5-Hydroxy-pent-1-ynyl)-phenyl]-methyl-carbamic acid tert-butyl ester, mp: 103–105° C.; MS: 289 (M).

18.4

In analogy to example 18.3, reaction of (4-Iodo-phenyl)-methyl-carbamic acid tert-butyl ester with propargylalcohol yielded [4-(3-Hydroxy-prop-1-ynyl)-phenyl]-methyl-carbamic acid tert-butyl ester, MS: 261 (M$^+$).

18.5

A solution of 3.02 g (10.44 mmol) of [4-(5-Hydroxy-pent-1-ynyl)-phenyl]-methyl-carbamic acid tert-butyl ester in 70 ml CH$_2$Cl$_2$ was treated at 0° C. with 0.89 ml (11.48 mmol) methanesulfonylchloride, 1.26 ml (15.66 mmol) pyridine and 1.28 g (10.44 mmol) DMAP. The reaction mixture was warmed up over night to room temperature, water (10 ml) was added and the reaction mixture was stirred for 5 min. After extraction with aqueous 10% KHSO$_4$/Et$_2$O (3×) the organic phases were washed with aqueous KHCO$_3$ (2×), aqueous 10% NaCl, dried (Na$_2$SO$_4$) and evaporated to yield 3.74 g (97%) of Methanesulfonic acid 5-[4-(tert-butoxycarbonyl-methyl-amino)-phenyl]-pent-4-ynyl ester, mp: 85–87° C.; MS: 367 (M).

18.6

In analogy to example 18.5, [4-(3-Hydroxy-prop-1-ynyl)-phenyl]-methyl-carbamic acid tert-butyl ester was converted to [4-(3-Chloro-prop-1-ynyl)-phenyl]-methyl-carbamic acid tert-butyl ester, MS: 279 (MH+, 1Cl).

18.6

A solution of 1.84 g (5 mmol) of Methanesulfonic acid 5-[4-(tert-butoxycarbonyl-methyl-amino)-phenyl]-pent-4-ynyl ester in 20 ml DMA was treated with 8.93 ml (50 mmol) of (33% in ethanol, 5.6 M) dimethylamine and stirred at RT for 18 h. The reaction was treated again with 4.46 ml (2 mmol) (25 mmol) of (33% in ethanol, 5.6 M) dimethylamine and stirred at RT for further 6 h. The solution was concentrated and the residual oil was extracted with aqueous sat. NaHCO3/Et$_2$O (3×). The organic phases were washed with aqueous 10% NaCl solution, dried (Na$_2$SO$_4$) and evaporated to yield 1.50 g (95%) of [4-(5-Dimethylamino-pent-1-ynyl)-phenyl]-methyl-carbamic acid tert-butyl ester, MS: 317 (MH$^+$).

18.7

In analogy to example 18.6, reaction of [4-(3-Chloro-prop-1-ynyl)-phenyl]-methyl-carbamic acid tert-butyl ester with N-allylmethylamine yielded {4-[3-(Allyl-methyl-amino)-prop-1-ynyl]-phenyl}-methyl-carbamic acid tert-butyl ester, MS: 315 (MH$^+$).

18.8

A solution of 1.45 g (4.58 mmol) of [4-(5-Dimethylamino-pent-1-ynyl)-phenyl]-methyl-carbamic acid tert-butyl ester in 25 ml CH$_2$Cl$_2$ was treated at 0° C. with 11.5 ml TFA (during 20 min) and warmed up to room temperature during 1 h. The solution was concentrated and the residual oil was extracted with aqueous sat. NaHCO$_3$ (+Na$_2$CO$_3$)/EtOAc (3×). The organic phase was dried (Na$_2$SO$_4$) and evaporated to yield 1.05 g (quantitative) of [4-(5-Dimethylamino-pent-1-ynyl)-phenyl]-methyl-amine MS: 217 (MH$^+$).

18.9

In analogy to experiment 18.9, {4-[3-(Allyl-methyl-amino)-prop-1-ynyl]-phenyl}-methyl-carbamic acid tert-butyl ester was converted to {4-[3-(Allyl-methyl-amino)-prop-1-ynyl]-phenyl}-methyl-amine, MS: 214 (M).

18.10

A solution of 59 mg (0.27 mmol) of [4-(5-Dimethylamino-pent-1-ynyl)-phenyl]-methyl-amine in 0.3 ml dioxane was treated with 0.07 ml (0.55 mmol; 2 equivalents) Hünigsbase and dropwise with a solution of 0.05 ml (0.27 mmol) 4-chlorophenylchloroformate in 0.45 ml dioxane. The mixture was then immediately dissolved in aqueous saturated NaHCO$_3$ IEt$_2$O (3×). The organic phase was dried over Na$_2$SO$_4$ and evaporated. Flash column chromatography on silica gel with CH$_2$Cl$_2$/MeOH (95:5) yielded 55 mg (54%) of [4-(5-Dimethylamino-pent-1-ynyl)-phenyl]-methyl-carbamic acid 4-chloro-phenyl ester, MS: 371 (MH$^+$, 1Cl).

18.11

A solution of 0.100 g (0.47 mmol) of {4-[3-(Allyl-methyl-amino)-prop-1-ynyl]-phenyl}-methyl-amine in 4 ml THF −78° C. was treated with 0.31 ml (0.49 mmol) BuLi (ca 1.6 M in hexane) and stirred for 20 min. A solution of 0.07 ml (0.49 mmol) 4-chlorophenyl-chloroformate in 4 ml THF was then added. The reaction was warmed up to 0° C. during 2 h and neutralized with aqueous 10% KHSO$_4$. The mixture was treated with aqueous saturated NaHCO$_3$/Et$_2$O (3×). The organic phase was dried over Na$_2$SO$_4$ and evaporated. The residual oil was dissolved in water/acetontrile 1:1/5% formic acid and purified by prep. HPLC: RP-18, acetonitrile/water, 10%–40% acetonitrile. The pure fractions were collected, dissolved in Et$_2$O, washed with aqueous sat. NaHCO$_3$/1N NaOH solution, and the organic phase was dried (Na$_2$SO$_4$) and evaporated to yield 0.047 g (45%) of {4-[3-(Allyl-methyl-amino)-prop-1-ynyl]-phenyl}-methyl-carbamic acid 4-chloro-phenyl ester, MS: 369 (MH$^+$, 1Cl).

18.12

A solution of 173 mg (0.8 mmol) of [4-(5-Dimethylamino-pent-1-ynyl)-phenyl]-methyl-amine in 2 ml dioxane was treated with 0.15 ml (0.88 mmol) Huinigsbase and 247 mg (1 mmol) 4-(trifluoromethyl)benzenesulfonyl chloride. The reaction mixture was stirred over night at room temperature and extracted with aqueous 10% KHSO$_4$/EtOAc (3×). The aqueous phase was treated with NaHCO$_3$ (pH 7–8) and extracted with CH$_2$Cl$_2$ (3×). The organic phase was dried over Na$_2$SO$_4$ and evaporated. Flash column chromatography on silica gel with CH$_2$Cl$_2$/MeOH (9:1) yielded 223 mg (65%) of N-[4-(5-Dimethylamino-pent-1-ynyl)-phenyl]-N-methyl-4-trifluoromethyl-benzenesulfonamide, MS: 425 (MH$^+$).

18.13

A solution of 40 mg (0.094 mmol) of N-[4-(5-Dimethylamino-pent-1-ynyl)-phenyl]-N-methyl-4- trifluoromethyl-benzenesulfonamide in 3 ml MeOH/0.3 ml dioxane was treated with 0.094 ml 1N AcOH in MeOH followed by 4 mg Pd/C$_{10}$%, type EION (under argon) and then hydrogenated (1 atm) for 3 h. The reaction mixture was filtered (Celite) and extracted with aqueous sat. NaHCO$_3$/ Et$_2$O (3×). The organic phases were washed with aqueous 10% NaCl solution, dried (Na$_2$SO$_4$) and evaporated to yield 27 mg (66%) of N-[4-(5-Dimethylamino-pentyl)-phenyl]-N-methyl-4-trifluoromethyl-benzenesulfonamide, MS: 429 (MH$^+$).

Example 19

19.1

20 g (114.9 mmol) 2-amino-5-bromopyridine and 26.3 g (120.7 mmol) di-tert-butyl dicarbonate in 300 ml THF/300 ml CH$_3$CN were treated with 9.7 ml (120 mmol) pyridine, 0.7 g (11.5 mmol) DMAP and stirred for 23 h at RT and heated for 2 h at 80° C. The reaction mixture was again treated with 13.2 g (60.4 mmol) of di-tert-butyl dicarbonate, 4.85 ml (60 mmol) pyridine, 0.35 g (5.8 mmol) DMAP and heated for 2 h at at 80° C. After evaporation and extraction with aqueous 10% KHSO$_4$ /Et$_2$O (3×), the organic phase was washed with aqueous 10% NaCl, dried over Na$_2$SO$_4$ and evaporated to yield 28.4 g (66%) of imidodicarbonic acid, (5-bromo-2-pyrimidinyl)-, bis(1,1-dimethylethyl) ester, mp: 119–121° C.; MS: 374 (MH$^+$).

19.2

The synthesis was performed following a procedure of Arco Y. Jeng; Design and Synthesis of Potent, Selective Inhibitors of Endothelin-Converting Enzyme, Journal of Medicinal Chemistry; 1998; 41(9); 1513–1523. A solution of 18.7 (50 mmol) of imidodicarbonic acid, (5-bromo-2-pyrimidinyl)-, bis(1,1-dimethylethyl) ester in 600 ml DMF was degassed (argon) and under argon treated with 13.9 ml (100 mmol) Et$_3$N, 1.9 g (10 mmol) CuI and 2.04 g (2.5 mmol) PdCl$_2$(dppf).CH$_2$Cl$_2$. The reaction mixture was stirred at 80° C. and slowly (1.5 h) treated with 7.16 ml (75 mmol) of 4-pentin-1-ol. The reaction mixture was stirred at this temperature for 4 h and then extracted with chilled water/Et$_2$O (3×). The organic phases were washed with aqueous 10% NaCl, dried (Na$_2$SO$_4$) and evaporated. Purification by flash-chromatography on silica gel (hexane/ EtOAc 2:1 to 1:1) yielded 15.63 g (83%) of imidodicarbonic acid, [5-(5-hydroxy-1-pentynyl)-2-pyrimidinyl]-, bis(1,1-dimethylethyl) ester, mp: 91–92° C.; MS: 378 (MH$^+$).

19.3

A solution of 7.55 g (20 mmol) of imidodicarbonic acid, [5-(5-hydroxy-1-pentynyl)-2-pyrimidinyl]-, bis(1,1-dimethylethyl) ester in 140 ml CH$_2$Cl$_2$ was treated at 0° C. with 1.71 ml (22 mmol) methanesulfonylchloride, 2.41 ml (30 mmol) pyridine and 2.45 g (20 mmol) DMAP. The reaction mixture was warmed up over night to room temperature, water (10 ml) was added and the reaction mixture was stirred for 5 min. After extraction with aqueous 10% KHSO$_4$/Et$_2$O (3×) the organic phases were washed with aqueous KHCO$_3$ (2×), aqueous 10% NaCl, dried (Na$_2$SO$_4$) and evaporated to yield 9.67 g (quantitative) of imidodicarbonic acid, [5-[5-[(methylsulfonyl)oxy]-1-pentynyl]-2-pyrimidinyl]-, bis(1,1-dimethylethyl) ester, MS: 456 (MH$^+$).

19.4

A solution of 5.36 g (11.7 mmol) of imidodicarbonic acid, [5-[5-[(methylsulfonyl)oxy]-1-pentynyl]-2-pyrimidinyl]-, bis(1,1-dimethylethyl) ester in 45 ml DMA was treated with 20.9 ml (116.8 mmol) of (33% in ethanol, 5.6 M) dimethylamine and stirred at RT for 16 h. The solution was concentrated (0.01 torr, 55° C.) and the residual oil was extracted with aqueous sat. NaHCO$_3$/Et$_2$O (3×). The organic phases were washed with aqueous 10% NaCl solution, dried (Na$_2$SO$_4$) and evaporated to yield 3.32 g (93%) of [5-(5-Dimethylamino-pent-1-ynyl)-pyrimidin-2-yl]-carbamic acid tert-butyl ester, mp: 119–120° C.; MS: 305 (MH$^+$).

19.5

A solution of 1.47 g (3.2 mmol) of [5-(5-Dimethylamino-pent-1-ynyl)-pyrimidin-2-yl]-carbamic acid tert-butyl ester in 16 ml CH$_2$Cl$_2$ was treated at 0° C. with 8 ml TFA (during 20 min). The solution was warmed up to room temperature during 1 h, concentrated and the residual oil was extracted with aqueous sat. NaHCO$_3$ (+Na$_2$CO$_3$)(3×)/CH$_2$Cl$_2$(3×). The organic phases were washed with aqueous 10% NaCl solution, dried (Na$_2$SO$_4$) and evaporated to yield 0.62 g (95%) of 5-(5-Dimethylamino-pent-1-ynyl)-pyrimidin-2-ylamine, mp: 126–127° C.; MS: 205 (MH$^+$).

19.6

A solution of 102 mg (0.5 mmol) of 5-(5-Dimethylamino-pent-1-ynyl)-pyrimidin-2-ylamine in 3.9 ml pyridine was treated with 257 mg (1.05 mmol) 4-(trifluoromethyl) benzenesulfonyl chloride. The reaction was stirred over night at 70° C., evaporated and extracted with aqueous saturated NaHCO$_3$(2×)/CH$_2$Cl$_2$ (3×). The organic phases were washed with aqueous 10% NaCl solution, dried (Na$_2$SO$_4$) and evaporated. Flash column chromatography on silica gel with CH$_2$Cl$_2$/MeOH (95:5 to 9:1) yielded 70 mg (34%) of N-[5-(5-Dimethylamino-pent-1-ynyl)-pyrimidin-2-yl]-4-trifluoromethyl-benzenesulfonamide, mp: 194–202° C.,slowly dec.; MS: 413 (MH$^+$).

19.7

A solution of 127 mg (0.485 mmol) triphenylphosphine in 0.5 ml THF was treated at 0° C. with 0.075 ml (0.485 mmol) DEAD, then with 0.016 ml (0.388 mmol) methanol and finally with 80 mg (0.19 mmol) of N-[5-(5-Dimethylamino-pent-1-ynyl)-pyrimidin-2-yl]-4-trifluoromethyl-benzenesulfonamide in 0.3 ml THF. The reaction mixture was stirred over night at RT, evaporated and extracted with aqueous saturated NaHCO$_3$/Et$_2$O (3×). The organic phases were dried over Na$_2$SO$_4$, evaporated and purified by flash column chromatography on silica gel with CH$_2$Cl$_2$/MeOH (99:1 to 95:5) to yield 19 mg (23%) of N-[5-(5-Dimethylamino-pent-1-ynyl)-pyrimidin-2-yl]-N-methyl-4-trifluoromethyl-benzenesulfonamide, MS: 427 (MH$^+$).

Example A

Tablets containing the following ingredients can be manufactured in a conventional manner:

| Ingredients | Per tablet |
| --- | --- |
| Compound of formula I | 10.0–100.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 25.0 mg |
| Lactose | 150.0 mg |
| Maize starch | 20.0 mg |
| Talc | 5.0 mg |

Example C

Injection solutions can have the following composition:

| Compound of formula I | 3.0 mg |
| --- | --- |
| Gelatine | 150.0 mg |
| Phenol | 4.7 mg |
| Water for injection solutions | ad 1.0 ml |

What is claimed is:

1. A compound of formula (I)

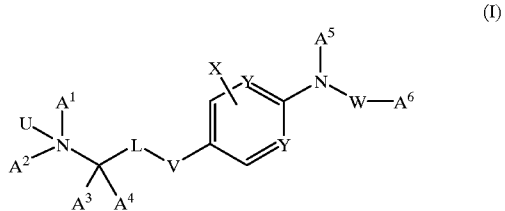

wherein
U is O or a lone pair,
Y is C or N,
V is O, S, $NR_6$, —$CH_2$—, —CH═CH—, or —C≡C—, if Y is C, or —$CH_2$—, —CH═CH—, or —C≡C—, if Y is N,
W is CO, COO, $CONR^1$, CSO, $CSNR^1$, $SO_2$, or $SO_2NR^1$,
L is lower-alkylene, lower-alkenylene, or a single bond,
$A^1$ is H, lower-alkyl, or lower-alkenyl,
$A^2$ is lower-alkyl, cycloalkyl, cycloalkyl-lower-alkyl, lower-alkenyl, or lower-alkinyl, each unsubstituted ot substituted by $R^2$,
$A^3$, $A^4$ are hydrogen or lower-alkyl, or
$A^1$ and $A^2$ or $A^1$ and $A^3$ are bonded to each other to form a ring and —$A^1$—$A^2$— or —$A^1$—$A^3$— are lower-alkylene or lower-alkenylene, each unsubstituted or substituted by $R^2$, or are lower-alkylene or lower-alkenylene, each unsubstituted or substituted by R2, in which one —$CH_2$— group of —$A^1$—$A^2$— or —$A^1$—$A^3$— is replaced by $NR^3$, S, or O,
$A^5$ is lower-alkyl,
X is hydrogen or one or more halogen substituents,
$A^6$ is lower-alkyl, cycloalkyl, cycloalkyl-lower-alkyl, heterocycloalkyl-lower-alkyl, lower alkenyl, lower-alkadienyl, aryl, aryl-lower-alkyl, heteroaryl, or heteroaryl-lower-alkyl,
$R^2$ is hydroxy, hydroxy-lower-alkyl, lower-alkoxy, N($R^4$, $R^5$), or lower-alkoxycarbonyl,
$R^1$, $R^3$, $R^4$, $R^5$ and $R^6$ independently from each other are hydrogen or lower-alkyl, or a pharmaceutically acceptable salt or pharmaceutically acceptable ester thereof.

2. A compound according to claim 1, wherein U is a lone pair.

3. A compound according to claim 1, wherein U is O.

4. A compound according to claim 1, wherein Y is C.

5. A compound according to claim 4, wherein V is O, —C≡C—, —$CH_2$—.

6. A compound according to claim 5, wherein V is O.

7. A compound according to claim 1, wherein W is COO, $SO_2$, or $CSNR^1$ and $R^1$ is hydrogen.

8. A compound according to claim 1, wherein L is lower-alkylene or a single bond.

9. A compound according to claim 8, wherein L is —$(CH_2)_{2-4}$—.

10. A compound according to claim 1, wherein $A^1$ is methyl, ethyl, or 2-propenyl.

11. A compound according to claim 1, wherein $A^2$ is lower-alkyl, cycloalkyl, lower-alkenyl, or lower-alkinyl, each unsubstituted or substituted with $R^2$, wherein $R^2$ is hydroxy, methoxy, or ethoxycarbonyl.

12. A compound according to claim 11, wherein $A^2$ is methyl, ethyl, 2-hydroxyethyl, or 2-propenyl.

13. A compound according to claim 1, wherein $A^1$ and $A^2$ are bonded to each other to form a ring and —$A^1$—$A^2$— is lower-alkylene, or lower-alkenylene, each unsubstituted or substituted by $R^2$, or —$A^1$—$A^2$— is lower-alkylene, or lower-alkenylene, each unsubstituted or substituted by R2, in which one —$CH_2$— group of —$A^1$—$A^2$— is replaced by $NR^3$, S, or O.

14. A compound according to claim 13, wherein $R^2$ is methyl, hydroxy, 2-hydroxyethyl, or $N(CH_3)_2R^3$ is methyl.

15. A compound according to claim 13, wherein $R^3$ is methyl.

16. A compound according to claim 1, wherein $A^3$ is hydrogen.

17. A compound according to claim 1, wherein $A^4$ is hydrogen.

18. A compound according to claim 1, wherein $A^5$ is methyl or ethyl.

19. A compound according to claim 1, wherein X is hydrogen.

20. A compound according to claim 1, wherein $A^6$ is lower-alkyl, lower-alkenyl, phenyl or phenyl-lower-alkyl, wherein the phenyl group is unsubstituted or substituted by one or more substituents of lower-alkyl, lower-alkoxy, fluorine, chlorine, bromine, CN, $CF_3$, $NO_2$, or $N(R^6,R^7)$, wherein $R^6$ and $R^7$ independently from each other are hydrogen or lower-alkyl.

21. A compound according to claim 20, wherein $A^6$ is 4-trifluoromethyl-phenyl or 4-chloro-phenyl.

22. A compound according to claim 1, {4-[4-(Allyl-methyl-amino)-butoxy]-phenyl}-methyl-carbamic acid 4-chloro-phenyl ester.

23. A compound according to claim 1, N-{4-[4-(Allyl-methyl-amino)-butoxy]-phenyl}-N-methyl-4-trifluoromethyl-benzenesulfonamide.

24. A compound according to claim 1, N-[4-(4-Dimethylamino-butoxy)-phenyl]-N-methyl-4-trifluoromethyl-benzenesulfonamide.

25. A compound according to claim 1, N-[4-(4-Diethylamino-butoxy)-phenyl]-N-methyl-4-trifluoromethyl-benzenesulfonamide.

26. A compound according to claim 1, [4-(5-Dimethylamino-pent-1-ynyl)-phenyl]-methyl-carbamic acid 4-chloro-phenyl ester.

27. A compound according to claim 1, [4-(4-Diethylamino-butoxy)-phenyl]-methyl-carbamic acid 4-chloro-phenyl ester.

28. A compound according to claim 1, (4-{4-[Ethyl-(2-hydroxy-ethyl)-amino]-butoxy}-phenyl)-methyl-carbamic acid 4-chloro-phenyl ester.

29. A compound according to claim 1, [4-(4-Dimethylamino-butoxy)-phenyl]-methyl-carbamic acid 4-chloro-phenyl ester.

30. A compound according to claim 1, N-(4-{4-[Ethyl-(2-hydroxy-ethyl)-amino]-butoxy}-phenyl)-N-methyl-4-trifluoromethyl-benzenesulfonamide.

31. A compound according to claim 1, N-[4-(4-Dimethylamino-butoxy)-phenyl]-N-ethyl-4-trifluoromethyl-benzenesulfonamide.

32. A compound according to claim 1, 1-{4-[6-(Allyl-methyl-amino)-hexyloxy]-phenyl}-3-(4-chloro-phenyl)-1-methyl-thiourea.

* * * * *